United States Patent
Mukherjee

(10) Patent No.: US 9,090,698 B2
(45) Date of Patent: *Jul. 28, 2015

(54) TUMOR SPECIFIC ANTIBODIES AND USES THEREFOR

(75) Inventor: Pinku Mukherjee, Waxhaw, NC (US)

(73) Assignee: The University of North Carolina at Charlotte, Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/877,582

(22) PCT Filed: May 25, 2011

(86) PCT No.: PCT/US2011/037972
§ 371 (c)(1),
(2), (4) Date: Sep. 6, 2013

(87) PCT Pub. No.: WO2012/047317
PCT Pub. Date: Apr. 12, 2012

(65) Prior Publication Data
US 2013/0336886 A1    Dec. 19, 2013

Related U.S. Application Data

(63) Continuation-in-part of application No. 12/924,952, filed on Oct. 8, 2010, now Pat. No. 8,518,405.

(60) Provisional application No. 61/249,634, filed on Oct. 8, 2009.

(51) Int. Cl.

| | |
|---|---|
| *A61K 39/395* | (2006.01) |
| *C07K 16/30* | (2006.01) |
| *A61K 47/48* | (2006.01) |
| *A61K 49/00* | (2006.01) |
| *C07K 16/28* | (2006.01) |
| *G01N 33/574* | (2006.01) |
| *A61K 31/415* | (2006.01) |
| *A61K 31/7068* | (2006.01) |
| *A61K 45/06* | (2006.01) |
| *G01N 33/68* | (2006.01) |

(52) U.S. Cl.
CPC ........... *C07K 16/3092* (2013.01); *A61K 31/415* (2013.01); *A61K 31/7068* (2013.01); *A61K 39/39558* (2013.01); *A61K 45/06* (2013.01); *A61K 47/486* (2013.01); *A61K 47/48561* (2013.01); *A61K 47/48569* (2013.01); *A61K 49/0002* (2013.01); *C07K 16/2821* (2013.01); *C07K 16/30* (2013.01); *G01N 33/57438* (2013.01); *G01N 33/6893* (2013.01); *C07K 2317/33* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 7,183,388 B2 | 2/2007 | Denardo et al. | |
| 7,919,314 B2 | 4/2011 | Zvirbliene et al. | |
| 8,518,405 B2 * | 8/2013 | Mukherjee | 424/138.1 |
| 8,722,856 B2 | 5/2014 | Nishimura et al. | |
| 2003/0170761 A1 | 9/2003 | Stephens et al. | |
| 2004/0091480 A1 | 5/2004 | Hanai et al. | |
| 2006/0223096 A1 | 10/2006 | Umana et al. | |
| 2006/0292643 A1 | 12/2006 | Goletz et al. | |
| 2008/0057519 A1 | 3/2008 | McWhirter | |
| 2008/0214406 A1 | 9/2008 | Crea | |
| 2009/0053230 A1 | 2/2009 | Martin | |
| 2010/0003254 A1 | 1/2010 | Hattori et al. | |
| 2011/0123442 A1 | 5/2011 | Mukherjee | |
| 2012/0040375 A1 | 2/2012 | Nishimura et al. | |

FOREIGN PATENT DOCUMENTS

| | | |
|---|---|---|
| EP | 2199390 | 6/2010 |
| WO | WO2006/108658 | 10/2006 |
| WO | WO2006/109592 | 10/2006 |
| WO | WO2008/040362 | 4/2008 |
| WO | WO 2008/070171 | 6/2008 |
| WO | WO2010/042562 A2 | 4/2010 |
| WO | WO2010/050528 | 5/2010 |
| WO | WO2010/077854 | 7/2010 |
| WO | WO2010/113117 | 10/2010 |
| WO | WO2011/012309 | 2/2011 |
| WO | WO2012/004317 | 4/2012 |

OTHER PUBLICATIONS

Brown et al J. Immunol. May 1996; 156(9):3285-3291.*
Vajdos et al (J. Mol. Biol., Jul. 5, 2002;320(2); 415-428).*
Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Deutscher, Methods in Enzymology vol. 182 p. 663-670 (1990).*
Bieche & Lidereau (1997) Cancer Genetics and Cytogenetics 98:75-80.
Henderson et al. (1998) J Immunother 21:247-256.
Hingorani et al., "Preinvasive and invasive ductal pancreatic cancer and its early detection in the mouse," Cancer Cell, vol. 4, pp. 437-450 (2003).
Jackson et al., "Analysis of lung tumor initiation and progression using conditional expression of oncogenic K-rats," Genes Dev., vol. 15, pp. 3243-3248 (2001).

(Continued)

*Primary Examiner* — Sheela J Huff
(74) *Attorney, Agent, or Firm* — Jenkins, Wilson, Taylor & Hunt, P.A.

(57) ABSTRACT

Provided are isolated antibodies, and fragments and derivatives thereof, which bind to tumor antigens. Also provided are compositions and delivery agents that include the disclosed antibodies and fragments and derivatives thereof; cells that produce the same; methods for producing the same; methods of using the same for detecting, targeting, and/or treating tumors and/or metastatic cells derived therefrom and/or tumor stem cells; and methods for predicting the recurrence of cancer in a subject.

26 Claims, 10 Drawing Sheets

(56) References Cited

OTHER PUBLICATIONS

Kawaguchi et al., (2002) Nat Genet 32:128-134.

McGuckin et al. (1995) Human Pathology 26: 432-439.

Mukherjee et al., "Mice with Spontaneous Pancreatic Cancer Naturally Develop MUC-1-Specific CTLs That Eradicate Tumors When Adoptively Transferred," J. Immunol., vol. 165, pp. 3451-3460.

Mukherjee et al., "MUC1-specific immune therapy generates a strong anti-tumor response in a MUC1-tolerant colon cancer model," Vaccine, vol. 25, pp. 1607-1618(2007).

Mukherjee et al., "Progression of Pancreatic Adenocarcinoma Is Significantly Impeded with a Combination of Vaccine and COX-2 Inhibition," J. Immunol., vol. 182, pp. 216-224(2009).

Notice of Allowance corresponding to U.S. Appl. No. 12/924,952 dated Jul. 10, 2013.

Notification of Transmittal of the International Search Report and the Written Opinion of the International Searching Authority, or the Declaration corresponding to International Application No. PCT/US11/37972 dated Apr. 2, 2012.

Office Action corresponding to U.S. Appl. No. 12/924,952 dated Sep. 14, 2012.

Rowse et al., "Tolerance and Immunity to MUC1 in a Human MUC1 Transgenic Murine Model," Cancer Res., vol. 58, pp. 315-321.

Tinder et al., "MUC1 Enhances Tumor Progression and Contributes Toward Immunosuppression in a Mouse Model of Spontaneous Pancreatic Adenocarcinoma," J. Immunol., vol. 181, pp. 3116-3125 (2008).

Danielczyk et al., "PankoMab: a potent new generation anti-tumour MUC1 antibody", Cancer Immunology, Immunotherapy, vol. 55, No. 11, pp. 1337-1347 (Feb. 17, 2006).

European Search Report corresponding to European Application No. 11831066.3-1403 / 2624866 dated Feb. 4, 2014.

Kahn et al. (1987) Anticancer Res 7(4A):639-652.

Kirschenbaum et al., "MUCI expression in prostate carcinoma: Correlation with grade and stage", Molecular Urology, vol. 3, No. 3, pp. 163-167 (Jan. 1, 1999).

Leroy et al.,"Anatomic Pathology MUC1 in Renal Cell Carcinoma MUCI—Expression Is Correlated With Nuclear Grade and Tumor Progression in pT1 Renal Clear Cell Carcinoma," Jan. 1, 2002. URL:http://ajcp.ascpjournals.org/content/118/1/47.full.pdf [retrieved on Jan. 29, 2014].

Moreno et al., "High level of MUCI in serum of ovarian and breast cancer patients inhibits huHMFG-1 dependent cell-mediated cytotoxicity (ADCC)", Cancer Letters, vol. 257, No. 1, pp. 47-55 (Sep. 27, 2007).

Office Action corresponding to U.S. Appl. No. 13/948,580 dated Apr. 29, 2014.

Quin et al. (2000) Int J Cancer 87:499-506.

Rothenfusser et al. (2002) Human Immunology 63:1111-1119.

Office Action corresponding to U.S. Appl. No. 13/948,580 dated Nov. 7, 2014.

Office Action and Search Report corresponding to Chinese Patent Application No. 201180059040.8 dated Aug. 22, 2014. (Translation).

Office Action corresponding to Australian Patent Application No. 2011312830 dated May 30, 2014.

Office Action corresponding to Canadian Patent Application No. 2,813,814 dated Oct. 21, 2014.

Office Action corresponding to Japanese Patent Application No. 2013-532795 dated Nov. 18, 2014.

Office Action corresponding to Russian Patent Application No. 2013120483 dated Nov. 14, 2014.

Office Action corresponding to U.S. Appl. No. 13/948,580 dated Nov. 7, 2014.

\* cited by examiner

TUMOR SPECIFIC ANTIBODIES AND USES THEREFOR

CROSS REFERENCE TO RELATED APPLICATIONS

This application is a U.S. National Stage Application based on PCT International Patent Application Serial No. PCT/US2011/037972, filed May 25, 2011, which itself is a continuation-in-part of U.S. patent application Ser. No. 12/924,952, now U.S. Pat. No. 8,518,405, filed Oct. 8, 2010, which itself claims the benefit of U.S. Provisional Patent Application Serial No. 61/249,634, filed Oct. 8, 2009. The disclosure of each of these applications is incorporated herein by reference in its entirety.

REFERENCE TO SEQUENCE LISTING

The Sequence Listing associated with the instant disclosure has been electronically submitted to the United States Patent and Trademark Office as International Receiving Office as a twenty-one (21) kilobyte ASCII text file created on May 25, 2011 and entitled "1276_5PCT_ST25.txt". The Sequence Listing submitted via EFS-Web is hereby incorporated by reference in its entirety.

TECHNICAL FIELD

The presently disclosed subject matter relates to isolated antibodies, or fragments or derivatives thereof, which bind to antigens present in tumors, and methods of use therefor. In some embodiments, the presently disclosed subject matter relates to isolated antibodies, or fragments or derivatives thereof, that bind to the epithelial mucin family member MUC1, and to methods for using the same to detect, target, and treat tumors and tumor cells, including but not limited to circulating tumor cells (CTCs) and cancer stem cells (CSCs).

BACKGROUND

Pancreatic cancer is the fourth and fifth leading cause of cancer-related death for men and women, respectively, following lung, colon, and prostate cancers in men and lung, breast, colon, and ovarian cancers in women. Patients usually present with advanced disease, making treatment difficult. Surgery is the only curative therapy, yet local disease recurrence with or without spread to distant organs occurs in over 80% of patients. Attempts at better therapeutic modalities are necessary in order to improve outcome in this disease.

Frequently, neoplastic transformation leads to alterations in the expression of various polypeptides in tumor cells. For example, certain mucins and mutated forms of K-ras oncogene polypeptides are overexpressed in 90% of pancreatic ductal adenocarcinomas (hereinafter referred to as "FDA"), and have been targets for therapeutic interventions. To date, however, vaccines that target these polypeptides have not been particularly successful clinically. Vaccines have failed to generate long-term immune memory, likely due at least in part to tumors adapting in ways that allows them to escape immune recognition and killing. Several agents that can modulate immune tolerance have been tested clinically, but with only modest responses, perhaps due to an insufficient amount of the agents reaching the tumor site and/or because the agents themselves have been associated with unwanted side effects such as can result from their binding to normal cells.

Additionally, it is a major challenge in oncology to not only treat a patient's primary disease, but also to prevent the occurrence of metastases. It is currently believed that metastatic disease could result from the migration of tumorigenic cells, frequently referred to as tumor stem cells or cancer stem cells, from the primary tumor site to other sites, where they can infiltrate the site and form new tumors (see e.g., Bonnet & Dick, 1997; Reya et al., 2001; Al-Hajj et al., 2003; Pardal et al., 2003; Dontu et al., 2004; Singh et al., 2004; Brabletz et al., 2005). As a result, it would be beneficial to be able to identify and eliminate these cells should they be present in a patient.

Thus, there is therefore a need for new compositions and methods for detecting, targeting, and treating tumors and cells derived therefrom.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list all possible combinations of such features.

In various embodiments, the presently disclosed subject matter provides the following:

Isolated antibodies, as well as fragments and derivatives thereof, which specifically bind to mucin-1 (MUC1) and/or to mutated K-ras oncogene polypeptides present on epithelial tumors.

Isolated nucleic acids that encode the isolated antibodies of the presently disclosed subject matter and/or subsequences thereof.

Antibodies, such as monoclonal antibodies, and/or peptides, fragments, and/or derivatives thereof, that bind specifically to tumors such as epithelial tumors, including pancreatic tumors, ovarian tumors, breast tumors, colorectal tumors, and metastatic lesions derived therefrom.

Antibodies, as well as fragments and derivatives thereof, which bind specifically to an epitope present within a MUC1 polypeptide and/or a mutated K-ras$^{G12D}$ polypeptide, in some embodiments to an epitope present within a human MUC1 polypeptide. In some embodiments, the epitope is present within any of SEQ ID NOs: 1-3.

Antibodies, as well as fragments and derivatives thereof, which bind specifically to MUC1 (in some embodiments, human MUC1) and mutated K-ras$^{G12D}$ created using protein lysates from a mouse model which presents MUC1 and mutated K-ras$^{G12D}$ as tumor-associated antigens.

Chimeric molecules comprising antibodies, as well as fragments and derivatives thereof, attached to effectors and/or immune modulating agents, wherein the antibodies, or the fragments or derivatives thereof, bind specifically to epitopes present within a MUC1 polypeptide and/or a mutated K-ras polypeptide. In some embodiments, the effectors are selected from the group consisting of epitope tags, second antibodies (or fragments or derivatives thereof), labels, cytotoxins, liposomes, radionuclides, drugs, prodrugs, and chelates, and further wherein the immune modulating agent are selected from, for example, the agents listed in Table 3.

Antibodies, as well as fragments and derivatives thereof, coupled to an immune modulating agent; for example, the immune modulating agents listed in Table 3.

Antibodies, as well as fragments and derivatives thereof, coupled to diagnostic agents.

Antibodies, as well as fragments and derivatives thereof, prepared in compositions that comprise one or more pharmaceutically acceptable carriers and/or excipients.

Methods for inducing immune responses, which in some embodiments comprise introducing the antibodies, fragments, and/or derivatives thereof, and/or the compositions disclosed herein, into a subject such as, but not limited to, a human.

Methods for detecting cancerous cells, comprising introducing into a subject such as but not limited to a human an antibody, or a fragment or derivative thereof, coupled to a detectable label that bind specifically to a MUC1 polypeptide and/or a mutated K-ras polypeptide.

Hybridoma cells that produce the antibodies, fragments, and/or derivatives of the presently disclosed subject matter, such as but not limited to monoclonal antibodies that bind specifically to a MUC1 polypeptide, a mutated K-ras$^{G12D}$ polypeptide, or both.

Vaccines against epithelial cancers comprising the antibodies, fragments, and/or derivatives of the presently disclosed subject matter and one or more pharmaceutically accepted carriers and/or excipients, optionally further comprising one or mroe immune modulating agents.

More particularly, in some embodiments the presently disclosed subject matter provides isolated antibodies, or fragments or derivatives thereof, comprising the complementarity determining regions (CDRs) of monoclonal antibody TAB-004. In some embodiments, the isolated antibodies, or the fragments or derivatives thereof, are polyclonal. In some embodiments, the isolated antibodies, or the fragments or derivatives thereof, are monoclonal. In some embodiments, the isolated antibodies, or the fragments or derivatives thereof, are human or humanized. In some embodiments, the isolated antibodies, or the fragments or derivatives thereof, are selected from the group consisting of (a) a monoclonal antibody produced by hybridoma cell line TAB-004 deposited with the American Type Culture Collection (ATCC), University Boulevard, Manassas, Va., 20110-2209, United States of America, as Accession No. PTA-11550 on Dec. 16, 2010; (b) chimeric antibodies, or fragments or derivatives thereof; (c) humanized antibodies, or fragments or derivatives thereof; (d) human antibodies, or fragments or derivatives thereof; (e) single chain antibodies, or fragments or derivatives thereof; and (f) Fab fragments, wherein the chimeric antibodies, the humanized antibodies, the human antibodies, the single chain antibodies, or the Fab fragments comprise the CDRs of monoclonal antibody TAB-004. In some embodiments of the isolated antibodies, or the fragments or derivatives thereof, the CDRs comprise one or more of the following: (i) heavy chain CDR1 comprises SEQ ID NO: 8; (ii) heavy chain CDR2 comprises SEQ ID NO: 9; (iii) heavy chain CDR3 comprises SEQ ID NO: 10; (iv) light chain CDR1 comprises SEQ ID NO: 11; (v) light chain CDR2 comprises SEQ ID NO: 12; and (vi) light chain CDR3 comprises SEQ ID NO: 13. In some embodiments of the isolated antibodies, or the fragments or derivatives thereof, the heavy chain variable region comprises SEQ ID NO: 5 or is encoded by a nucleic acid molecule comprising SEQ ID NO: 4; and/or the light chain variable region comprises SEQ ID NO: 7 or is encoded by a nucleic acid molecule comprising SEQ ID NO: 6.

The presently disclosed subject matter also provides compositions comprising the presently disclosed antibodies, or the fragments or derivatives thereof, and one more pharmaceutically acceptable carriers and/or excipients. In some embodiments, the one or more pharmaceutically acceptable carriers and/or excipients are acceptable for use in a human.

The presently disclosed subject matter also provides compositions comprising the presently disclosed antibodies, or the fragments or derivatives thereof, conjugated to an active agent. In some embodiments, the active agent is selected from the group consisting of a radioactive molecule, a radionuclide, a sensitizer molecule, an imaging reagent, a radioisotope, a toxin, a cytotoxin, an anti-angiogenic agent, an anti-tumor agent, a chemotherapeutic agent, an immunomodulator, a cytokine, a reporter group, and combinations thereof. In some embodiments, the radioisotope is selected from the group consisting of $^{10}$B, $^{211}$At, $^{212}$Pb, $^{212}$Bi, $^{125}$I, $^{131}$I, $^{35}$S, and $^{3}$H. In some embodiments, immunomodulator is selected from the group consisting of an indoleamine 2,3-dioxygenase (IDO) inhibitor, optionally, 1-methyl-DL-tryptophan (1MT); an EP2/EP4 receptor antagonist; a cyclooxygenase inhibitor, optionally indomethacin; and a dendritic cell activator, optionally CpG oligodeoxynucleotides (CpG ODN).

The presently disclosed subject matter also provides kits comprising the presently disclosed antibodies, or the fragments or derivatives thereof. In some embodiments, the presently disclosed kits comprise instructions for use of the presently disclosed antibodies, or the fragments or derivatives thereof.

The presently disclosed subject matter also provides delivery vehicles for use in targeted delivery of active agents to tumor cells. In some embodiments, the delivery vehicles comprise one or more targeting agents that comprise the presently disclosed antibodies, or the fragments or derivatives thereof. In some embodiments, the active agent comprises a radioactive molecule, a radionuclide, a sensitizer molecule, an imaging reagent, a radioisotope, a toxin, a cytotoxin, an anti-angiogenic agent, an anti-tumor agent, a chemotherapeutic agent, an immunomodulator, a cytokine, a reporter group, or a combination thereof.

The presently disclosed subject matter also provides isolated cells that produce the presently disclosed antibodies, or the fragments or derivative thereof. In some embodiments, the isolated cell is a hybridoma that produces the presently disclosed antibodies. In some embodiments, the hybridoma is hybridoma cell line ATCC Accession No. PTA-11550 deposited with the American Type Culture Collection (ATCC), 10801 University Boulevard, Manassas, Va., 20110-2209, United States of America, on Dec. 16, 2010 under the terms of the Budapest Treaty.

The presently disclosed subject matter also provides methods for detecting the presence of an epitope to which monoclonal antibody TAB-004 binds in a biological sample. In some embodiments, the methods comprise: contacting the biological sample with one or more presently disclosed isolated antibodies, or fragments or derivatives thereof; and detecting the presence of an epitope to which monoclonal antibody TAB-004 binds in the biological sample. In some embodiments, the isolated antibodies, or the fragments or derivatives thereof, bind to an epitope that is present within a mucin (MUC1) polypeptide and/or an epitope that is present within a K-ras polypeptide, optionally a mutant K-ras polypeptide.

The presently disclosed subject matter also provides methods for making an antibody or a fragment or derivative thereof. In some embodiments, the methods comprise culturing an isolated cell of the presently disclosed subject matter or a hybridoma of the presently disclosed subject matter under conditions such that said antibody, the fragment, or the derivative thereof is expressed; and recovering the antibody or the fragment or derivative thereof from the cell or the hybridoma and/or from the environment in which the cell or the hybridoma is growing.

The presently disclosed subject matter also provides methods for detecting a tumor and/or a cancer cell in a subject. In some embodiments, the methods comprise contacting a biological sample in the subject or isolated from the subject with composition comprising a presently disclosed antibody, or a fragment or derivative thereof, under conditions sufficient for the presently disclosed antibody, or the fragment or derivative thereof, to bind to an epitope present on a tumor and/or a cancer cell, if present, in the biological sample; and detecting binding of the presently disclosed antibody, or the fragment or derivative thereof, to the epitope, wherein the detecting is indicative of a tumor and/or a cancer cell being present in the subject. In some embodiments, the tumor and/or the cancer cell is a tumor of the pancreas, breast, ovary, colon, or rectum, and/or a metastatic cell derived therefrom, which optionally expresses MUC1, a mutant K-ras, or both. In some embodiments, the presently disclosed antibody, or the fragment or derivative thereof, is conjugated to a detectable label comprising an imaging agent, which in some embodiments is selected from the group consisting of paramagnetic, radioactive, and fluorogenic ions. In some embodiments, the radioactive imaging agent is selected from the group consisting of gamma-emitters, positron-emitters and x-ray-emitters. In some embodiments, the radioactive imaging agent is selected from the group consisting of $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113}$In, $^{123}$I, $^{125}$I, $^{127}$Cs, $^{129}$Cs, $^{131}$I, $^{132}$I, $^{197}$Hg, $^{203}$Pb, and $^{206}$Bi. In some embodiments, the biological sample is a blood sample, or a fraction derived therefrom.

The presently disclosed subject matter also provides methods for treating a tumor in a subject. In some embodiments, the methods comprise administering to the subject a composition comprising a presently disclosed antibody, or a fragment or derivative thereof, conjugated to an active agent, whereby the active agent contacts the tumor to thereby treat the tumor. In some embodiments, the active agent comprises a therapeutic agent, optionally a chemotherapeutic agent, a toxin, a radiotherapeutic agent, or a combination thereof. In some embodiments, the chemotherapeutic agent is selected from the group consisting of an anti-tumor drug, a cytokine, an anti-metabolite, an alkylating agent, a hormone, methotrexate, doxorubicin, daunorubicin, cytosine arabinoside, etoposide, 5-fluorouracil, melphalan, chlorambucil, a nitrogen mustard, cyclophosphamide, cis-platinum, vindesine, vinca alkaloids, mitomycin, bleomycin, purothionin, macromomycin, 1,4-benzoquinone derivatives, trenimon, steroids, aminopterin, anthracyclines, demecolcine, etoposide, mithramycin, doxorubicin, daunomycin, vinblastine, neocarzinostatin, macromycin, α-amanitin, and combinations thereof. In some embodiments, the toxin is selected from the group consisting of Russell's Viper Venom, activated Factor IX, activated Factor X, thrombin, phospholipase C, cobra venom factor, ricin, ricin A chain, *Pseudomonas* exotoxin, diphtheria toxin, bovine pancreatic ribonuclease, pokeweed antiviral protein, abrin, abrin A chain, gelonin, saporin, modeccin, viscumin, volkensin, and combinations thereof. In some embodiments, the radiotherapeutic agent is selected from the group consisting of $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$Bi, $^{32}$P, $^{33}$P, $^{71}$Ge, $^{77}$As, $^{103}$Pb, $^{105}$Rn, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, and $^{197}$Hg.

The presently disclosed subject matter also provides methods for suppressing tumor growth in a subject. In some embodiments, the methods comprise administering to a subject bearing a tumor an effective amount of an isolated antibody, or a fragment or derivative thereof, comprising the complementarity determining regions (CDRs) of monoclonal antibody TAB-004. In some embodiments, the tumor is a tumor of the pancreas, breast, ovary, colon, or rectum, and/or a metastatic cell derived therefrom, which optionally expresses MUC1, a mutant K-ras, or both. In some embodiments, the CDRs of TAB-004 comprise one or more of the following: heavy chain CDR1 comprises SEQ ID NO: 8; heavy chain CDR2 comprises SEQ ID NO: 9; heavy chain CDR3 comprises SEQ ID NO: 10; light chain CDR1 comprises SEQ ID NO: 11; light chain CDR2 comprises SEQ ID NO: 12; and/or light chain CDR3 comprises SEQ ID NO: 13. In some embodiments, the heavy chain variable region comprises SEQ ID NO: 5 or is encoded by a nucleic acid molecule comprising SEQ ID NO: 4, and/or the light chain variable region comprises SEQ ID NO: 7 or is encoded by a nucleic acid molecule comprising SEQ ID NO: 6.

With respect to the treatment methods disclosed herein, in some embodiments the methods further comprise administering to the subject one or more additional anti-tumor treatments. In some embodiments, the one or more additional anti-tumor treatments are selected from the group consisting of radiotherapy, chemotherapy, an additional immunotherapy, an anti-inflammatory therapy, and combinations thereof. In some embodiments, the anti-inflammatory therapy comprises administering to the subject a cyclooxygenase inhibitor, optionally a cyclooxygenase-2-specific inhibitor. Isem the one or more additional anti-tumor therapies comprise administering gemcitabine (4-amino-1-(2-deoxy-2,2-difluoro-β-D-erythro-pentofuranosyl)pyrimidin-2(1H)-on-2',2'-difluoro-2'-deoxycytidine) and celecoxib (4-[5-(4-methylphenyl)-3-(trifluoromethyl)pyrazol-1-yl] benzenesulfonamide), or pharmaceutically acceptable salts of either or both thereof, to the subject.

The presently disclosed subject matter also provides methods for purifying cancer stem cells. In some embodiments, the methods comprise providing a population of cells suspected of comprising cancer stem cells; identifying a subpopulation of the cells that bind to an antibody, or a fragment or derivative thereof, comprising the CDRs of monoclonal antibody TAB-004; and purifying the subpopulation. In some embodiments, the population of cells comprises circulating cells isolated from a subject that has a tumor and/or a cancer. In some embodiments, the presently disclosed methods further comprise removing lineage-positive (lin$^+$) cells from the population of cells before the identifying step and/or after the purifying step.

The presently disclosed subject matter also provides methods for targeting active agents to circulating cancer stem cells in subjects. In some embodiments, the methods comprise contacting the circulating cancer stem cells with a composition comprising a presently disclosed antibody, or a fragment or derivative thereof, comprising the CDRs of monoclonal antibody TAB-004 and one or more active agents, optionally wherein the one or more active agents comprise a therapeutic agent, optionally a chemotherapeutic agent, a toxin, a radiotherapeutic agent, or a combination thereof. In some embodiments, the therapeutic agent comprises an immunomodulator, optionally wherein the immunomodulator is selected from the group consisting of wherein the immunomodulator is selected from the group consisting of an indoleamine 2,3-dioxygenase (IDO) inhibitor, optionally, 1-methyl-DL-tryptophan (1MT); an EP2/EP4 receptor antagonist; and a dendritic cell activator, optionally CpG oligodeoxynucleotides (CpG ODN).

The presently disclosed subject matter also provides methods for prognosing recurrence of cancer in a subject previously treated for the cancer. In some embodiments, the methods comprise isolating a biological sample comprising circulating cells from a subject with a cancer; contacting the biological sample with the presently disclosed antibodies, or the fragments or derivatives thereof, under conditions sufficient for the antibodies, or the fragments or derivatives thereof, to bind to an epitope present on a tumor and/or a cancer cell, if present, in the biological sample; and identifying in the biological sample one or more circulating cells that bind to the antibody, or the fragment or derivative thereof, whereby recurrence of a cancer is prognosed in the subject. In some embodiments, the biological sample comprises a blood sample, a lymph sample, or a fraction thereof. In some embodiments, the cancer is a pancreatic cancer or a breast cancer. In some embodiments, the antibodies, or the fragments or derivatives thereof, are selected from the group consisting of monoclonal antibodies produced by hybridoma cell line TAB-004 deposited with the American Type Culture Collection (ATCC), 10801 University Boulevard, Manassas, Va., 20110-2209, United States of America, on Dec. 16, 2010 under the terms of the Budapest Treaty, as Accession No. PTA-11550; chimeric antibodies, or fragments or derivatives thereof; humanized antibodies, or fragments or derivatives thereof; human antibodies, or fragments or derivatives thereof; single chain antibodies, or fragments or derivatives thereof; and Fab fragments, and further wherein the chimeric antibodies, the humanized antibodies, the human antibodies, the single chain antibodies, or the Fab fragments comprise the complementarity determining regions (CDRs) of monoclonal antibody TAB-004. In some embodiments, the CDRs of monoclonal antibody TAB-004 comprise the following amino acid sequences: heavy chain CDR1 comprises SEQ ID NO: 8; heavy chain CDR2 comprises SEQ ID NO: 9; heavy chain CDR3 comprises SEQ ID NO: 10; light chain CDR1 comprises SEQ ID NO: 11; light chain CDR2 comprises SEQ ID NO: 12; and light chain CDR3 comprises SEQ ID NO: 13. In some embodiments, the heavy chain variable region comprises SEQ ID NO: 5 or is encoded by a nucleic acid molecule comprising SEQ ID NO: 4; and/or the light chain variable region comprises SEQ ID NO: 7 or is encoded by a nucleic acid molecule comprising SEQ ID NO: 6.

The presently disclosed subject matter also provides methods for prognosing progression of a cancer in a subject. In some embodiments, the methods comprise isolating a biological sample comprising circulating cells from a subject with a cancer; contacting the biological sample with an antibody, or a fragment or derivative thereof, of the presently disclosed subject matter under conditions sufficient for the antibody, or the fragment or derivative thereof, to bind to an epitope present on a tumor and/or a cancer cell, if present, in the biological sample; and identifying in the biological sample one or more circulating cells that bind to the antibody, or the fragment or derivative thereof, whereby progression of a cancer is prognosed in the subject. In some embodiments, the biological sample comprises a blood sample, a lymph sample, or a fraction thereof. In some embodiments, the cancer is a pancreatic cancer or a breast cancer. In some embodiments, the antibody, or the fragment or derivative thereof, is selected from the group consisting of a monoclonal antibody produced by hybridoma cell line TAB-004 deposited with the American Type Culture Collection (ATCC), 10801 University Boulevard, Manassas, Va., 20110-2209, United States of America, on Dec. 16, 2010 under the terms of the Budapest Treaty as Accession No. PTA-11550 on Dec. 16, 2010; a chimeric antibody, or a fragment or derivative thereof; a humanized antibody, or a fragment or derivative thereof; a human antibody, or a fragment or derivative thereof; a single chain antibody, or a fragment or derivative thereof; and a Fab fragment, and further wherein the chimeric antibody, the humanized antibody, the human antibody, the single chain antibody, or the Fab fragment comprises the complementarity determining regions (CDRs) of monoclonal antibody TAB-004. In some embodiments, the CDRs of monoclonal antibody TAB-004 comprise the following amino acid sequences: heavy chain CDR1 comprises SEQ ID NO: 8; heavy chain CDR2 comprises SEQ ID NO: 9; heavy chain CDR3 comprises SEQ ID NO: 10; light chain CDR1 comprises SEQ ID NO: 11; light chain CDR2 comprises SEQ ID NO: 12; and light chain CDR3 comprises SEQ ID NO: 13. In some embodiments, the heavy chain variable region comprises SEQ ID NO: 5 or is encoded by a nucleic acid molecule comprising SEQ ID NO: 4; and/or the light chain variable region comprises SEQ ID NO: 7 or is encoded by a nucleic acid molecule comprising SEQ ID NO: 6. In some embodiments, progression of the cancer comprises metastasis of the cancer in the subject.

The presently disclosed subject matter also provides isolated nucleic acid molecules comprising any of SEQ ID ID NOs: 4 and 6, and/or encoding any of SEQ ID NOs: 5 and 7-13. In some embodiments, the isolated nucleic acid molecule is present within a vector, which in some embodiments is an expression vector. In some embodiments, the isolated nucleic acid molecule is present within an expression vector operably linked to one or more additional nucleotide sequences encoding subsequences of antibody molecules such that upon introduction of the expression vector into an appropriate host, an intact recombinant antibody comprising one or more of SEQ ID NOs: 5 and 7-13, or a fragment or derivative thereof, is expressed by the host cell.

Thus, it is an object of the presently disclosed subject matter to provide isolated antibodies, and fragments and derivatives thereof, which bind to antigens present in tumors.

An object of the presently disclosed subject matter having been stated hereinabove, and which is achieved in whole or in part by the compositions and methods disclosed herein, other objects will become evident as the description proceeds when taken in connection with the accompanying Figures as best described herein below.

BRIEF DESCRIPTION OF THE DRAWINGS

FIG. 1A is a series of photomicrographs depicting the binding of the exemplary antibody to human tumors at Stages 0 (normal pancreatic tissue as a negative control) and 2-4.

FIG. 1B is a series of photomicrographs depicting the binding of an exemplary antibody of the presently disclosed subject matter to spontaneous tumors present in the pancreas of 6, 16, 26, and 34 week old transgenic mice that carried a human MUC1 transgene and a K-ras$^{G12D}$ mutation.

FIG. 4A is a line graph showing that the exemplary TAB-004 antibody enhanced specific lysis of KCM tumor cells at various effector (NK cells) to target ratios (E:T ratio) relative to a negative control (minus TAB-004 antibody).

FIG. 4B is a bar graph showing that conjugation of the exemplary TAB-004 antibody to CpG ODN further enhanced specific lysis of tumor cells at various E:T ratios relative to the unconjugated antibody.

FIG. 5A is a line graph showing the measured tumor volumes (in mm measured by digital calipers) in mice treated with phosphate-buffered saline (PBS) alone (negative control; filled squares), CpG ODN alone (X's), the unconjugated TAB-004 antibody (open circles), or the TAB-004-CpG ODN conjugate (filled circles).

FIG. 5B is a bar graph showing the changes in tumor volumes in mice at 19 and 27 days after the final treatment was administered. Of note is the observation that at 19 and 27 days post-treatment, the tumor volumes in the mice treated with TAB-004-CpG ODN had not increased as compared to the control mice (i.e., PBS alone, CpG ODN alone, or TAB-004 alone). *: $p<0.5$. PBS alone (negative control; white bars); CpG ODN alone (hatched bars); unconjugated TAB-004 antibody (black bars); TAB-004-CpG ODN conjugate (cross-hatched bars).

FIG. 8A is a scatter plot showing the distributions of cells in the absence of either antibody. FIG. 8B is a scatter plot showing the distributions of cells stained with an isotype control. FIG. 8C is a series of scatter plots showing the distributions of cells in normal tissue stained with the TAB-004 antibody versus a CXCR4 antibody. FIG. 8D is a series of scatter plots showing the distributions of cells in pancreatic adenocarcinoma tissue stained with the TAB-004 antibody versus a CXCR4 antibody.

In FIG. 9A, PANC1 pancreatic cancer cell line cells were detected by the TAB-004-PE antibody. In FIGS. 9B and 9C, circulating tumor cells present in the blood from two patients (patient number 1 and patient number 2, respectively) were detected by the TAB-004-PE antibody (see the right most black line in FIG. 9B and the right most black and light gray lines in FIG. 9C) but not the EpCAM-PE antibody (see the light gray lines in FIGS. 9B and 9C) that is currently in use.

BRIEF DESCRIPTION OF THE SEQUENCE LISTING

Figure 1A:
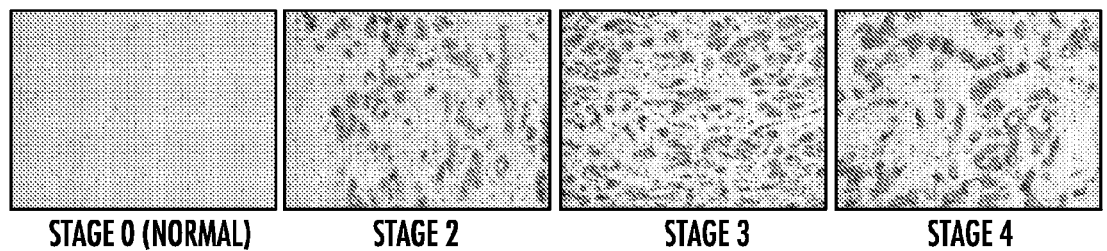
FIGS. 1A and 1B are a series of photomicrographs depicting specific binding of an exemplary antibody of the presently disclosed subject matter to human and mouse pancreatic tumors. The dark staining in the panels is indicative of positive binding of the exemplary antibody to cells present in the sample.

SEQ ID NO: 1 is an amino acid sequence of a human MUC1 gene product. It corresponds to GENBANK® Accession No. AAA60019.

SEQ ID NO: 2 is an amino acid sequence of a human K-ras oncogene product. It corresponds to GENBANK® Accession No. NP_004976.

SEQ ID NO: 3 is an amino acid sequence of peptide to which the TAB-004 antibody disclosed herein can bind in an ELISA assay. The peptide thus includes an epitope to which the TAB-004 antibody binds specifically.

SEQ ID NOs: 4 and 5 are the nucleotide and encoded amino acid sequences, respectively, of the heavy chain of the TAB-004 antibody disclosed herein.

SEQ ID NOs: 6 and 7 are the nucleotide and encoded amino acid sequences, respectively, of the light chain of the TAB-004 antibody disclosed herein.

SEQ ID NOs: 8-10 are the amino acid sequences of CDR1, CDR2, and CDR3, respectively, of the heavy chain of the TAB-004 antibody disclosed herein.

SEQ ID NOs: 11-13 are the amino acid sequences of CDR1, CDR2, and CDR3, respectively, of the light chain of the TAB-004 antibody disclosed herein.

DETAILED DESCRIPTION

The presently disclosed subject matter will be now be described more fully hereinafter with reference to the accompanying Figures and EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

I. Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the presently disclosed and claimed subject matter.

Following long-standing patent law convention, the terms "a", "an", and "the" refer to "one or more" when used in this application, including in the claims. For example, the phrase "an antibody" refers to one or more antibodies, including a plurality of the same antibody. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration, or percentage, is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the disclosed compositions. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. It is noted that, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, a pharmaceutical composition can "consist essentially of" a pharmaceutically active agent or a plurality of pharmaceutically active agents, which means that the recited pharmaceutically active agent(s) is/are the only pharmaceutically active agent(s) present in the pharmaceutical composition. It is noted, however, that carriers, excipients, and/or other inactive agents can and likely would be present in such a pharmaceutical composition.

With respect to the terms "comprising", "consisting of", and "consisting essentially of", where one of these three terms is used herein, the presently disclosed and claimed subject matter can include the use of either of the other two terms. For example, in some embodiments, the presently disclosed subject matter relates to compositions comprising antibodies. It would be understood by one of ordinary skill in the art after review of the instant disclosure that the presently disclosed subject matter thus encompasses compositions that consist essentially of the antibodies of the presently disclosed subject matter, as well as compositions that consist of the antibodies of the presently disclosed subject matter.

The term "subject" as used herein refers to a member of any invertebrate or vertebrate species. Accordingly, the term "subject" is intended to encompass in some embodiments any member of the Kingdom Animalia including, but not limited to the phylum Chordata (e.g., members of Classes Osteichythyes (bony fish), Amphibia (amphibians), Reptilia (reptiles), Ayes (birds), and Mammalia (mammals), and all Orders and Families encompassed therein.

The compositions and methods of the presently disclosed subject matter are particularly useful for warm-blooded vertebrates. Thus, in some embodiments the presently disclosed subject matter concerns mammals and birds. More particularly provided are compositions and methods derived from and/or for use in mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also provided is the use of the disclosed methods and compositions on livestock, including but not limited to domesticated swine (pigs and hogs), ruminants, horses, poultry, and the like.

Similarly, all genes, gene names, and gene products disclosed herein are intended to correspond to homologs and/or orthologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes presented in GEN-BANK® Accession Nos: AAA60019 and NP_004976, the human amino acid sequences disclosed are intended to encompass homologous genes and gene products from other animals including, but not limited to other mammals, fish, amphibians, reptiles, and birds. Also encompassed are any and all nucleotide sequences that encode the disclosed amino acid sequences, including but not limited to those disclosed in the corresponding GENBANK® entries (i.e., J05582.1 and NM_004985, respectively).

The terms "cancer" and "tumor" are used interchangeably herein and can refer to both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder, and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). As used herein, the terms "cancer" and "tumor" are also intended to refer to multicellular tumors as well as individual neoplastic or pre-neoplastic cells. In some embodiments, a cancer or a tumor comprises a cancer or tumor of an epithelial tissue such as, but not limited to a carcinoma. In some embodiments, a tumor is an adenocarcinoma, which in some embodiments is an adenocarcinoma of the pancreas, breast, ovary, colon, or rectum, and/or a metastatic cell derived therefrom.

As used herein in the context of molecules, the term "effector" refers to any molecule or combination of molecules whose activity it is desired to deliver/into and/or localize at a cell. Effectors include, but are not limited to labels, cytotoxins, enzymes, growth factors, transcription factors, drugs, etc.

As used herein in the context of cells of the immune system, the term "effector" refers to an immune system cell that can be induced to perform a specific function associated with an immune response to a stimulus. Exemplary effector cells include, but are not limited to natural killer (NK) cells and cytotoxic T cells ($T_c$ cells).

As used herein, the term "expression vector" refers to a DNA sequence capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression. In some embodiments, the expression vector comprises an isolated nucleic acid molecule of the presently disclosed subject matter, which in some embodiments comprises any of SEQ ID ID NOs: 4 and 6, or encodes any of SEQ ID NOs: 5 and 7-13. In some embodiments, the isolated nucleic acid molecule present within an expression vector is operably linked to one or more additional nucleotide sequences encoding subsequences of antibody molecules such that upon introduction of the expression vector into an appropriate host, an intact recombinant antibody comprising one or more of SEQ ID NOs: 5 and 7-13, or a fragment or derivative thereof, is expressed by the host cell.

As used herein, the term "hybridoma" refers to a cell or cell line that is produced in the laboratory from the fusion of an antibody-producing lymphocyte and a non-antibody-producing cancer cell, usually a myeloma or lymphoma cell. As would be known to those of one of ordinary skill in the art, a hybridoma can proliferate and produce a continuous supply of a specific monoclonal antibody. Methods for generating hybridomas are known in the art (see e.g., Harlow & Lane, 1988).

As used herein, the terms "operatively linked" and "operably linked" refer to transcriptional regulatory elements (such as, but not limited to promoter sequences, transcription terminator sequences, etc.) that are connected to a nucleotide sequence (for example, a coding sequence or open reading frame) in such a way that the transcription of the nucleotide sequence is controlled and regulated by that transcriptional regulatory element. Similarly, a nucleotide sequence is said to be under the "transcriptional control" of a promoter to which it is operably linked. Techniques for operatively linking a promoter region to a nucleotide sequence are known in the art.

As used herein, the term "prodrug" refers to an analog and/or a precursor of a drug (e.g., a cytotoxic agent) that substantially lacks the biological activity of the drug (e.g., a cytotoxic activity) until subjected to an activation step. Activation steps can include enzymatic cleavage, chemical activation steps such as exposure to a reductant, and/or physical activation steps such as photolysis. In some embodiments, activiation occurs in vivo within the body of a subject.

II. Antibodies, and Fragments and Derivatives Thereof, and Methods of Producing the Same II.A. Generally The presently disclosed subject matter provides in some embodiments isolated antibodies, as well as fragments and derivatives thereof, which bind to antigens present within tumors such as, but not limited to antigens present within MUC1 polypeptides.

As used herein, the terms "antibody" and "antibodies" refer to proteins comprising one or more polypeptides substantially encoded by immunoglobulin genes or fragments of immunoglobulin genes. Immunoglobulin genes typically include the kappa (κ), lambda (λ), alpha (α), gamma (γ), delta (δ), epsilon (ε), and mu (μ) constant region genes, as well as myriad immunoglobulin variable region genes. Light chains are classified as either κ or λ. In mammals, heavy chains are classified as γ, μ, α, δ, or ε, which in turn define the immunoglobulin classes, IgG, IgM, IgA, IgD, and IgE, respectively. Other species have other light and heavy chain genes (e.g., certain avians produced what is referred to as IgY, which is an immunoglobulin type that hens deposit in the yolks of their eggs), which are similarly encompassed by the presently disclosed subject matter. In some embodiments, the term "antibody" refers to an antibody that binds specifically to an epitope that is present on a tumor antigen including, but not limited to a MUC1 polypeptide and/or a mutant K-ras polypeptide. In some embodiments, the term "antibody" refers to an antibody that binds specifically to an epitope present within any of SEQ ID NOs: 1-3.

A typical immunoglobulin (antibody) structural unit is known to comprise a tetramer. Each tetramer is composed of two identical pairs of polypeptide chains, each pair having one "light" chain (average molecular weight of about 25 kiloDalton (kDa)) and one "heavy" chain (average molecular weight of about 50-70 kDa). The two identical pairs of polypeptide chains are held together in dimeric form by disulfide bonds that are present within the heavy chain region. The N-terminus of each chain defines a variable region of about 100 to 110 or more amino acids primarily responsible for antigen recognition (sometimes referred to as the "paratope"). The terms variable light chain ($V_L$) and variable heavy chain ($V_H$) refer to these light and heavy chains, respectively.

Antibodies typically exist as intact immunoglobulins or as a number of well-characterized fragments that can be produced by digestion with various peptidases. For example, digestion of an antibody molecule with papain cleaves the antibody at a position N-terminal to the disulfide bonds. This produces three fragments: two identical "Fab" fragments, which have a light chain and the N-terminus of the heavy chain, and an "Fc" fragment that includes the C-terminus of the heavy chains held together by the disulfide bonds. Pepsin, on the other hand, digests an antibody C-terminal to the disulfide bond in the hinge region to produce a fragment known as the "F(ab)'$_2$" fragment, which is a dimer of the Fab fragments joined by the disulfide bond. The F(ab)'$_2$ fragment can be reduced under mild conditions to break the disulfide linkage in the hinge region, thereby converting the F(ab')$_2$ dimer into two "Fab'" monomers. The Fab' monomer is essentially an Fab fragment with part of the hinge region (see e.g., Paul, 1993, for a more detailed description of other antibody fragments). With respect to these various fragments, Fab, F(ab')$_2$, and Fab' fragments include at least one intact antigen binding domain (paratope), and thus are capable of binding to antigens.

While various antibody fragments are defined in terms of the digestion of an intact antibody, one of skill will appreciate that various of these fragments (including, but not limited to Fab' fragments) can be synthesized de novo either chemically or by utilizing recombinant DNA methodology. Thus, the term "antibody" as used herein also includes antibody fragments produced by the modification of whole antibodies and/or synthesized de novo using recombinant DNA methodologies. In some embodiments, the term "antibody" comprises a fragment that has at least one antigen binding domain (paratope).

Antibodies can be polyclonal or monoclonal. As used herein, the term "polyclonal" refers to antibodies that are present together in a given collection of antibodies and that are derived from different antibody-producing cells (e.g., B cells). Exemplary polyclonal antibodies include, but are not limited to those antibodies that bind to a particular antigen and that are found in the blood of an animal after that animal has produced an immune response against the antigen. However, it is understood that a polyclonal preparation of antibodies can also be prepared artificially by mixing at least non-identical two antibodies. Thus, polyclonal antibodies typically include different antibodies that are directed against (i.e., bind to) the same and/or different epitopes (sometimes referred to as an "antigenic determinant" or just "determinant") of any given antigen.

As used herein, the term "monoclonal" refers to a single antibody species and/or a substantially homogeneous population of a single antibody species. Stated another way, "monoclonal" refers to individual antibodies or populations of individual antibodies in which the antibodies are identical in specificity and affinity except for possible naturally occurring mutations that can be present in minor amounts. Typically, a monoclonal antibody (mAb or moAb) is generated by a single B cell or a progeny cell thereof (although the presently disclosed subject matter also encompasses "monoclonal" antibodies that are produced by molecular biological techniques as described herein). Monoclonal antibodies (mAbs or moAbs) are highly specific, typically being directed against a single antigenic site. Furthermore, in contrast to polyclonal antibody preparations, a given mAb is typically directed against a single epitope on the antigen.

In addition to their specificity, mAbs can be advantageous for some purposes in that they can be synthesized uncontaminated by other antibodies. The modifier "monoclonal" is not to be construed as requiring production of the antibody by any particular method, however. For example, in some embodiments, the mAbs of the presently disclosed subject matter are prepared using the hybridoma methodology first described by Kohler et al., 1975, and in some embodiments are made using recombinant DNA methods in prokaryotic or eukaryotic cells (see e.g., U.S. Pat. No. 4,816,567, the entire contents of which are incorporated herein by reference). mAbs can also be isolated from phage antibody libraries using the techniques described in, for example, Clackson et al., 1991 and Marks et al., 1991.

The antibodies, fragments, and derivatives of the presently disclosed subject matter can also include chimeric antibodies. As used herein in the context of antibodies, the term "chimeric", and grammatical variants thereof, refers to antibody derivatives that have constant regions derived substantially or exclusively from antibody constant regions from one species and variable regions derived substantially or exclusively from the sequence of the variable region from another species.

The variable region allows an antibody to selectively recognize and specifically bind epitopes on antigens. That is, the $V_L$ domain and $V_H$ domain, or subsets of the complementarity determining regions (CDRs) within these variable domains, of an antibody combine to form the variable region that defines a three dimensional antigen binding site. This quaternary antibody structure forms the antigen binding site present at the end of each arm of the antibody. More specifically, the antigen binding site is defined by three CDRs on each of the $V_H$ and $V_L$ chains. In some instances (e.g., certain immunoglobulin molecules derived from camelid species or engineered based on camelid immunoglobulins), a complete immunoglobulin molecule can consist of heavy chains only with no light chains (see e.g., Hamers-Casterman et al., 1993).

In naturally occurring antibodies, there are six CDRs present in each antigen binding domain that are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see e.g., Chothia & Lesk, 1987; Kabat et al., 1991; Martin, 1996; Johnson & Wu, 2000).

A particular kind of chimeric antibody is a "humanized" antibody, in which the antibodies are produced by substituting the CDRs of, for example, a mouse antibody, for the CDRs of a human antibody (see e.g., PCT International Patent Application Publication No. WO 1992/22653). Thus, in some embodiments, a humanized antibody has constant regions and variable regions other than the CDRs that are derived substantially or exclusively from the corresponding regions of a human antibody, and CDRs that are derived substantially or exclusively from a mammal other than a human.

The antibodies, fragments, and derivatives of the presently disclosed subject matter can also be single chain antibodies and single chain antibody fragments. Single-chain antibody fragments contain amino acid sequences having at least one of the variable regions and/or CDRs of the whole antibodies described herein, but are lacking some or all of the constant domains of those antibodies. These constant domains are not necessary for antigen binding, but constitute a major portion of the structure of whole antibodies.

Single-chain antibody fragments can overcome some of the problems associated with the use of antibodies containing a part or all of a constant domain. For example, single-chain antibody fragments tend to be free of undesired interactions between biological molecules and the heavy-chain constant region, and/or other unwanted biological activities. Additionally, single-chain antibody fragments are considerably smaller than whole antibodies and can therefore be characterized by greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely than whole antibodies to provoke an immune response in a recipient. The single-chain antibody fragments of the presently disclosed subject matter include, but are not limited to single chain fragment variable (scFv) antibodies and derivatives thereof such as, but not limited to tandem di-scFv, tandem tri-scFv, diabodies, triabodies, tetrabodies, miniantibodies, and minibodies.

Fv fragments correspond to the variable fragments at the N-termini of immunoglobulin heavy and light chains. Fv fragments appear to have lower interaction energy of their two chains than Fab fragments. To stabilize the association of the $V_H$ and $V_L$ domains, they can be linked with peptides (see e.g., Bird et al., 1988; Huston et al., 1988), disulfide bridges (see e.g., Glockshuber et al., 1990), and/or "knob in hole" mutations (see e.g., Zhu et al., 1997). ScFv fragments can be produced by methods well known to those skilled in the art (see e.g., Whitlow et al., 1991; Huston et al., 1993).

scFv can be produced in bacterial cells such as *E. coli* or in eukaryotic cells. One potential disadvantage of scFv is the monovalency of the product, which can preclude an increased avidity due to polyvalent binding, and their short half-life. Attempts to overcome these problems include bivalent $(scFv')_2$ produced from scFv containing an additional C-terminal cysteine by chemical coupling (see e.g., Adams et al., 1993; McCartney et al., 1995) or by spontaneous site-specific dimerization of scFv containing an unpaired C-terminal cysteine residue (see e.g., Kipriyanov et al., 1995).

Alternatively, scFv can be forced to form multimers by shortening the peptide linker to 3 to 12 residues to form "diabodies" (see e.g., Holliger et al., 1993). Reducing the linker still further can result in scFv trimers ("triabodies"; see e.g., Kortt et al., 1997) and tetramers ("tetrabodies"; see e.g., Le Gall et al., 1999). Construction of bivalent scFv molecules can also be achieved by genetic fusion with protein dimerizing motifs to form "miniantibodies" (see e.g., Pack et al., 1992) and "minibodies" (see e.g., Hu et al., 1996). scFv-scFv tandems ($(scFv)_2$) can be produced by linking two scFv units by a third peptide linker (see e.g., Kurucz et al., 1995).

Bispecific diabodies can be produced through the non-covalent association of two single chain fusion products consisting of $V_H$ domain from one antibody connected by a short linker to the $V_L$ domain of another antibody (see e.g., Kipriyanov et al., 1998). The stability of such bispecific diabodies can be enhanced by the introduction of disulfide bridges or "knob in hole" mutations as described hereinabove or by the formation of single chain diabodies (scDb) wherein two hybrid scFv fragments are connected through a peptide linker (see e.g., Kontermann et al., 1999).

Tetravalent bispecific molecules can be produced, for example, by fusing an scFv fragment to the $CH_3$ domain of an IgG molecule or to a Fab fragment through the hinge region (see e.g., Coloma et al., 1997). Alternatively, tetravalent bispecific molecules have been created by the fusion of bispecific single chain diabodies (see e.g., Alt et al., 1999). Smaller tetravalent bispecific molecules can also be formed by the dimerization of either scFv-scFv tandems with a linker containing a helix-loop-helix motif (DiBi miniantibodies; see e.g., Muller et al., 1998) or a single chain molecule comprising four antibody variable domains ($V_H$ and $V_L$) in an orientation preventing intramolecular pairing (tandem diabody; see e.g., Kipriyanov et al., 1999).

Bispecific $F(ab')_2$ fragments can be created by chemical coupling of Fab' fragments or by heterodimerization through leucine zippers (see e.g., Shalaby et al., 1992; Kostelny et al., 1992). Also available are isolated $V_H$ and $V_L$ domains (see U.S. Pat. Nos. 6,172,197; 6,248,516; and 6,291,158).

The presently disclosed subject matter also includes functional equivalents of the antibodies of the presently disclosed subject matter. As used herein, the phrase "functional equivalent" as it refers to an antibody refers to a molecule that has binding characteristics that are comparable to those of a given antibody. In some embodiments, chimerized, humanized, and single chain antibodies, as well as fragments thereof, are considered functional equivalents of the corresponding antibodies upon which they are based. In some embodiments, the presently disclosed subject matter provides functional equivalents of the TAB-004 mAb disclosed herein.

Functional equivalents also include polypeptides with amino acid sequences substantially the same as the amino acid sequence of the variable or hypervariable regions of the antibodies of the presently disclosed subject matter. As used herein with respect to nucleic acid and/or amino acid sequences, the phrase "substantially the same" refers to a biosequence with in some embodiments at least 80%, in some embodiments at least 85%, in some embodiments at least about 90%, in some embodiments at least 91%, in some embodiments at least 92%, in some embodiments at least 93%, in some embodiments at least 94%, in some embodiments at least 95%, in some embodiments at least 96%, in some embodiments at least 97%, in some embodiments at least 98%, and in some embodiments at least about 99% sequence identity to another nucleic acid and/or amino acid sequence, as determined by the FASTA search method in accordance with Pearson & Lipman, 1988. In some embodiments, the percent identity calculation is performed over the full length of the nucleic acid and/or amino acid sequence of an antibody of the presently disclosed subject matter.

In some embodiments, a functional equivalent of a nucleotide sequence is a sequence that encodes the same amino acid sequence (i.e., that include one or more functionally equivalent codons). A listing of functionally equivalent codons is presented in Table 1.

TABLE 1

Functionally Equivalent Codons

| Amino Acid | Codons |
| --- | --- |
| Alanine (Ala or A) | GCA; GCC; GCG; GCU |
| Cysteine (Cys or C) | UGC; UGU |
| Aspartic Acid (Asp or D) | GAC; GAU |
| Glumatic acid (Glu or E) | GAA; GAG |
| Phenylalanine (Phe or F) | UUC; UUU |
| Glycine (Gly or G) | GGA; GGC; GGG; GGU |
| Histidine (His or H) | CAC; CAU |
| Isoleucine (Ile or I) | AUA; AUC; AUU |
| Lysine (Lys or K) | AAA; AAG |
| Methionine (Met or M) | AUG |
| Asparagine (Asn or N) | AAC; AAU |
| Proline (Pro or P) | CCA; CCC; CCG; CCU |
| Glutamine (Gln or Q) | CAA; CAG |
| Threonine (Thr or T) | ACA; ACC; ACG; ACU |
| Valine (Val or V) | GUA; GUC; GUG; GUU |
| Tryptophan (Trp or W) | UGG |
| Tyrosine (Tyr or Y) | UAC; UAU |
| Leucine (Leu or L) | UUA; UUG; CUA; CUC; CUG; CUU |
| Arginine (Arg or R) | AGA; AGG; CGA; CGC; CGG; CGU |
| Serine)Ser or S) | ACG; AGU; UCA; UCC; UCG; UCU |

In some embodiments, a functional equivalent of a given amino acid sequence is an amino acid with one or more conservative amino acid substitutions. Conservative amino acid substitution refers to the substitution of one amino acid for another amino acid of the same class (e.g., valine for glycine, or arginine for lysine). Polypeptides that are functionally equivalent to prouroguanylin and/or prouroguanylin fragments can be made using random mutagenesis on the encoding nucleic acids by techniques well known to those having ordinary skill in the art. It is more likely, however, that such polypeptides will be generated by site-directed mutagenesis (again using techniques well known to those having ordinary skill in the art). These polypeptides can have increased functionality or decreased functionality.

Functional equivalents can also include fragments of antibodies that have the same or comparable binding characteristics to those of a whole antibody of the presently disclosed subject matter. Such fragments can contain one or both Fab fragments, the F(ab')$_2$ fragment, the F(ab') fragment, an Fv fragment, or any other fragment that includes at least one antigen binding domain. In some embodiments, the antibody fragments contain all six CDRs of a whole antibody of the presently disclosed subject matter (e.g., comprise CDRs comprising each of SEQ ID NOs: 8-13), although fragments containing fewer than all of such regions, such as three, four, or five CDRs, can also be functional equivalents as defined herein. Further, functional equivalents can be or can combine members of any one of the following immunoglobulin classes: IgG, IgM, IgA, IgD, and IgE, and the subclasses thereof, as well as other subclasses as might be appropriate for non-mammalian subjects (e.g., IgY for chickens and other avian species).

Functional equivalents also include aptamers and other non-antibody molecules, provided that such molecules have the same or comparable binding characteristics to those of a whole antibody of the presently disclosed subject matter.

In some embodiments, the antibodies, fragments, and derivatives thereof are selected from the group consisting of monoclonal antibody TAB-004 produced by hybridoma cell line ATCC No. PTA-11550, as well as chimeric antibodies or fragments or derivatives thereof, humanized antibodies or fragments or derivatives thereof, single chain antibodies or fragments or derivatives thereof, Fab fragments thereof, F(ab')$_2$ fragments thereof, Fv fragments thereof, and Fab' fragments thereof. In some embodiments, the antibodies, fragments, and derivatives of the presently disclosed subject matter have the binding characteristics of monoclonal antibody TAB-004. In some embodiments, the antibodies, fragments, and derivatives of the presently disclosed subject matter have at least some and in some cases all of the binding characteristics of monoclonal antibody TAB-004. In some embodiments, the antibodies, fragments, and derivatives of the presently disclosed subject matter bind to an epitope present within any of SEQ ID NOs: 1-3, in some embodiments an epitope present within SEQ ID NO: 3.

As used herein, the term "TAB-004" refers to a mAb that is produced by a hybridoma cell line designated "TAB-004" and that was deposited with the American Type Culture Collection (ATCC), 10801 University Boulevard, Manassas, Va., 20110-2209, United States of America, on Dec. 16, 2010 under Accession No. PTA-11550 pursuant to the terms of the Budapest Treaty. TAB-004 is a mAb of the IgG isotype that has been found to bind to an epitope present on a human mucin-1 (MUC1) polypeptide. More particularly, in some embodiments TAB-004 can bind to an epitope present within SEQ ID NO: 3. TAB-004 itself comprises the CDR sequences disclosed in SEQ ID NOs. 8-13.

As used herein, the term "MUC1" refers to a molecule defined as follows. MUC1 is one of the epithelial mucin family of molecules. MUC1 is widely expressed on a large number of epithelial cancers and is aberrantly glycosylated making it structurally and antigenically distinct from that expressed by non-malignant cells (see e.g., Barratt-Boyes, 1996; Price et al., 1998; Peterson et al., 1991). The dominant form of MUC1 is a high molecular weight molecule comprised of a large highly immunogenic extracellular mucin-like domain with a large number of twenty amino acid tandem repeats, a transmembrane region, and a cytoplasmic tail (Quin et al., 2000; McGucken et al., 1995; Dong et al., 1997).

MUC1 is overexpressed and aberrantly glycosylated in most epithelial adenocarcinomas including breast and pancreas. Adenocarcinoma of the breast and pancreas not only overexpress MUC1 but also shed MUC1 into the circulation. High MUC1 serum levels are associated with progressive disease. MUC1 has been exploited as a prospective biomarker because of the complex and heterogeneous nature of the epitopes expressed within the antigen. MUC1 synthesized by cancerous tissues usually displays an aberrant oligosaccharide profile, which gave rise to the expression of neomarkers such as sialyl-Lea (assayed in the CA19-9 test), sialyl-Lex, and sialyl-Tn (TAG-72), as well as the cryptic epitopes such as Tn.

In addition, because of underglycosylation, the peptide core of the mucin becomes exposed such that epitopes within the core that is not accessible within normal tissue-derived MUC1 might serve as potential biomarkers. Thus, differences between normal versus malignant tissue can provide for distinct epitopes that can show higher specificity for malignant tissues. Currently, tests for several of these epitopes are available in commercial form for use in patient management including CA15-3 (Abbott Laboratories, Abbott Park, Ill., United States of America), CA 27-29 (Bayer Diagnostics, Tarrytown, N.Y., United States of America), and CA19-9 (Panomics Inc, Redwood City, Calif., United States of America).

Thus far, none have proven to be of particular diagnostic value, probably due at least in part to low specificity as shown in Table 2.

TABLE 2

Assays Employed to Assess Overexpression of MUC1 in Various Tissues*

| Assay | Cancers in which MUC1 is Overexpressed | Non-cancerous Conditions in which MUC1 is Overexpressed |
|---|---|---|
| CA 15-5 | Breast, lung, ovarian, endometrial, bladder, pancreas, gastrointestinal | liver disease (cirrhosis, hepatitis), lupus, sarcoid, tuberculosis, non-cancerous breast lesions |
| CA 19-9 | Pancreas, colorectal, liver, stomach and biliary tree cancers | pancreatitis, ulcerative colitis, inflammatory bowel disease, inflammation or blockage of the bile duct |
| CA 27-29 | Breast, colon, gastric, liver, lung, pancreatic, ovarian, prostate cancers | ovarian cysts, liver and kidney disorders, non-cancerous breast problems |

*adapted from Perkins et al., 3002.

Recently, another MUC1 antibody known as PAM4 has gained attention for use in pancreatic cancer diagnosis due to its high sensitivity and specificity for pancreatic cancer but not any other epithelial cancers such as breast and ovarian cancers (Gold et al., 2007).

In normal epithelial tissue, MUC1 is localized to the apical region of the cells. Malignant transformation results in upregulation of MUC1 by gene amplification and/or increased transcriptional activation and the distribution of MUC1 on the cell surface is no longer confined to the apical region (Bieche & Lidereau, 1997). While the function of MUC1 still awaits clarification, high cytoplasmic expression of MUC1 has been associated with poor prognosis in patients with breast and/or ovarian cancers.

MUC1 has also been demonstrated to play a role in cell adhesion, cell signaling, and immune responses (Quin et al., 2000; McGucken et al., 1995; Dong et al., 1997; Henderson et al., 1998). A non-limiting example of an amino acid sequence of a MUC1 gene product from humans is presented in SEQ ID NO: 1. Nucleotide and amino acid sequences of MUC1 gene products from other species include GENBANK® Accession NOs: AAA39755, Q02496, and NP_038633 (mouse), NP_036734 (rat), NP_001181906 (dog), AA063589 (pig), and NP_776540 (cow).

Additionally, it has been determined that TAB-004 binds to K-ras polypeptides, and in particular, mutant K-ras polypeptides. As used herein, the term "K-ras" refers to a K-ras oncogene gene and gene products therefrom (see e.g., Kahn et al., 1987). An exemplary K-ras gene product is a human K-ras gene product including, but not limited to that disclosed as SEQ ID NO: 2, which corresponds to GENBANK® Accession No. NP_004976.

As used herein, the term "K-ras" also encompasses mutated forms of K-ras. As used herein, the terms "mutated K-ras", "mutant K-ras polypeptide", and "mutant K-ras protein" are used interchangeably to refer to a K-ras polypeptide comprising at least one K-ras mutation as compared to SEQ ID NO: 2. In some embodiments, a mutant K-ras polypeptide comprises a mutation at either amino acid number 12 or 13 of the mature polypeptide (i.e., amino acid position 13 or 14 of SEQ ID NO: 2 since the mature polypeptide would not include the methionine residue at position 1 of SEQ ID NO: 2). In some embodiments, a mutant K-ras polypeptide comprises a mutation selected from among a glycine-12 mutation to serine (referred to herein as "G12S"), G12V, G12D, G12A, G12C, G13A, and G13D. A representative example of a mutant K-ras$^{G12D}$ polypeptide to which antibodies of the presently disclosed subject matter bind in part is shown in SEQ ID NO: 2 and described in Kahn et al., 1987. In some embodiments, the antibodies, and the fragments and derivatives thereof, of the presently disclosed subject matter bind to a portion of a K-ras polypeptide that comprises a G12D mutation (referred to herein as "mutant K-ras G12D" or "K-ras$^{G12D}$"). Additional exemplary mutant K-ras polypeptides include, but are not limited to, allelic variants, splice variants, derivative variants, substitution variants, deletion variants, insertion variants, fusion polypeptides, orthologs, and interspecies homologs. In some embodiments, a mutant K-ras polypeptide can include one or more additional residues at the C- or N-terminus, such as, but not limited to, leader sequence residues, targeting residues, amino terminal methionine residues, lysine residues, tag residues, and/or fusion protein residues.

Figure 6:
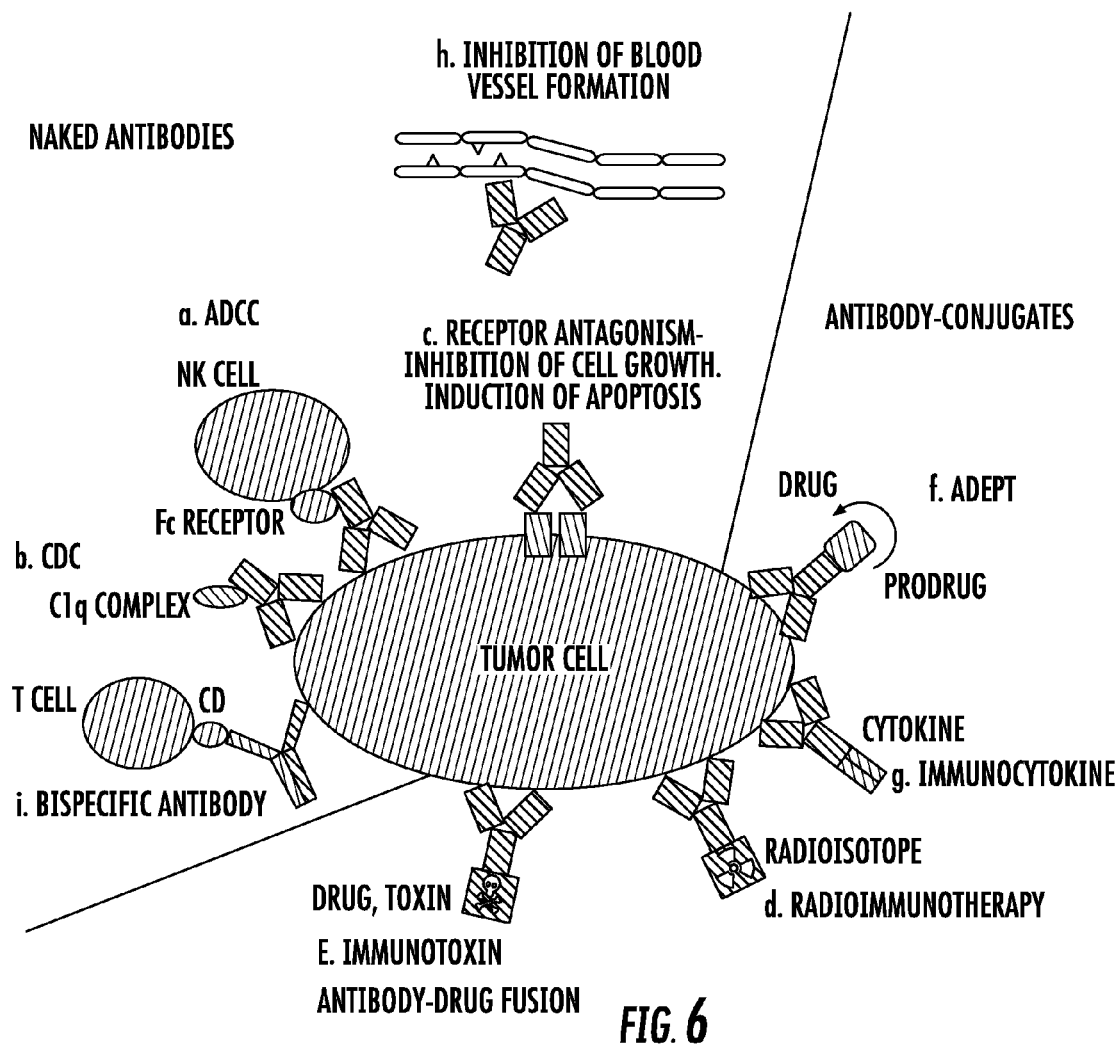
FIG. 6 is a schematic depiction of exemplary compositions of the presently disclosed subject matter and exemplary uses therefor. ADCC—antibody dependent cell-mediated cytotoxicity; CDC—complement dependent cytotoxicity; ADEPT—antibody directed enzyme prodrug therapy.

II.B. Compositions Comprising Antibodies, Fragments, and/or Derivatives of the Presently Disclosed Subject Matter The presently disclosed subject matter also provides compositions comprising the presently disclosed antibodies, fragments, and/or derivatives. A schematic depiction of exemplary compositions of the presently disclosed subject matter and exemplary uses therefor is provided in FIG. 6.

In some embodiments, a composition of the presently disclosed subject matter comprises the presently disclosed antibodies, fragments, and/or derivatives thereof and one or more pharmaceutically acceptable carriers and/or excipients. In some embodiments, the carrier(s) and/or excipient(s) is pharmaceutically acceptable for use in humans. Suitable formulations include aqueous and non-aqueous sterile injection solutions which can contain anti-oxidants, buffers, bacteriostats, bactericidal antibiotics, and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS) in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used.

The compositions of the presently disclosed subject matter can also comprise an active agent, wherein the active agent comprises a therapeutic moiety, a diagnostic moiety, and/or a biologically active moiety. As used herein, the phrase "active agent" thus refers to a component of the presently disclosed compositions that provides a therapeutic benefit to a subject, permits visualization of cells or tissues in which the compositions of the presently disclosed subject matter accumulate, detection of epitopes to which the presently disclosed antibodies, fragments, and derivatives bind, and/or enhances any of these activities. In some embodiments, an active agent of the presently disclosed subject matter is selected from the group consisting of a radioactive molecule (including, but not limited to radionuclides and radioisotopes), a sensitizer molecule, an imaging agent or other detectable agent, a toxin, a cytotoxin, an anti-angiogenic agent, an anti-tumor agent, a chemotherapeutic agent, an immunomodulator, a cytokine, a reporter group, and combinations thereof. It is understood that these categories are not intended to be mutually exclusive, as some radioactive molecules, for example, are also chemotherapeutic agents, some immunomodulators are cytokines, etc.

In some embodiments, an active agent comprises a chemotherapeutic. Various chemotherapeutics are known to one of ordinary skill in the art, and include, but are not limited to alkylating agents such as nitrogen mustards (e.g., Chlorambucil, Cyclophosphamide, Isofamide, Mechlorethamine, Melphalan, Uracil mustard), aziridines (e.g., Thiotepa), methanesulfonate esters (e.g., Busulfan), nitroso ureas (e.g., Carmustine, Lomustine, Streptozocin), platinum complexes (e.g., Cisplatin, Carboplatin), and bioreductive alkylators (e.g., Mitomycin C, Procarbazine); DNA strand breaking agents (e.g., Bleomycin); DNA topoisomerase I inhibitors (e.g., camptothecin and derivatives thereof including, but not limited to 10-hydroxycamptothecin), DNA topoisomerase II inhibitors (e.g., Amsacrine, Dactinomycin, Daunorubicin, Doxorubicin, Idarubicin, Mitoxantrone, Etoposide, Teniposide, Podophyllotoxin); DNA minor groove binders (e.g., Plicamycin); anti-metabolites such as folate antagonists (e.g., Methotrexate and trimetrexate), pyrimidine antagonists (e.g., Fluorouracil, Fluorodeoxyuridine, CB3717, Azacytidine, Cytarabine, Floxuridine), purine antagonists (e.g., Mercaptopurine, 6-Thioguanine, Fludarabine, Pentostatin), sugar modified analogs (e.g., Cyctrabine, Fludarabine), and ribonucleotide reductase inhibitors (e.g., Hydroxyurea); tubulin interactive agents (e.g., Vincristine, Vinblastine, Paclitaxel); adrenal corticosteroids (e.g., Prednisone, Dexamethasone, Methylprednisolone, Prednisolone); hormonal blocking agents such as estrogens and related compounds (e.g., Ethinyl Estradiol, Diethylstilbesterol, Chlorotrianisene, Idenestrol), progestins (e.g., Hydroxyprogesterone caproate, Medroxyprogesterone, Megestrol), androgens (e.g., Testosterone, Testosterone propionate; Fluoxymesterone, Methyltestosterone), leutinizing hormone releasing hormone agents and/or gonadotropin-releasing hormone antagonists (e.g., Leuprolide acetate; Goserelin acetate), anti-estrogenic agents (e.g., Tamoxifen), anti-androgen agents (e.g., Flutamide), and anti-adrenal agents (e.g., Mitotane, Aminoglutethimide). Other chemotherapeutics include, but are not limited to Taxol, retinoic acid and derivatives thereof (e.g., 13-cis-retinoic acid, all-trans-retinoic acid, and 9-cis-retinoic acid), sulfathiazole, mitomycin C, mycophenolic acid, sulfadiethoxane, and gemcitabine (4-amino-1-(2-deoxy-2,2-difluoro-β-D-erythro-pentofuranosyl)pyrimidin-2(1H)-on-2',2'-difluoro-2'-deoxycytidine).

In some embodiments, an active agent comprises an anti-angiogenic agent. Various anti-angiogenic agents are known to one of ordinary skill in the art, and include, but are not limited to inhibitors and/or antagonists of vascular endothelial growth factor (VEGF) family and its receptors (e.g., Bevacizumab and other anti-vascular endothelial growth factor (VEGF) antibodies) and neuropilin-1 antagonists.

In some embodiments, the compositions of the presently disclosed subject matter can be used with additional adjuvants and/or immunomodulators. As used herein, the phrases "immune modulating agent" and "immunomodulating agent" refer to molecules cable of modulating immune responses. Exemplary immunomodulators include, but are not limited to cytokines (including, but not limited to, the cytokines IFN-α, IFN-γ, IL-2, IL-4, IL-6, TNF, and other cytokines affecting immune cells), CpG oligodeoxynucleotides (CpG ODN), which function as a dendritic cell activator (Rothenfusser et al., 2002), and the immunomodulators set forth in Table 3.

TABLE 3

Exemplary Immunomodulators*

| Target | Modulators |
| --- | --- |
| indoleamine 2,3-dioxygenase (IDO) | 1MT; MTH-Trp |
| Arginase (ARG) | ABH; BEC |
| inducible nitric oxide synthase (iNOS) | L-NMMA |
| ARG/iNOS | NCX-4016 |
| COX-2 | Celecoxib; Rofecoxib |
| EP2/EP4 | CP-533536 |
| TGFβRI | SB-505124; SD-505124; LY580276 |
| JAK/STAT | JSI-124; CPA-7 |
| VEGFR1/FLT1 | SU5416; AG-013736 |
| CCR4 | IC-487892 |
| CXCR4 | AMD3100 |
| CCR2 | INCB3344 |

*see Muller & Scherle, 2006 and references therein. MTH-TRP: methyl-thiohydantoin-tryptophan; ABH: 2(S)-amino-6-boronohexanoic acid; BEC: S-(2-boronoethyl)-L-cysteine; L-NMMA: L-N$^G$-monomethyl arginine; NCX-4016: nitroaspirin; see Emanueli et al., 2004; CP-533536: see Cameron et al., 2009; SB-505124: see DeCosta Byfield et al., 2004; SD-505124: see Muller & Scherle, 2006; LY580276: see Sawyer et al., 2004; JSI-124: see Blaskovich et al., 2003; CPA-7: see Littlefield et al., 2008; SU5416: see Fong et al., 1999; AG-013736 (Axitinib); see Rugo et al., 2005; IC-487892: ICOS Corp., Bothell, Washington, United States of America; AMD3100: see Donzella et al., 1998.

For therapeutic applications, a therapeutically effective amount of a composition of the presently disclosed subject matter is administered to a subject. A "therapeutically effective amount" is an amount of a composition sufficient to produce a measurable biological tumor response (such as, but not limited to an immunostimulatory, an anti-angiogenic response, a cytotoxic response, tumor regression, and/or tumor growth inhibition). Actual dosage levels of active ingredients in a composition of the presently disclosed subject matter can be varied so as to administer an amount of the active agent(s) that is effective to achieve the desired therapeutic response for a particular subject. The selected dosage level will depend upon a variety of factors including the activity of the composition, formulation, the route of administration, combination with other drugs or treatments, tumor size and longevity, and the physical condition and prior medical history of the subject being treated. In some embodiments of the presently disclosed subject matter, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

For diagnostic applications, a detectable amount of a composition of the presently disclosed subject matter is administered to a subject. A "detectable amount", as used herein to refer to a composition, refers to a dose of such a composition that the presence of the composition can be determined in vivo or in vitro. A detectable amount will vary according to a variety of factors, including but not limited to chemical features of the composition being labeled, the detectable label, the labeling methods, the method of imaging and parameters related thereto, metabolism of the labeled drug in the subject, the stability of the label (including, but not limited to the half-life of a radionuclide label), the time elapsed following administration of the composition prior to imaging, the route of administration, the physical condition and prior medical history of the subject, and the size and longevity of the tumor or suspected tumor. Thus, a detectable amount can vary and can be tailored to a particular application. After study of the present disclosure, it is within the skill of one in the art to determine such a detectable amount.

As used herein, the terms "detectable moiety", "detectable label", and "detectable agent" refer to any molecule that can be detected by any moiety that can be added to an antibody, or a fragment or derivative thereof, that allows for the detection of the antibody, fragment, or derivative in vitro and/or in vivo. Representative detectable moieties include, but are not limited to, chromophores, fluorescent moieties, enzymes, antigens, groups with specific reactivity, chemiluminescent moieties, and electrochemically detectable moieties, etc. In some embodiments, the antibodies are biotinylated.

In some embodiments, a detectable moiety comprises a fluorophore. Any fluorophore can be employed with the compositions of the presently disclosed subject matter, provided that the conjugation of fluorophore results in a composition that is detectable either in vivo (e.g., after administration to a subject) and/or in vitro, and further does not negatively impact the ability of the antibody, or the fragment or derivative thereof, to bind to its epitope. Representative fluorophores include, but are not limited to 7-dimethylaminocoumarin-3-carboxylic acid, dansyl chloride, nitrobenzodiazolamine (NBD), dabsyl chloride, cinnamic acid, fluorescein carboxylic acid, Nile Blue, tetramethylcarboxyrhodamine, tetraethylsulfohodamine, 5-carboxy-X-rhodamine (5-ROX), and 6-carboxy-X-rhodamine (6-ROX). It is understood that these representative fluorophores are exemplary only, and additional fluorophores can also be employed. For example, there the ALEXA FLUOR® dye series includes at least 19 different dyes that are characterized by different emission spectra. These dyes include ALEXA FLUOR® 350, 405, 430, 488, 500, 514, 532, 546, 555, 568, 594, 610, 633, 635, 647, 660, 680, 700, and 750 (available from Invitrogen Corp., Carlsbad, Calif., United States of America), and the choice of which dye to employ can be made by the skilled artisan after consideration of the instant specification based on criteria including, but not limited to the chemical compositions of the specific ALEXA FLUOR®, whether multiple detectable moieties are to be employed and the emission spectra of each, the detection technique to be employed, etc.

In some embodiments, a detectable moiety comprises a cyanine dye. Non-limiting examples of cyanine dyes that can be conjugated to the antibodies, fragments, and/or derivatives of the presently disclosed subject matter include the succinimide esters Cy5, Cy5.5, and Cy7, supplied by Amersham Biosciences (Piscataway, N.J., United States of America).

In some embodiments, a detectable moiety comprises a near infrared (NIR) dye. Non-limiting examples of near infrared dyes that can be conjugated to the antibodies, fragments, and/or derivatives of the presently disclosed subject matter include NIR641, NIR664, NIT7000, and NIT782.

In some embodiments, the biotinylated antibodies are detected using a secondary antibody that comprises an avidin or streptavidin group and is also conjugated to a fluorescent label including, but not limited to Cy3, Cy5, Cy7, and any of the ALEXA FLUOR®® series of fluorescent labels available from INVITROGEN™ (Carlsbad, Calif., United States of America). In some embodiments, the antibody, fragment, or derivative thereof is directly labeled with a fluorescent label and cells that bind to the antibody are separated by fluorescence-activated cell sorting. Additional detection strategies are known to the skilled artisan.

For diagnostic applications (including but not limited to detection applications and imaging applications), the antibodies of the presently disclosed subject matter can be labeled with a detectable moiety. The detectable moiety can be any one that is capable of producing, either directly or indirectly, a detectable signal. For example, a detectable moiety can be a radioisotope, such as but not limited to $^{3}H$, $^{14}C$, $^{32}P$, $^{35}S$, $^{125}I$, or $^{131}I$; a fluorescent or chemiluminescent compound such as but not limited to fluorescein isothiocyanate, rhodamine, or luciferin; or an enzyme, such as but not limited to alkaline phosphatase, β-galactosidase, or horseradish peroxidase.

The presently disclosed subject matter further provides methods for diagnosing a tumor, wherein a tumor sample or biopsy is evaluated in vitro. In some embodiments, a targeting ligand of the presently disclosed subject matter comprises a detectable label such as a fluorescent label, an epitope tag, or a radioactive label, each described briefly herein below.

Fluorescence. Any detectable fluorescent dye can be used, including but not limited to FITC (fluorescein isothiocyanate), FLUOR X™, ALEXA FLUOR®, OREGON GREEN®, TMR (tetramethylrhodamine), ROX (X-rhodamine), TEXAS RED®, BODIPY® 630/650, and Cy5 (available from Amersham Pharmacia Biotech of Piscataway, N.J., United States of America, or from Molecular Probes Inc. of Eugene, Oreg., United States of America).

A fluorescent label can be detected directly using emission and absorbance spectra that are appropriate for the particular label used. Common research equipment has been developed for in vitro detection of fluorescence, including instruments available from GSI Lumonics (Watertown, Mass., United States of America) and Genetic MicroSystems Inc. (Woburn, Mass., United States of America). Most of the commercial systems use some form of scanning technology with photomultiplier tube detection. Criteria for consideration when analyzing fluorescent samples are summarized by Alexay et al., 1996.

Detection of an Epitope Tag. If an epitope label has been used, a protein or compound that binds the epitope can be used to detect the epitope. A representative epitope label is biotin, which can be detected by binding of an avidin-conjugated fluorophore, for example avidin-FITC. Alternatively, the label can be detected by binding of an avidin-horseradish peroxidase (HRP) streptavidin conjugate, followed by colorimetric detection of an HRP enzymatic product. The production of a colorimetric or luminescent product/conjugate is measurable using a spectrophotometer or luminometer, respectively.

Autoradiographic Detection. In the case of a radioactive label (e.g., $^{131}I$ or $^{99m}Tc$) detection can be accomplished by conventional autoradiography or by using a phosphorimager as is known to one of skill in the art. A preferred autoradiographic method employs photostimulable luminescence imaging plates (Fuji Medical Systems of Stamford, Conn., United States of America). Briefly, photostimulable luminescence is the quantity of light emitted from irradiated phosphorous plates following stimulation with a laser during scanning. The luminescent response of the plates is linearly proportional to the activity (Amemiya et al., 1988; Hallahan et al., 2001a).

Any method known in the art for conjugating an antibody to a detectable moiety can be employed (see e.g., Hunter et al., 1962; David et al., 1974; Pain et al., 1981); and Nygren, 1982.

Drug Carriers. The compositions of the presently disclosed subject matter can further comprise a drug carrier to facilitate drug preparation and administration. Any suitable drug delivery vehicle or carrier can be used, including but not limited to a gene therapy vector (e.g., a viral vector or a plasmid), a microcapsule, for example a microsphere or a nanosphere (Manome et al., 1994; Hallahan et al., 2001b; Saltzman & Fung, 1997), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al., 1997; U.S. Pat. Nos. 4,551,482; 5,714,166; 5,510,103; 5,490,840; and 5,855,900), and a polysome (U.S. Pat. No. 5,922,545).

Conjugation of Targeting Ligands. Antibodies, fragments, or derivatives can also be coupled to drugs or drug carriers using methods known in the art, including but not limited to carbodiimide conjugation, esterification, sodium periodate oxidation followed by reductive alkylation, and glutaraldehyde crosslinking (see e.g., Goldman et al., 1997; Cheng, 1996; Neri et al., 1997; Nabel, 1997; Park et al., 1997; Pasqualini et al., 1997; Bauminger & Wilchek, 1980; U.S. Pat. No. 6,071,890; and European Patent No. 0 439 095.

Administration. Suitable methods for administration of a composition of the presently disclosed subject matter include, but are not limited to intravascular, subcutaneous, intramuscular, and intratumoral administration. In some embodiments, intravascular administration is employed. As used herein, the phrases "intravascular administration" and "intravascular provision" refer to administration of a composition directly into the vascular network of a subject. Techniques that can be employed for intravascular administration of compositions are known to those of skill in the art, and include, but are not limited to intravenous administration and intraarterial administration. It is understood that any site and method for intravascular administration can be chosen, depending at least in part on the species of the subject to which the composition is to be administered. For delivery of compositions to pulmonary pathways, compositions can be administered as an aerosol or coarse spray.

III. Methods for Detecting Epitopes in Biological Samples

The antibodies, and/or the fragments and/or derivatives thereof, of the presently disclosed subject matter also are useful for in vivo imaging, wherein an antibody labeled with a detectable moiety such as a radio-opaque agent and/or a radioisotope is administered to a subject, in some embodiments via intravenous administration, and the presence and location of the labeled antibody in the host is assayed. This imaging technique can be useful in the staging and treatment of malignancies.

Thus, in some embodiments, a composition of the presently disclosed subject matter comprises a label that can be detected in vivo. The term "in vivo" as used herein to describe imaging or detection methods, refers to generally non-invasive methods such as scintigraphic methods, magnetic resonance imaging, ultrasound, or fluorescence, each described briefly herein below. The term "non-invasive methods" does not exclude methods employing administration of a contrast agent to facilitate in vivo imaging.

In some embodiments, the detectable moiety can be conjugated or otherwise associated with an antibody, fragment, or derivative of the presently disclosed subject matter, a therapeutic, a diagnostic agent, a drug carrier, or combinations thereof as set forth in more detail hereinabove. Following administration of the labeled composition to a subject, and after a time sufficient for binding, the biodistribution of the composition can be visualized. The term "time sufficient for binding" refers to a temporal duration that permits binding of the labeled agent to a radiation-induced target molecule.

Scintigraphic Imaging. Scintigraphic imaging methods include SPECT (Single Photon Emission Computed Tomography), PET (Positron Emission Tomography), gamma camera imaging, and rectilinear scanning. A gamma camera and a rectilinear scanner each represent instruments that detect radioactivity in a single plane. Most SPECT systems are based on the use of one or more gamma cameras that are rotated about the subject of analysis, and thus integrate radioactivity in more than one dimension. PET systems comprise an array of detectors in a ring that also detect radioactivity in multiple dimensions.

Imaging instruments suitable for practicing the detection and/or imaging methods of the presently disclosed subject matter, and instruction for using the same, are readily available from commercial sources. Both PET and SPECT systems are offered by ADAC of Milpitas, Calif., United States of America, and Siemens of Hoffman Estates, Ill., United States of America. Related devices for scintigraphic imaging can also be used, such as a radio-imaging device that includes a plurality of sensors with collimating structures having a common source focus.

When scintigraphic imaging is employed, the detectable label comprises in some embodiments a radionuclide label, in some embodiments a radionuclide label selected from the group consisting of $^{18}$F, $^{64}$Cu, $^{65}$Cu, $^{67}$Ga, $^{68}$Ga, $^{77}$Br, $^{80m}$Br, $^{95}$Ru, $^{97}$Ru, $^{103}$Ru, $^{105}$Ru, $^{99m}$Tc, $^{107}$Hg, $^{203}$Hg, $^{123}$I, $^{124}$I, $^{125}$I, $^{126}$I, $^{131}$I, $^{133}$I, $^{111}$In, $^{113m}$In, $^{99m}$Re, $^{105}$Re, $^{101}$Re, $^{186}$Re, $^{188}$Re, $^{121m}$Te, $^{122}$Te, $^{125m}$Te, $^{165}$Tm, $^{167}$Tm, $^{168}$Tm, and nitride or oxide forms derived there from. In some embodiments, the radionuclide label comprises $^{131}$I or $^{99m}$Tc.

Methods for radionuclide labeling of a molecule so as to be used in accordance with the disclosed methods are known in the art. For example, a targeting molecule can be derivatized so that a radioisotope can be bound directly to it (Yoo et al., 1997). Alternatively, a linker can be added that to enable conjugation. Representative linkers include diethylenetriamine pentaacetate (DTPA)-isothiocyanate, succinimidyl 6-hydrazinium nicotinate hydrochloride (SHNH), and hexamethylpropylene amine oxime (HMPAO; Chattopadhyay et al., 2001; Sagiuchi et al., 2001; and U.S. Pat. No. 6,024,938). Additional methods can be found in U.S. Pat. No. 6,080,384; Hnatowich et al., 1996; and Tavitian et al., 1998.

When the labeling moiety is a radionuclide, stabilizers to prevent or minimize radiolytic damage, such as ascorbic acid, gentisic acid, or other appropriate antioxidants, can be added to the composition comprising the labeled targeting molecule.

Magnetic Resonance Imaging (MRI). Magnetic resonance image-based techniques create images based on the relative relaxation rates of water protons in unique chemical environments. As used herein, the term "magnetic resonance imaging" refers to magnetic source techniques including convention magnetic resonance imaging, magnetization transfer imaging (MTI), proton magnetic resonance spectroscopy (MRS), diffusion-weighted imaging (DWI) and functional MR imaging (fMRI; see e.g., Rovaris et al., 2001; Pomper & Port, 2000; and references cited therein).

Contrast agents for magnetic source imaging include but are not limited to paramagnetic or superparamagnetic ions, iron oxide particles (Weissleder et al., 1992; Shen et al., 1993), and water-soluble contrast agents. Paramagnetic and superparamagnetic ions can be selected from the group of metals including iron, copper, manganese, chromium, erbium, europium, dysprosium, holmium and gadolinium. Preferred metals are iron, manganese and gadolinium; most preferred is gadolinium.

Those skilled in the art of diagnostic labeling recognize that metal ions can be bound by chelating moieties, which in turn can be conjugated to a therapeutic agent in accordance with the methods of the presently disclosed subject matter. For example, gadolinium ions are chelated by diethylenetriaminepentaacetic acid (DTPA). Lanthanide ions are chelated by tetraazaclododocane compounds. See U.S. Pat. Nos. 5,738,837 and 5,707,605. Alternatively, a contrast agent can be carried in a liposome (Schwendener, 1992).

Images derived used a magnetic source can be acquired using, for example, a superconducting quantum interference device magnetometer (SQUID, available with instruction from Quantum Design of San Diego, Calif., United States of America; see also U.S. Pat. No. 5,738,837).

Ultrasound. Ultrasound imaging can be used to obtain quantitative and structural information of a target tissue, including a tumor. Administration of a contrast agent, such as gas microbubbles, can enhance visualization of the target tissue during an ultrasound examination. In some embodiments, the contrast agent can be selectively targeted to the target tissue of interest, for example by using a peptide for guided drug delivery (e.g., radiation guided drug delivery) as disclosed herein. Representative agents for providing microbubbles in vivo include but are not limited to gas-filled lipophilic or lipid-based bubbles (e.g., U.S. Pat. Nos. 6,245, 318; 6,231,834; 6,221,018; and 5,088,499). In addition, gas or liquid can be entrapped in porous inorganic particles that facilitate microbubble release upon delivery to a subject (U.S. Pat. Nos. 6,254,852 and 5,147,631).

Gases, liquids, and combinations thereof suitable for use with the presently disclosed subject matter include air; nitrogen; oxygen; is carbon dioxide; hydrogen; nitrous oxide; an inert gas such as helium, argon, xenon or krypton; a sulfur fluoride such as sulfur hexafluoride, disulfur decafluoride or trifluoromethylsulfur pentafluoride; selenium hexafluoride; an optionally halogenated silane such as tetramethylsilane; a low molecular weight hydrocarbon (e.g. containing up to 7 carbon atoms), for example an alkane such as methane, ethane, a propane, a butane or a pentane, a cycloalkane such as cyclobutane or cyclopentane, an alkene such as propene or a butene, or an alkyne such as acetylene; an ether; a ketone; an ester; a halogenated low molecular weight hydrocarbon (e.g. containing up to 7 carbon atoms); or a mixture of any of the foregoing. Halogenated hydrocarbon gases can show extended longevity, and thus are preferred for some applications. Representative gases of this group include decafluorobutane, octafluorocyclobutane, decafluoroisobutane, octafluoropropane, octafluorocyclopropane, dodecafluoropentane, decafluorocyclopentane, decafluoroisopentane, perfluoropexane, perfluorocyclohexane, perfluoroisohexane, sulfur hexafluoride, and perfluorooctaines, perfluorononanes; perfluorodecanes, optionally brominated.

Attachment of targeting ligands to lipophilic bubbles can be accomplished via chemical crosslinking agents in accordance with standard protein-polymer or protein-lipid attachment methods (e.g., via carbodiimide (EDC) or thiopropionate (SPDP)). To improve targeting efficiency, large gas-filled bubbles can be coupled to a targeting ligand using a flexible spacer arm, such as a branched or linear synthetic polymer (U.S. Pat. No. 6,245,318). A targeting ligand can be attached to the porous inorganic particles by coating, adsorbing, layering, or reacting the outside surface of the particle with the targeting ligand (U.S. Pat. No. 6,254,852).

A description of ultrasound equipment and technical methods for acquiring an ultrasound dataset can be found in Coatney, 2001; Lees, 2001; and references cited therein.

Fluorescence Imaging. Non-invasive imaging methods can also comprise detection of a fluorescent label. A drug comprising a lipophilic component (therapeutic agent, diagnostic agent, vector, or drug carrier) can be labeled with any one of a variety of lipophilic dyes that are suitable for in vivo imaging (see e.g., Heredia et al., 1991; Ragnarson et al., 1992; Fraser, 1996). Representative labels include but are not limited to carbocyanine and aminostyryl dyes, preferably long chain dialkyl carbocyanines (e.g., Dil, DiO, and DiD available from Molecular Probes Inc. of Eugene, Oreg., United States of America) and dialkylaminostyryl dyes. Lipophilic fluorescent labels can be incorporated using methods known to one of skill in the art. For example VYBRANT™ cell labeling solutions are effective for labeling of cultured cells of other lipophilic components (Molecular Probes Inc. of Eugene, Oreg., United States of America).

A fluorescent label can also comprise sulfonated cyanine dyes, including Cy5.5 and Cy5 (available from Amersham of Arlington Heights, Ill., United States of America), IRD41 and IRD700 (available from Li-Cor, Inc. of Lincoln, Nebr.), NIR-1 (available from Dejindo of Kumamoto, Japan), and LaJolla Blue (available from Diatron of Miami, Fla., United States of America; see also Licha et al., 2000; Weissleder et al., 1999; Vinogradov et al., 1996).

In addition, a fluorescent label can comprise an organic chelate derived from lanthanide ions, for example fluorescent chelates of terbium and europium (U.S. Pat. No. 5,928,627). Such labels can be conjugated or covalently linked to a drug as disclosed therein.

For in vivo detection of a fluorescent label, an image is created using emission and absorbance spectra that are appropriate for the particular label used. The image can be visualized, for example, by diffuse optical spectroscopy. Additional methods and imaging systems are described in U.S. Pat. Nos. 5,865,754; 6,083,486; and 6,246,901, among other places.

IV. Methods for Detecting and Treating Tumors

In some embodiments, the antibodies, fragments, and/or derivatives of the presently disclosed subject matter are employed for in vivo imaging of tumors, wherein a composition of the presently disclosed subject matter that has been labeled with an imaging moiety such as a radio-opaque agent, a radioisotope, or other imaging agent is administered to a subject, and the presence and location of the detectibly-labeled composition in the subject is assayed. This imaging technique can be useful in the staging and treatment of malignancies. In some embodiments, an antibody is labeled with any moiety that is detectable in situ in a subject, for example by nuclear magnetic resonance, radiology, or other detection methods known in the art.

As such, the presently disclosed subject matter also provides methods for detecting tumors in subjects. In some embodiments, the presently disclosed methods comprise (a) administering to the subject a composition comprising the antibody, or the fragment or derivative thereof, of the presently disclosed subject matter conjugated to a detectable label; and (b) detecting the detectable label to thereby detect the tumor. In some embodiments, the tumor is a tumor of the pancreas, breast, ovary, colon, or rectum, and/or a metastatic cell derived therefrom, which optionally expresses MUC1, a mutant K-ras, or both.

In some embodiments of the presently disclosed subject matter, the detectable label comprises an imaging agent selected from the group consisting of paramagnetic, radioactive, and fluorogenic ions including, but not limited to those set forth in more detail hereinabove. In view of the disclosure above, the radioactive imaging agent can be, for example, gamma-emitters, positron-emitters, x-ray-emitters, or any other agents for which a detection method is available. Exemplary such radioactive imaging agents include $^{43}$K, $^{52}$Fe, $^{57}$Co, $^{67}$Cu, $^{67}$Ga, $^{68}$Ga, $^{77}$Br, $^{81}$Rb/$^{81}$MKr, $^{87M}$Sr, $^{99M}$Tc, $^{111}$In, $^{113}$In, $^{123}$I, $^{125}$I, $^{127}$Cs, $^{129}$Cs, $^{131}$I, $^{132}$I, $^{197}$Hg, $^{203}$Pb, and $^{206}$Bi, but the presently disclosed subject matter is not limited to just these radioisotopes.

The presently disclosed subject matter also provides methods for treating tumors. In some embodiments, the methods comprise administering to the subject a composition comprising an antibody, or a fragment or derivative thereof of the presently disclosed subject matter conjugated to an active agent, whereby the active agent contacts the tumor to thereby treat the tumor. Exemplary active agents are disclosed herein, and include but are not limited to therapeutic agents, optionally chemotherapeutic agents, toxins, radiotherapeutic agents, and combinations of any of the foregoing.

For example, a composition of the presently disclosed subject matter can comprise an antibody, or a fragment or derivative thereof as disclosed herein conjugated to a chemotherapeutic agent. In some embodiments, the chemotherapeutic agent is selected from among an anti-tumor drug, a cytokine, an anti-metabolite, an alkylating agent, a hormone, methotrexate, doxorubicin, daunorubicin, cytosine arabinoside, etoposide, 5-fluorouracil, melphalan, chlorambucil, a nitrogen mustard, cyclophosphamide, cis-platinum, vindesine, vinca alkaloids, mitomycin, bleomycin, purothionin, macromomycin, 1,4-benzoquinone derivatives, trenimon, steroids, aminopterin, anthracyclines, demecolcine, etoposide, mithramycin, doxorubicin, daunomycin, vinblastine, neocarzinostatin, macromycin, α-amanitin, and combinations thereof.

Additionally, a composition of the presently disclosed subject matter can comprise an antibody, or a fragment or derivative thereof as disclosed herein conjugated to a toxin. Exemplary toxins include, but are not limited to Russell's Viper Venom, activated Factor IX, activated Factor X, thrombin, phospholipase C, cobra venom factor, ricin, ricin A chain, *Pseudomonas* exotoxin, diphtheria toxin, bovine pancreatic ribonuclease, pokeweed antiviral protein, abrin, abrin A chain, gelonin, saporin, modeccin, viscumin, volkensin, and combinations thereof.

The compositions of the presently disclosed subject matter can also comprise an antibody, or a fragment or derivative thereof as disclosed herein conjugated to a radiotherapeutic agent. Exemplary radiotherapeutic agents include, but are not limited to $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$Bi, $^{32}$P, $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, and $^{197}$Hg.

The presently disclosed subject matter also provides methods for suppressing tumor growth in a subject. In some embodiments, the methods comprise administering to a subject bearing a tumor an effective amount of an isolated antibody, fragment, or derivative of the presently disclosed subject matter. In some embodiments, the antibody, fragment, or derivative of the presently disclosed subject matter binds to an epitope present within any of SEQ ID NOs: 1-3. In some embodiments, the tumor is a tumor of the pancreas, breast, ovary, colon, or rectum, and/or a metastatic cell derived therefrom, which in some embodiments expresses MUC1, a mutant K-ras, or both.

The presently disclosed subject matter also encompasses employing the compositions and methods disclosed herein as part of a combination therapy. As such, the presently disclosed subject matter provides in some embodiments administering to the subject one or more additional anti-tumor treatments. Exemplary anti-tumor treatments include but are not limited to radiotherapy, chemotherapy, an additional immunotherapy, an anti-inflammatory therapy, and combinations thereof.

For example, an anti-inflammatory therapy can comprise administering to the subject an anti-inflammatory agent such as, but not limited to a non-steroidal anti-inflammatory drug (NSAID). Exemplary NSAIDs include, but are not limited to cyclooxygenase inhibitors (e.g., indomethacin), particularly cyclooxygenase-2-specific inhibitors such as, but not limited to celecoxib and rofecoxib.

Combination therapies can also include administration of one or more additional anti-tumor therapies such as, but not limited to administering gemcitabine, which is 4-amino-1-(2-deoxy-2,2-difluoro-β-D-erythro-pentofuranosyl)pyrimidin-2(1H)-on-2',2'-difluoro-2'-deoxycytidine; celecoxib, which is 4-[5-(4-methylphenyl)-3-(trifluoromethyl)pyrazol-1-yl] benzenesulfonamide, pharmaceutically acceptable salts thereof, and/or combinations thereof to the subject.

Combination therapies can also include administration of ionizing radiation to the subject, before, during, and/or after the administration course of any of the compositions of the presently disclosed subject matter.

For therapeutic applications, the antibodies, fragments, derivatives, and/or conjugates thereof can be administered to a subject, for example in a pharmaceutically acceptable dosage form. They can be administered intravenously as a bolus or by continuous infusion over a period of time, by intramuscular, subcutaneous, intra-articular, intrasynovial, intrathecal, oral, topical, or inhalation routes. The antibodies and/or conjugates can also be administered by intratumoral, peritumoral, intralesional, or perilesional routes, to exert local as well as systemic therapeutic effects, as desired.

Suitable pharmaceutically acceptable carriers, diluents, and/or excipients are well known and can be employed by those of skill in the art as the clinical situation warrants. Examples of suitable carriers, diluents, and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

When present in an aqueous dosage form, rather than being lyophilized, the antibody typically will be formulated at a concentration of about 0.1 mg/ml to 100 mg/ml, although wide variation outside of these ranges is permitted.

For additional guidance regarding formulation and dose, see U.S. Pat. Nos. 5,326,902; 5,234,933; PCT International Publication No. WO 1993/25521; Gennaro, 1990; Goodman et al., 1996; Berkow et al., 1997; Speight et al., 1997; Duch et al., 1998; Ebadi, 1998; Katzung, 2001; Gennaro, 2003.

The compositions and methods of the presently disclosed subject matter can be employed in vitro, in vivo, or ex vivo.

The compositions and methods of the presently disclosed subject matter can be used for screening and/or treatment of a cancer in which MUC1 or mutated K-ras expression is elevated. Examples of such cancers include, but are not limited to, cancers of the ovary, breast, lung, pancreas, and prostate.

For the treatment of disease, an appropriate dosage of an antibody, fragment, or derivative thereof, and/or a conjugate thereof of the presently disclosed subject matter can depend on the type of disease to be treated, the severity and course of the disease, whether the antibodies and/or conjugates are administered for preventive or therapeutic purposes, the course of previous therapy, the patient's clinical history and response to the antibodies and/or conjugates, and the discretion of the attending physician. The antibodies and/or conjugates of the presently disclosed subject matter can be administered to a subject at one time or over a course of several or many treatments.

V. Methods for Detecting, Purifying, and Targeting Tumor Cells and Cancer Stem Cells The presently disclosed subject matter also provides methods for detecting, purifying, and targeting tumor cells, cancer stem cells, or both present in a subject or isolated from a subject using the antibodies, or the fragments or derivatives thereof, disclosed herein. In some embodiments, the presently disclosed subject matter provides methods for detecting tumor cells, cancer stem cells, or both by detecting the binding of an antibody, or a fragment or derivative thereof to tumor cells, cancer stem cells, or both present in biological samples isolated from subjects who had and/or presently have a cancer. The compositions disclosed herein that employ detectable labels can be employed for this purpose.

Additionally, the presently disclosed subject matter provides methods for purifying cancer stem cells. In some embodiments, the methods comprise (a) providing a population of cells suspected of comprising cancer stem cells; (b) identifying a subpopulation of the cells that bind to an antibody, or a fragment or derivative thereof, the binds to an epitope present within any of SEQ ID NOs: 1-3; and (b) purifying the subpopulation. With respect to purification methods, in some embodiments the population of cells comprises circulating cells isolated from a subject that has a cancer.

In some embodiments, the methods further comprise removing lineage positive (lin$^+$) cells from the population of cells before the identifying step or removing lin$^+$ cells from the purified subpopulation. Methods for removing lin$^+$ cells from cell populations are known in the art. An exemplary method is as follows:

Single cell suspensions are either isolated from a subject (e.g., from blood, lymph fluids, bone marrow aspirates, etc.) or are prepared from tissues. In the case of tissues, sections from a tissue suspected of having cancer stem cells (e.g., pancreatic adenocarcinoma tissue) can be mechanically homogenized and digested with collagenase IV and DNase for 30 minutes at 37° C. Whole blood and single cell suspension from the tumor can be subjected to lineage cell depletion using, for example, one of the several species-specific Lineage Cell Depletion Kits sold by Miltenyi Biotec (Bergisch Gladbach, Germany), which remove cells expressing the following lineage antigens: CD2, CD3, CD11b, CD14, CD15, CD16, CD19, CD56, CD123, and CD235a from the cell suspensions. The lineage negative subpopulation can then be then screened using flow cytometry for cells expressing MUC1 using, for example, the monoclonal TAB-004 antibody of the presently disclosed subject matter. It is understood that the steps of the various selections can be performed in any order. If desired, antibodies directed against the stem cell markers CD133 (AC133) and/or CD24$^+$/CD44$^+$ can also be employed.

The presently disclosed subject matter also provides methods for targeting an active agent to a circulating cancer stem cell in a subject. In some embodiments, the methods comprise contacting a cancer stem cell (optionally a circulating cancer stem cell) with a composition comprising an antibody, or a fragment or derivative thereof, of the presently disclosed subject matter and an active agent. The composition thus delivers the active agent to the cancer stem cell. Any of the active agents disclosed herein can be targeted to cancer stem cells by employing the presently disclosed compositions and methods. In some embodiments, the active agent comprises a therapeutic agent, a chemotherapeutic agent, a toxin, a radiotherapeutic agent, or a combination thereof.

For example, in some embodiments the therapeutic agent comprises an immunomodulator, which in some embodiments could one or more of an indoleamine 2,3-dioxygenase (IDO) inhibitor (e.g., 1-methyl-DL-tryptophan (1MT)); an EP2/EP4 receptor antagonist; a CXCR4 antagonist, a vascular endothelial growth factor receptor 1 antagonist, Celebrex, a TGFβR1 antagonist, and a dendritic cell activator. Non-limiting examples of these immunomodulators are provided in Table 3 above.

VI. Methods for Predicting the Recurrence and/or Progression of Cancer in a Subject As of the year 2010, breast cancer and pancreatic cancer are the third and fourth leading cause of cancer related deaths, respectively. Breast cancer is the most commonly diagnosed cancer among women, but while pancreatic cancer is less common, it has worst prognosis of all cancers. The poor prognosis associated with pancreatic cancer results at least in part from a lack of early detection methods resulting in diagnosis of the disease at an advanced stage. Although mammography has significantly improved early detection in breast cancer, it is not without its shortcomings. Up to 20% of breast cancers are missed, and false-positive results can lead to anxiety and expensive additional testing. The lack of specificity in mammography screening can lead to the "over-diagnosis" of benign tumors and unnecessary treatment.

Another concern is the presence of metastases from primary tumors to distant sites in patients, the presence of which generally correlates with poor prognosis and as such, drastically impacts the course of therapy administered to patients. Current methods that can be used to detect metastases include computed tomography (CT), positron emission tomography (PET) scans, and magnetic resonance imaging (MRI). These modalities are expensive, potentially hazardous to the individual, can lack specificity and sensitivity, and generally are incapable of detecting micrometastases.

Monitoring of recurrence in patients can also be necessary to appropriately tailor particular drug treatments. Blood-based tests for tumor antigens including, but not limited to the CA 19-9, CA 15-3, and CA 27-29 tumor antigens, can be employed for these purposes. However, these tests also frequently lack specificity as conditions other than cancer can lead to the elevation of these and other putative "tumor-associated antigens". Also frequently, the expression levels of these markers are insufficiently high during the early stages of the cancer enough in the progression of a cancer to detect the cancer before symptoms appear. The development of methodologies to specifically detect cancer at an early stage, as well as to detect micrometastases and recurrence would be beneficial to improving outcomes in pancreatic and breast cancer patients.

VI.A. Methods for Predicting Recurrence of Cancer

In some embodiments, the presently disclosed subject matter also provides methods for predicting the recurrence of cancer in a subject. In some embodiments, the methods comprise (a) isolating a biological sample comprising circulating cells from a subject with a cancer; (b) contacting the biological sample with one or more of the antibodies, fragments, or derivatives of the presently disclosed subject matter; and (c) identifying in the biological sample one or more circulating cells that bind to the one or more of the antibodies, fragments, or derivatives of the presently disclosed subject matter, whereby the recurrence of a cancer is predicted in the subject. With respect to these methods, the identification of circulating cells that bind to the antibodies, fragments, and/or derivatives of the presently disclosed subject matter can be indicative of a recurrence of a subject's cancer when the subject had previously been negative for such circulating cells. In some embodiments, the presence of circulating cells that bind to the one or more of the antibodies, fragments, or derivatives of the presently disclosed subject matter indicates that the subject is at enhanced risk of metastatic disease relative to a subject that is negative for such circulating cells.

VI.B. Methods for Prognosing Progression of Cancer

The presently disclosed subject matter also provides methods for prognosing progression of a cancer in subjects. In some embodiments, the methods comprise isolating a biological sample comprising circulating cells from a subject with a cancer; contacting the biological sample with the antibody, or the fragment or derivative thereof, of the presently disclosed subject matter under conditions sufficient for the antibody, or the fragment or derivative thereof, to bind to an epitope present on a tumor and/or a cancer cell, if present, in the biological sample; and identifying in the biological sample one or more circulating cells that bind to the antibody, or the fragment or derivative thereof, whereby progression of a cancer is prognosed in the subject. In some embodiments, the biological sample comprises a blood sample, a lymph sample, or a fraction thereof. In some embodiments, the cancer is a pancreatic cancer or a breast cancer.

In some embodiments, the antibody is a monoclonal antibody produced by hybridoma cell line TAB-004 deposited with the American Type Culture Collection (ATCC), 10801 University Boulevard, Manassas, Va., 20110-2209, United States of America, on Dec. 16, 2010 under the terms of the Budapest Treaty as Accession No. PTA-11550. In some embodiments, the fragment or derivative thereof is selected from the group consisting of a chimeric antibody, or a fragment or derivative thereof; a humanized antibody, or a fragment or derivative thereof; a human antibody, or a fragment or derivative thereof; a single chain antibody, or a fragment or derivative thereof; and a Fab fragment, wherein the chimeric antibody, the humanized antibody, the human antibody, the single chain antibody, or the Fab fragment comprises the CDRs of monoclonal antibody TAB-004, and further wherein the chimeric antibody, the humanized antibody, the human antibody, the single chain antibody, or the Fab fragment comprises the CDRs of monoclonal antibody TAB-004. In some embodiments, the CDRs of monoclonal antibody TAB-004 comprise heavy chain CDR1 comprising SEQ ID NO: 8; heavy chain CDR2 comprising SEQ ID NO: 9; heavy chain CDR3 comprising SEQ ID NO: 10; light chain CDR1 comprising SEQ ID NO: 11; light chain CDR2 comprising SEQ ID NO: 12; and light chain CDR3 comprising SEQ ID NO: 13.

As used herein, the phrase "prognosing progression of a cancer" refers to evaluating indicia of a cancer disease at a given time point and comparing the same to the indicia of the cancer disease taken at an earlier time point, wherein the comparison is indicative of a progression of the cancer in the subject. In some embodiments, progression of the cancer comprises metastasis of the cancer in the subject.

As such, the antibody, or the fragment or derivative thereof, of the presently disclosed subject matter can be employed to detect the presence of circulating tumor cells (CTCs) in the blood or other biological samples of cancer patients, as the presence of CTCs can be an important indicator of the potential for metastatic disease and poor prognosis. Currently, the CELLSEARCH® system (Veridex, LLC, Raritan, N.J., United States of America) is the only method approved by the United States Food and Drug Administration (FDA) to measure CTCs in metastatic breast, colorectal, and prostate cancer patients. This system is based on the detection of the epithelial cell surface marker EpCAM in CTCs. In metastatic breast cancer, detection of CTCs before initiation of first-line therapy has been shown to be highly predictive of progression free survival and overall survival. Patients with >5 CTCs per 7.5 ml of blood at baseline and at first follow-up (4 weeks) had a worse prognosis than patients with less than five CTCs (Cristofanilli et al., 2005). Similarly, in pancreas cancer, >1 CTCs/7.5 ml of blood correlated with poor prognosis (Kurihara et al., 2008).

However, the ability of CTCs to form actual metastatic lesions remains in question. Since tumor cells with invasive phenotypes lose several epithelial antigens in a transformation process called epithelial-mesenchymal transition (EMT), EpCAM-expressing CTCs are currently minimally predictive of metastasis. In fact, low EpCAM expression by micrometastases has been reported, and attempts to isolate CTCs using antibodies against EpCAM have not been successful to date. Since MUC1-expressing cells have high metastatic potential and MUC1 has been found to be expressed on CTCs, the presently disclosed antibodies, and the fragments and derivatives thereof, including but not limited to the TAB-004 antibody, can serve as a highly reliable and improved predictor of metastasis compared to strategies based on attempting to detect EpCAM-expressing CTCs.

VII. Other Uses

The antibodies of the presently disclosed subject matter can also be employed in various assay methods, such as but not limited to competitive binding assays, direct and indirect sandwich assays, and immunoprecipitation assays (see e.g., Zola, 1987; Harlow & Lane, 1988).

The antibodies of the presently disclosed subject matter also are useful as affinity purification agents. In this process, one or more antibodies are immobilized on a suitable support (such as, but not limited to a Sephadex resin or filter paper) using methods well known in the art. See e.g., Harlow & Lane, 1988.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Generation of Pancreatic Adenocarcinoma Mice Expressing Human MUC1

Figure 3:
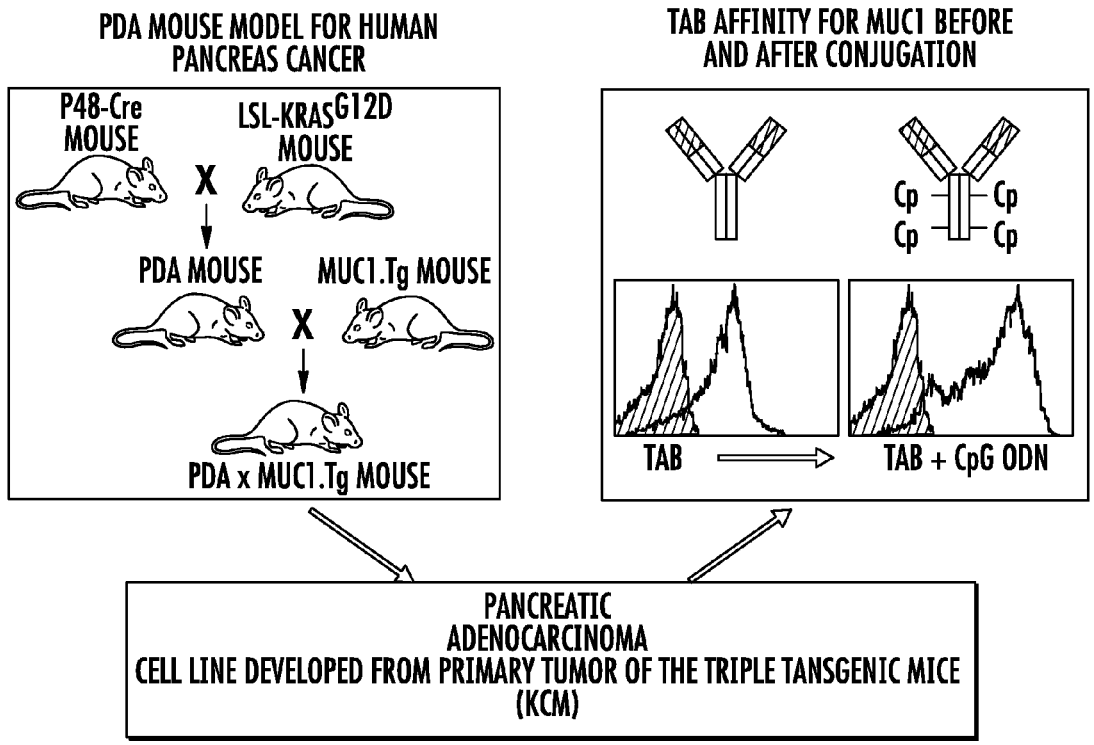
FIG. 3 is a schematic (upper left panel) showing an approach for creating a triple transgenic mouse line that expresses the Cre recombinase throughout the pancreas, a mutated K-ras oncogene polypeptide, and a human MUC1 polypeptide. This mouse develops pancreatic adenocarcinoma, cells of which were used to generate the primary tumor cell line KCM (lower panel). The KCM cell line was used to test the binding of an exemplary antibody of the presently disclosed subject matter (denoted in the Figure as "TAB" and in the instant disclosure as "TAB-004") either alone or conjugated to CpG oligodeoxynucleotides (CpG ODN). It was determined that both the unconjugated and conjugated antibodies bound to the KCM pancreatic cell line with equal affinity (upper right panel).

A strategy for generating a triple transgenic mouse line that expressed human MUC1 and develops pancreatic adenocarcinoma is depicted in FIG. 3. Briefly, P48$^{Cre/+}$ mice, which expressed the Cre recombinase throughout the developing and adult pancreas (Kawaguchi et al., 2002) were bred to LSL-Kras$^{G12D/+}$ mice, which contained a transcriptionally inactive K-ras$^{G12D}$ allele that was activated in cells expressing Cre (Jackson et al., 2001; Kawaguchi et al., 2002). The progeny that were positive for both P48$^{Cre/+}$ and LSL-Kras$^{G12D/+}$ (designated "PDA mice") were mated to a transgenic mouse line (MUC1.Tg) that carried a human MUC1 transgene and were maintained as heterozygotes (see FIG. 3). MUC1.Tg mice expressed human MUC1, exhibited B- and T-cell compartment tolerance, and were refractory to immunization with the protein encoded by the transgene (Rowse et al., 1998). Since the human MUC1 transgene was driven by its own promoter in these mice, its expression levels were tissue-specific and appropriate. Low-level luminal surfaces of simple epithelial tissue and increased expression in tumors were observed.

Figure 1B:
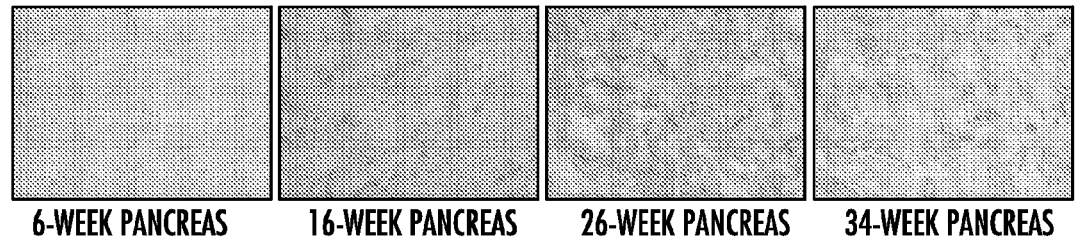

Mice that were positive for P48$^{Cre/+}$, LSL-Kras$^{G12D/+}$, and human MUC1 (referred to herein as "PDA.MUC1.Tg" mice) carried three transgenes. All PDA×MUC1.Tg mice developed pancreatic intraepithelial neoplasia (PanINs) of different stages including PanIN-IA, PanIN-IB, PanIN-2, PanIN-3, and adenocarcinoma (Tinder et al., 2008; Mukherjee et al., 2009). Representative sections from various ages of the PDA×MUC1.Tg pancreas are shown in FIG. 1B. Approximately 80% of these mice developed adenocarcinoma by 26 weeks of age, and almost 100% of the mice developed adenocarcinoma by 34 weeks of age.

From the PDA.MUC1.Tg mice (FIG. 3) that expressed human MUC1 and mutated K-ras$^{G12D}$ tumor antigens, protein lysates were prepared in order to produce antisera to tumor-associated antigens expressed by the triple transgenic mice. Briefly, 5 mgs of the protein lysate was mixed with Incomplete Freund's Adjuvant (IFA) and used to immunize Balb/c mouse. Hybridomas were generated by fusion of spleen cells from immunized mice with myeloma cells, and the TAB-004 antibody was identified by screening hybridomas. This monoclonal antibody was determined to be of the IgG isotype. The purified antibody bound to tumor-associated glycosylated MUC1.

Figures 2A, 2B:
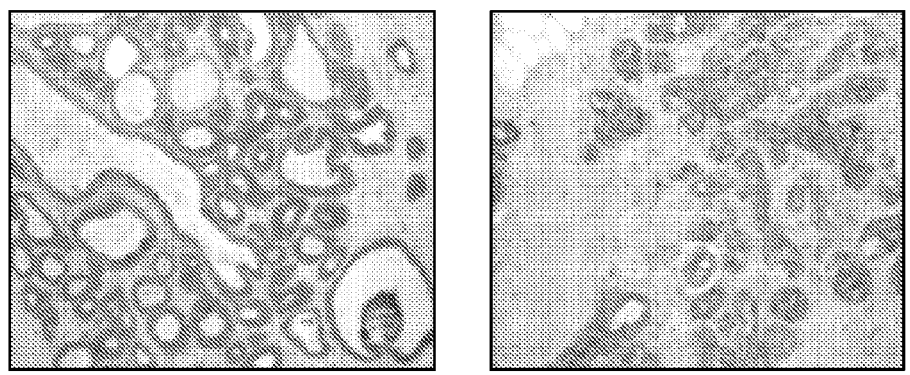
FIGS. 2A-2C are a series of photomicrographs depicting specific binding of an exemplary antibody of the presently disclosed subject matter to human breast tumor tissue (FIGS. 2A and 2B) but not to adjacent normal breast tissue (FIG. 2C).
Figure 2C:
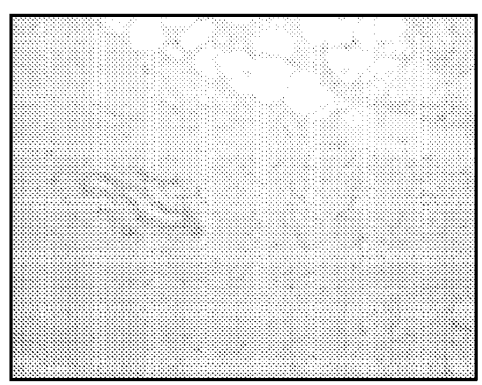

Epitope screening determined that the TAB-004 monoclonal antibody (mAb) described herein bound to an epitope present within SEQ ID NO: 3. The antibody reacted strongly with tumor tissue isolated from human pancreas (FIG. 1B), human breast (FIGS. 2A and 2B), but did not bind appreciably to normal pancreas or breast tissue (see FIGS. 1A and 2C).

Interestingly, the TAB-004 antibody cross reacted with mutated K-ras such that tumor tissues expressing the K-ras mutation but not human MUC1 also showed positive staining with the antibody. All metastatic lesions showed positive reactivity, and it appeared that TAB-004 could bind to an epitope present within a mutated K-ras polypeptide.

Example 2

FACS Sorting of Tumor Cells

The TAB-004 antibody was tested with various samples to determine its ability to bind to and sort tumor cells that were present in different environments and under different conditions using Fluorescence Activating Cell Sorting (FACS).

In a first experiment, the TAB-004 antibody was employed for staining cells from purified populations of CD133$^+$ and CD24$^+$/CD44$^+$/EpCAM$^+$ cells. Sections from pancreatic adenocarcinomas are mechanically homogenized and digested in collagenase IV and DNase for 30 minutes at 37° C. Whole blood and single cell suspension from the tumor were subjected to lineage cell depletion using the Lineage Cell Depletion Kit (Miltenyi Biotec, Bergisch Gladbach, Germany, Catalogue No. 130-092-211), thus removing cells expressing the following lineage antigens: CD2, CD3, CD11b, CD14, CD15, CD16, CD19, CD56, CD123, and CD235a from the cell suspensions. Lineage negative (lin$^-$) cells from blood samples or tumor samples from patients with pancreatic cancer were then screened using flow cytometry for cells expressing MUC1, using the TAB-004 antibody, and the following pancreatic stem markers CD133 (AC133) or CD24$^+$/CD44$^+$.

Figure 7A:
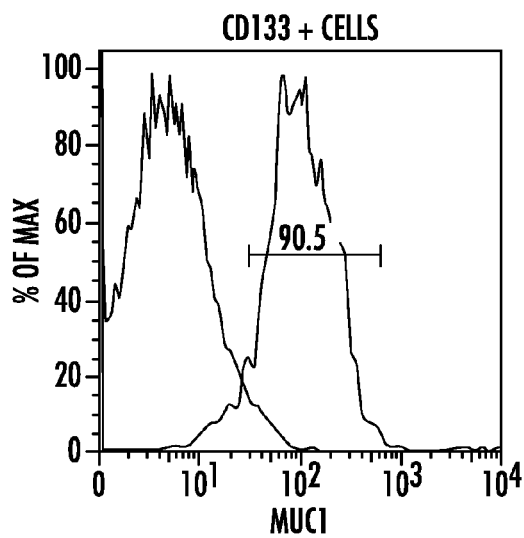
FIGS. 7A and 7B are histograms of fluorescence-activated cell sorting (FACS) separations of $CD133^+$ (FIG. 7A) versus $CD24^+/CD44^+/EpCAM^+$ (FIG. 7B) cells and the extent to which the TAB-004 antibody disclosed herein bound to these populations. The left trace in each panel corresponds to sorting with a negative control antibody, and the right trace in each panel corresponds to sorting with the TAB-004 antibody.
Figure 7B:
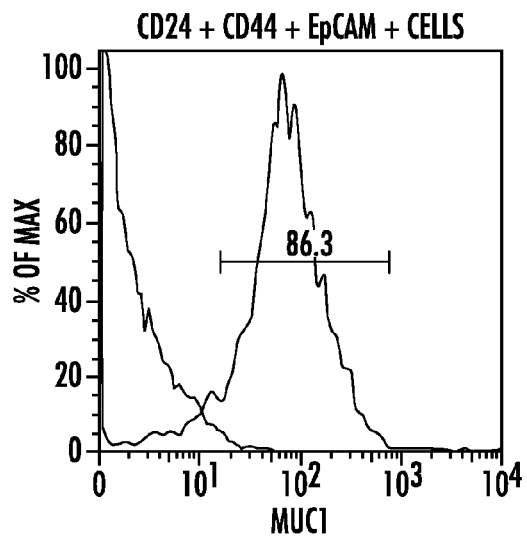
Figure 8A:
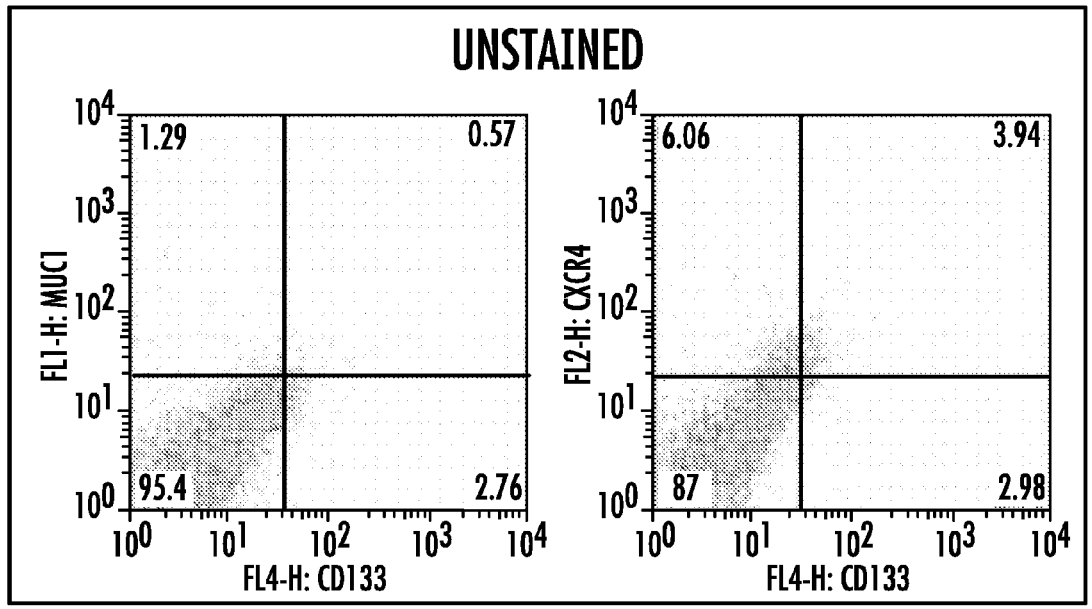
FIGS. 8A-8D are FACS scatter plots showing binding of the TAB-004 antibody to a pancreatic tumor ("Tumor1") and adjacent normal tissue ("Normal") using the TAB-004 antibody and an antibody directed against the CXC chemokine receptor 4 (CXCR4). MUC1: TAB-004 antibody; CXCR4: anti-CXCR4 antibody; FL1-H: Flourescent stain 1 height (Flourescein-FITC); FL2-H: Flourescent stain 2 height (Phycoerythrin-PE); SSC-H: side-scatter height; FSC-H: forward-scatter height; FL4-H: Flourescent stain 4-height (Allophycocyanin-APC).
Figure 8B:
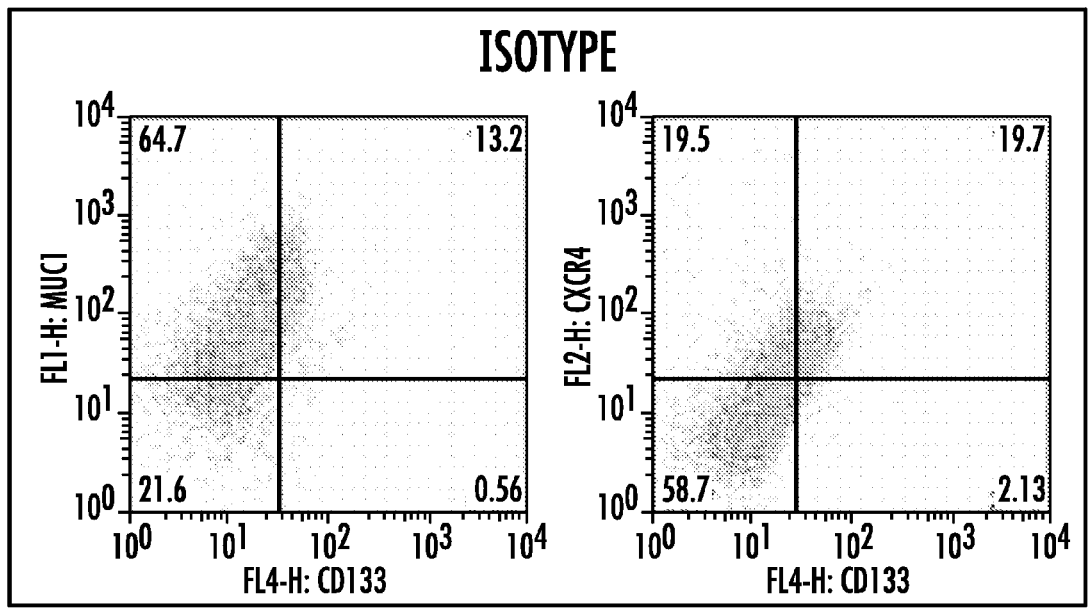
Figure 8C:
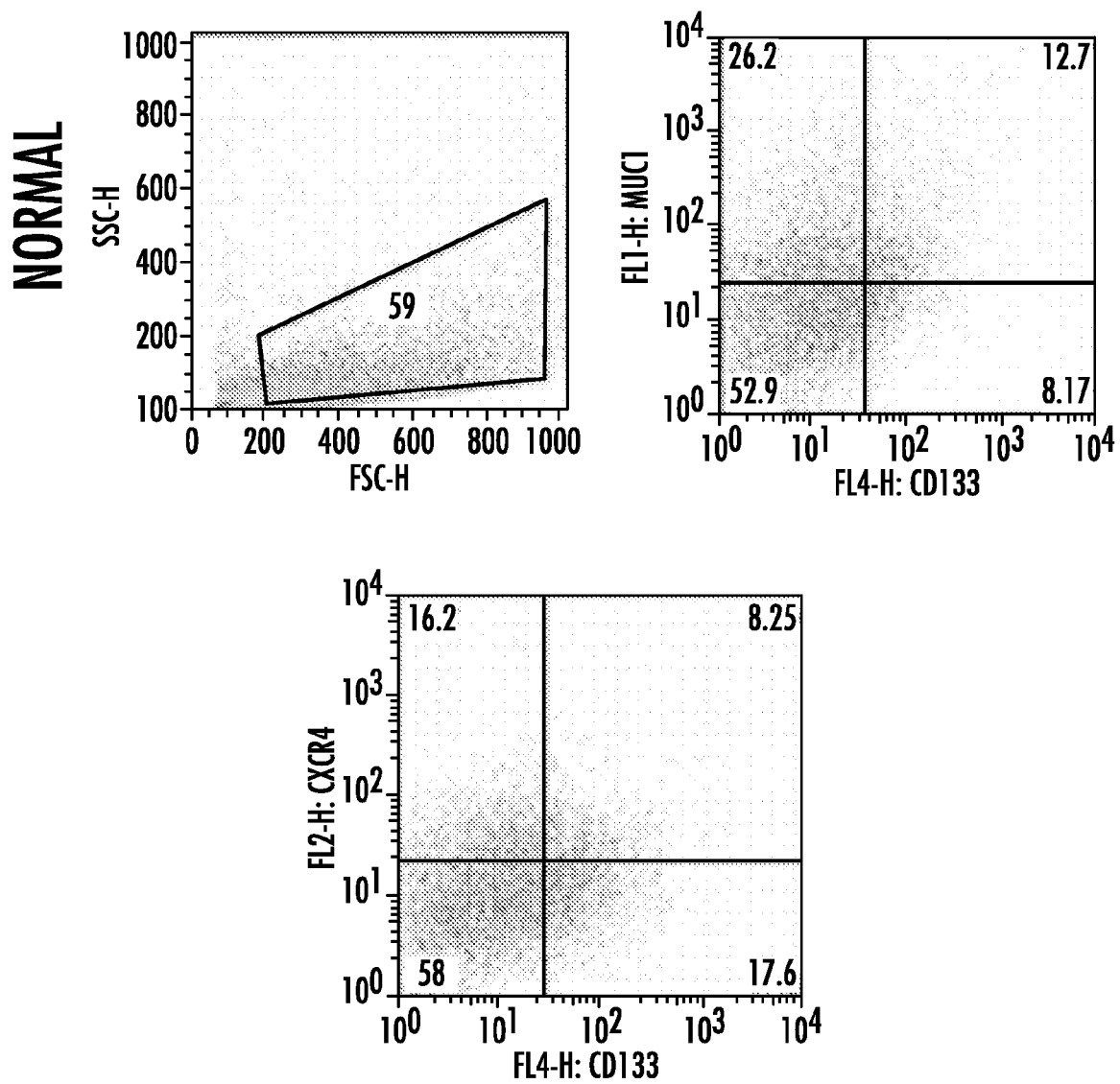
Figure 8D:
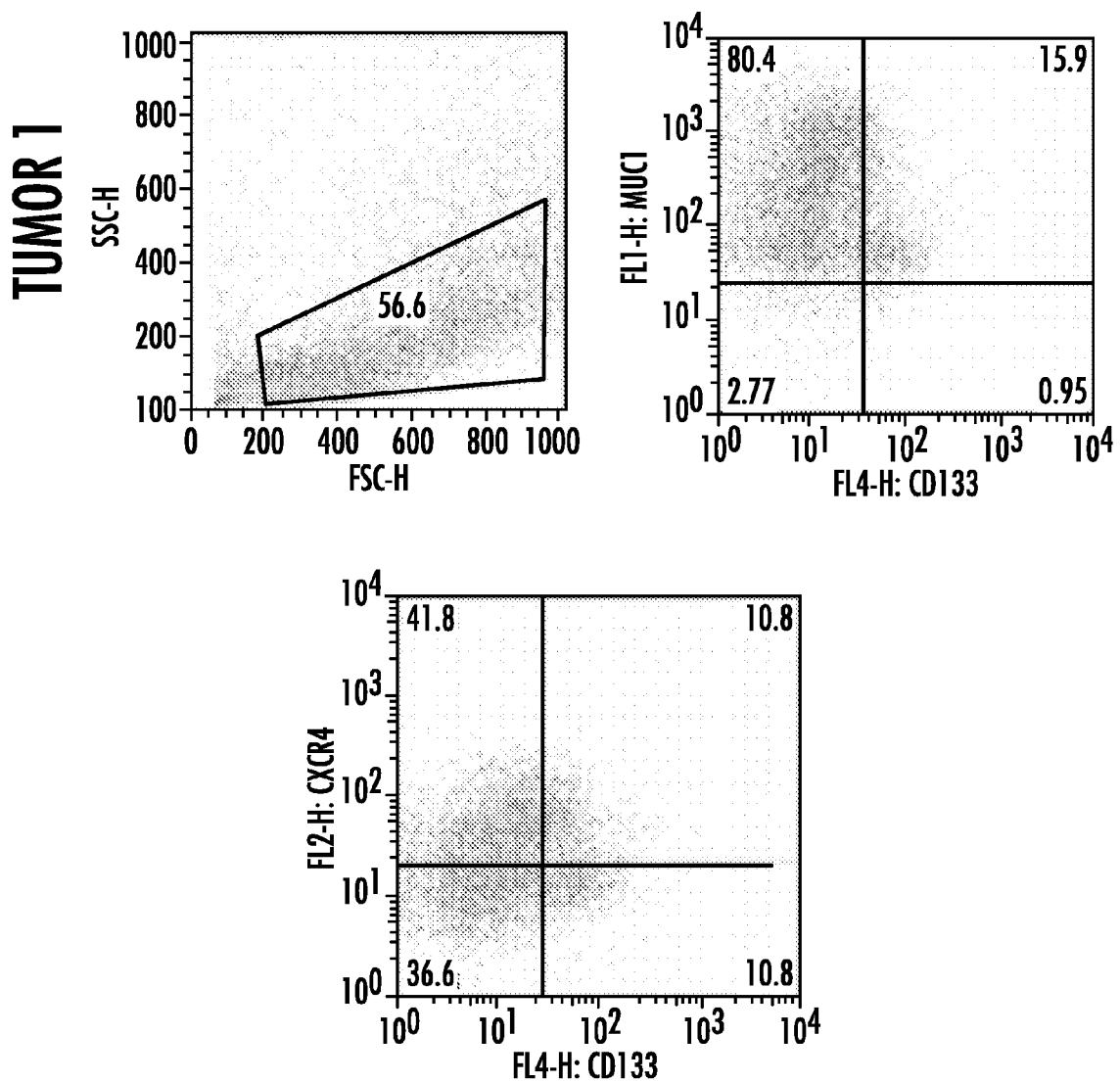

FIGS. 7A and 7B are histograms of fluorescence-activated cell sorting (FACS) separations of CD133$^+$ (FIG. 7A) and CD24$^+$/CD44$^+$/EpCAM$^+$ (FIG. 7B) cells and the extent to which the TAB-004 antibody disclosed herein bound to these populations.

Next, FACS analysis was employed to compare MUC1 expression using the TAB-004 antibody in normal and pancreatic tumor cells isolated from pancreatic tumor tissues, and also the expression of CXCR4, a polypeptide that has been associated with mobility of cells including cancer cells. The results are shown in FIG. 8.

In FIG. 8, the distributions of cells in histologically normal pancreatic tissue (FIG. 8C) versus adjacent pancreatic adenocarcinoma tissue (FIG. 8D) stained with the TAB-004 antibody versus a CXCR4 antibody was compared. As can be seen, cells that were positive for MUC1 or for CXCR4 were more abundant in pancreatic adenocarcinoma tissue than in histologically normal adjacent pancreatic tissue. FIGS. 8A and 8B show the results of negative controls (FIG. 8A—no antibody; FIG. 8B—isotype control antibody).

Figure 9A:
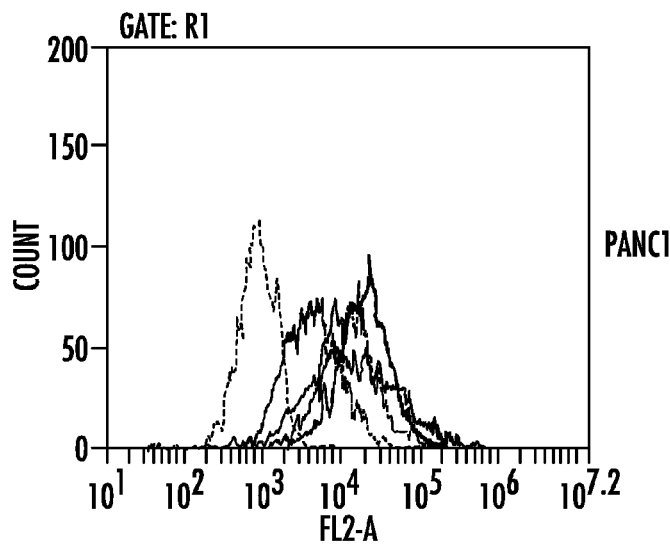
FIGS. 9A-9C are a series of FACS plots that show that the TAB-004 antibody of the presently disclosed subject matter is superior to a standard EpCAM antibody in detecting circulating tumor cells in pancreatic cancer patients. Unstained cells (left most black lines); EpCAM-PE (0.1 mg/ml) stained cells (dark gray lines); TAB-004-PE (0.1 mg/ml) stained cells (right most black lines); TAB-004-PE (0.02 mg/ml) stained cells (light gray lines); TAB-004-PE (0.004 mg/ml) stained cells (medium gray lines). "-PE" indicates that the antibodies were labeled with phycoerythrin for the purposes of sorting.

And finally, the TAB-004 antibody was compared to an EpCAM antibody that is currently in use for detecting epithelial cancers. FIG. 9 provides a series of FACS plots that show that the TAB-004 antibody was superior to a standard EpCAM antibody in detecting circulating tumor cells in pancreatic cancer patients.

First, whole blood from a normal control individual was spiked with 250 cells of the PANC1 pancreatic cancer cell line per 700 ml of blood, and the PANC1 cells were stained using the TAB-004 antibody. Comparison of the right-most black, light gray, and medium gray lines, which correspond to three different concentrations of TAB-004 antibody ranging from 0.1 mg/ml to 0.004 mg/ml, to the dark gray line, which corresponds to the EpCAM antibody, shows that all four of these preparations were able to detect the PANC1 cells in these preparations reasonably well.

Figure 9B:
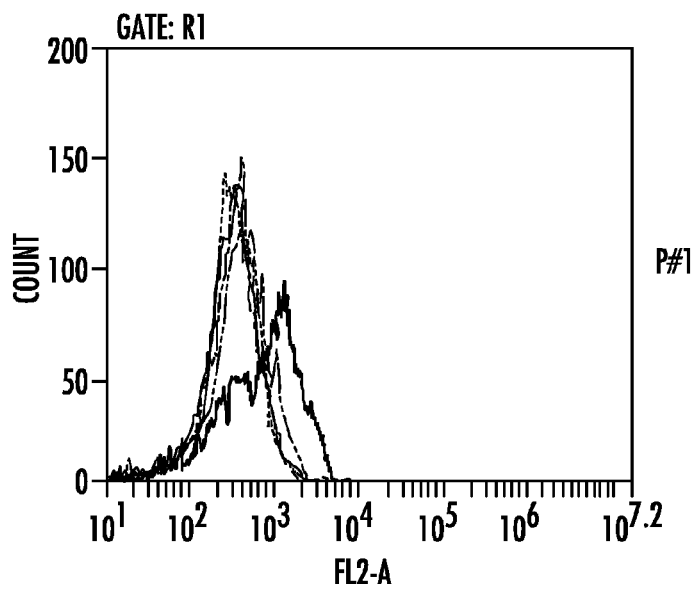
Figure 9C:
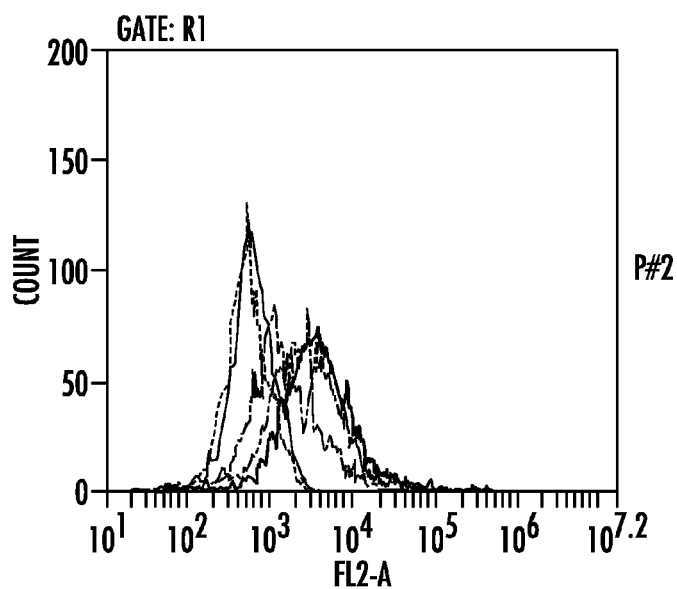

Next, the abilities of the TAB-004 and EpCAM antibodies to detect circulating tumor cells present in the blood from two patients (patient number 1 and patient number 2, respectively) was tested. As shown in FIGS. 9B and 9C, there was a clearly observable difference between the TAB-004 antibody and the EpCAM antibody to detect circulating tumor cells in patient blood. Particularly, the TAB-004-PE antibody (see the right-most black line in FIG. 9B and the right-most black and light gray lines in FIG. 9C) but not the EpCAM-PE antibody (see the dark gray line in FIGS. 9B and 9C) was able to detect these circulating cells in the blood of patients, suggesting that the TAB-004 was far superior to the currently used EpCAM antibody for this purpose.

Example 3

Production of TAB-004 Conjugates

The TAB-004 antibody of the presently disclosed subject matter was conjugated to 1-methyl-DL-tryptophan (1MT), an indoleamine 2,3-dioxygenase (IDO) inhibitor; an EP2/EP4 receptor antagonist; and CpG oligodeoxynucleotides (CpG ODN), which function as dendritic cell activators (Rothenfusser et al., 2002). Data on the functional role of the TAB-004 antibody conjugated to CpG ODN is provided herewith as a non-limiting example of the functionality of the antibodies and conjugates of the presently disclosed subject matter.

Figure 4A:
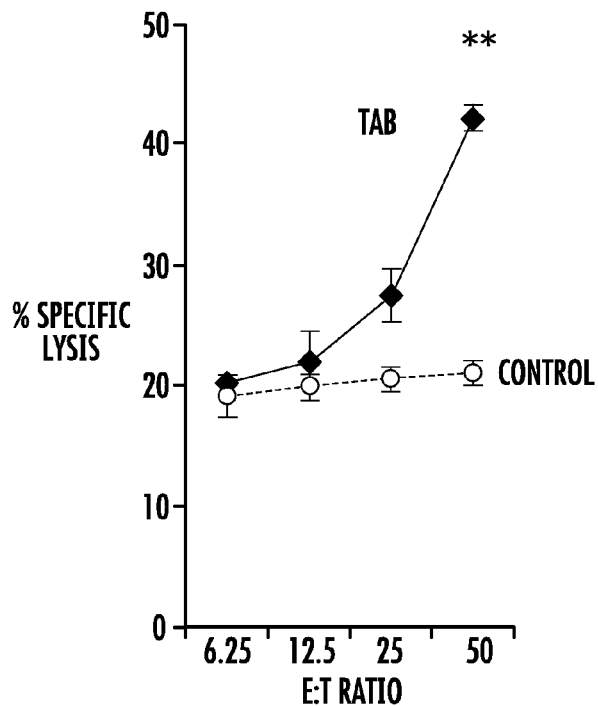
FIGS. 4A and 4B are graphs showing that an exemplary antibody of the presently disclosed subject matter (TAB-004) enhanced the cytotoxicity of Natural Killer (NK) cells to kill target tumor cells. Conjugation of the antibody to CpG ODN further enhanced this effect, thereby demonstrating that the exemplary antibody was capable of enhancing an anti-tumor immune response in vivo.
Figure 4B:
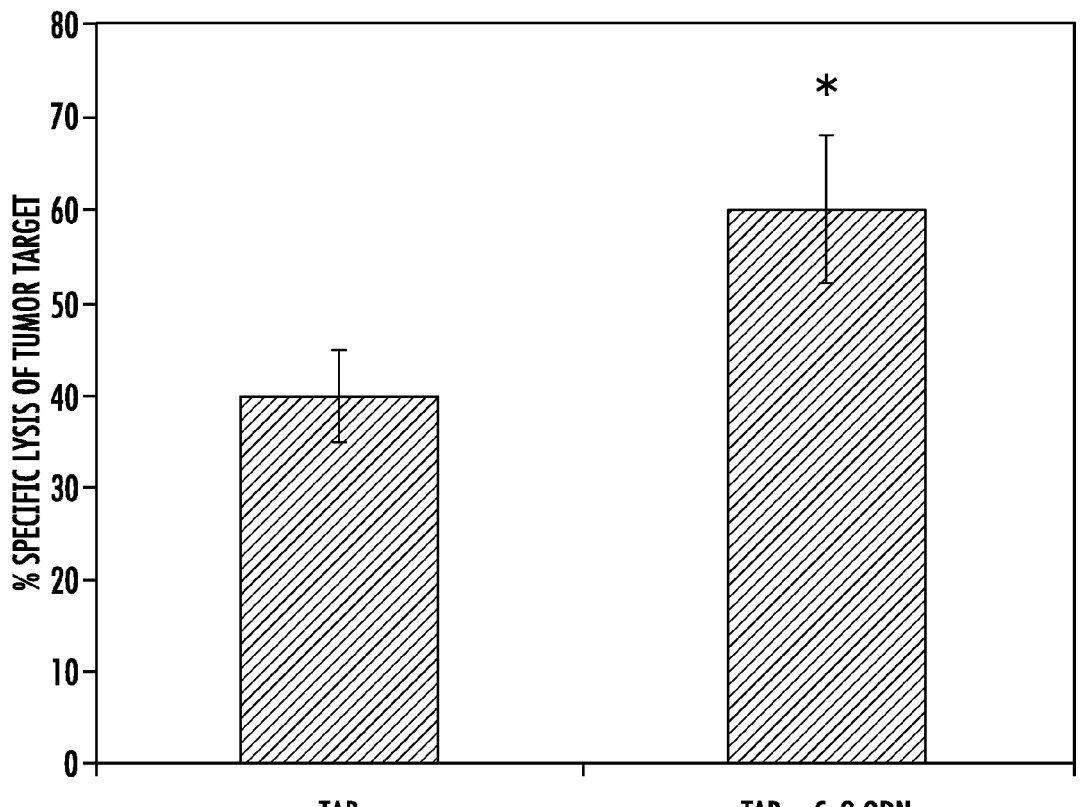

The TAB-004 antibody alone or conjugated to CpG ODN bound to a tumor cell line (referred to herein as the "KCM" cell line; see FIG. 3) generated from the triple transgenic PDA.MUC1.Tg mice. While applicants do not wish to be bound by any particular theory of operation, it appeared that the antibody activated natural killer cells (NK cells) and conjugation with CpG ODN further enhanced the NK cell lytic activity against its targets such as YAC cells as well as the KCM cells lines (see FIG. 4).

Example 4

In Vivo Anti-Tumor Activity of the TAB-004-CpG ODN Conjugate

Figure 5A:
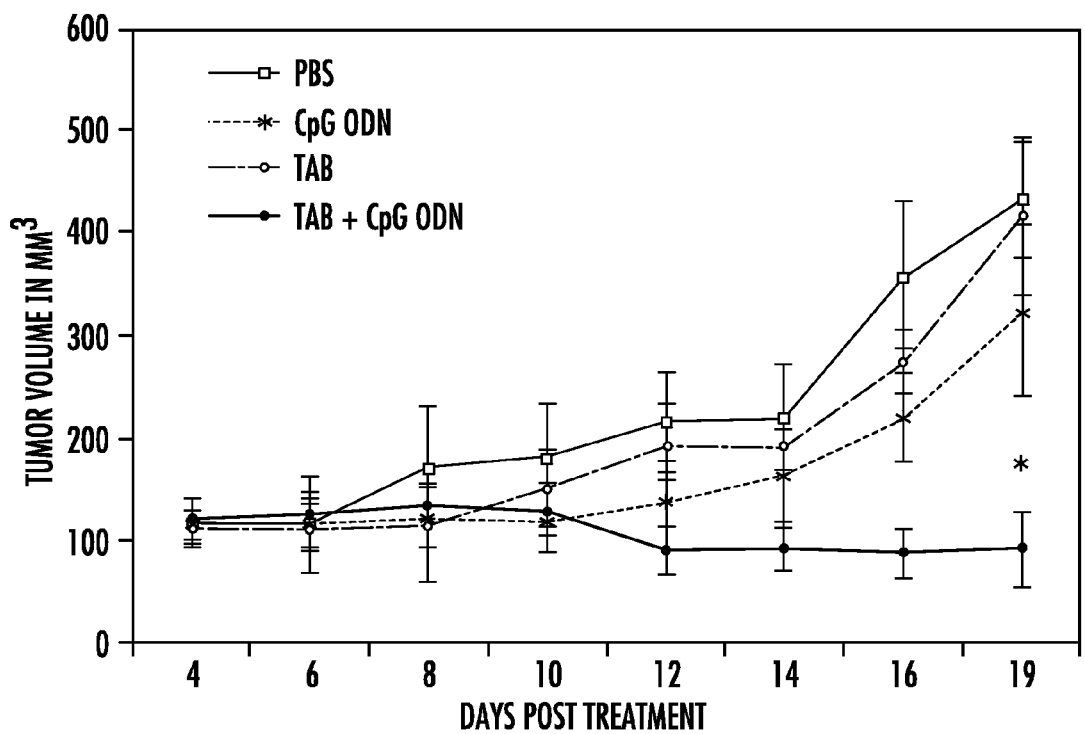
FIGS. 5A and 5B illustrate the results of experiments designed to test the ability of an exemplary antibody of the presently disclosed subject matter (TAB-004), and conjugates thereof, to reduce tumor volume of an established KCM tumor in MUC1 transgenic (MUC1 Tg) mice.
Figure 5B:
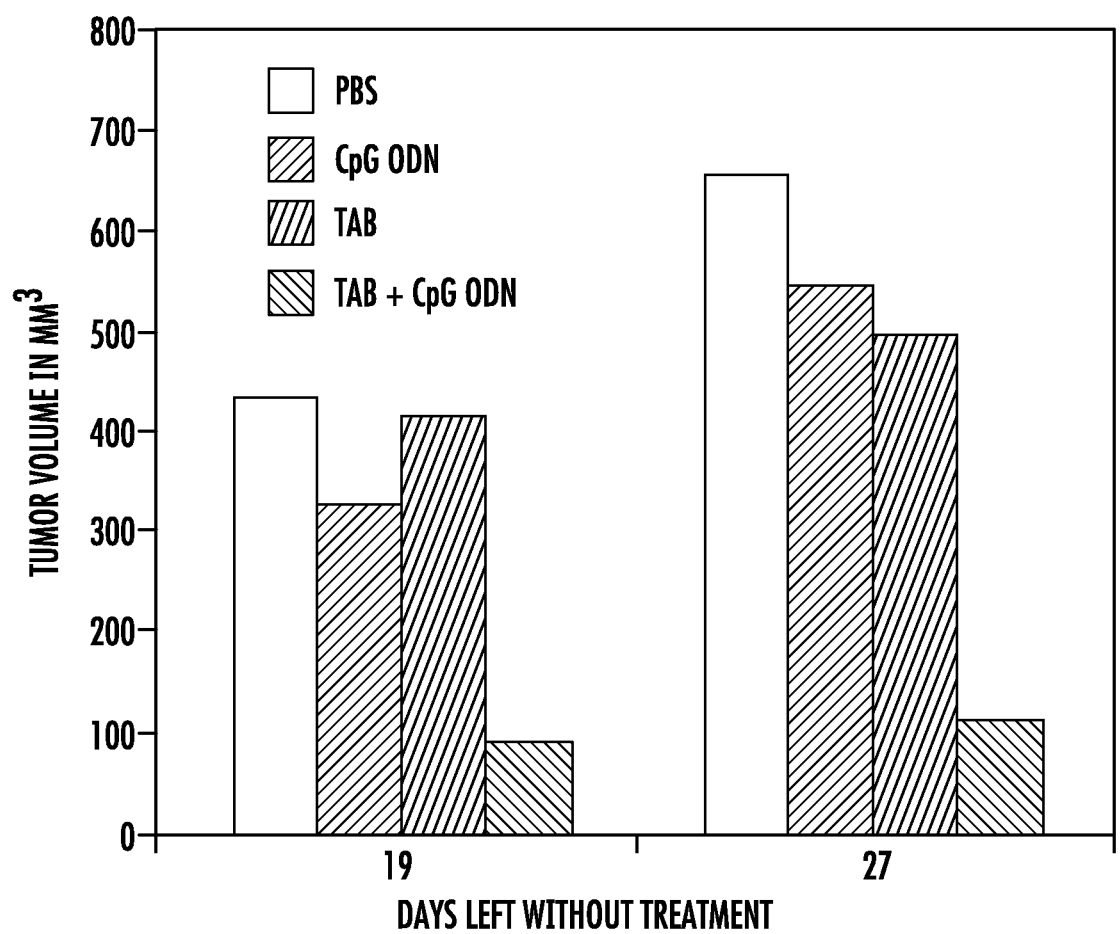

Ten (10) mice were injected with the KCM established pancreatic cancer cell line generated from the triple transgenic PDA.MUC1.Tg mice. The treatment groups and the schedule and dose were as illustrated in FIGS. 5A and 5B. Briefly, 3×10⁶ KCM tumor cells were administered subcutaneously into the flank region of mice (n=10 mice) at day 0. At days 4, 10, and 16, 50 µg of a TAB-004-CpG ODN conjugate were administered intratumorally (without adjuvant) to each mouse. The same amounts of antibody were administered to an antibody alone group (unconjugated TAB-004) for comparison. Mice were sacrificed at day 20 and tumors recovered.

As shown in FIG. 5, treatment with the conjugated antibody completely stopped the growth of an established tumor leading to complete eradication. The data also showed that even after cessation of treatment, the mice treated with the TAB-004-CpG ODN conjugate did not grow back the tumors (see FIG. 5), supporting the use of the TAB-004-CpG ODN conjugate as a vaccine for cancer such as, but not limited to epithelial cancers, particularly pancreatic cancers.

Example 5

Antibody Cloning, Recombinant Antibody Production, Antigen Binding Confirmation, and Sequencing of (CDRs)

In order to confirm the ability of the TAB-004 antibody to bind to MUC1 and to determine the amino acid sequences of the CDRs, total RNA was extracted from hybridoma cell line ATCC No. PTA-11550 and reverse transcription PCR (RT-PCR) was performed using immunoglobulin heavy- and light chain-specific primer sets and a QIAGEN® OneStep RT-PCR Kit. For each set, multiple heavy chain and light chain RT-PCR reactions were performed using degenerate forward primer mixtures covering the leader sequences of variable regions. Forward primers were used at different concentrations, while reverse primers (located in the constant regions of the heavy or light chain genes) were 50 ng per reaction. The following RT-PCR conditions were employed:
    Reverse transcription: 30 minutes at 50° C.;
    Initial PCR activation step: 15 minutes at 95° C.;
    Cycling: 20 cycles of 94° C. for 25 seconds;
        54° C. for 30 seconds;
        72° C. for 30 seconds;
    Final extension: 10 minutes at 72° C.

Next, second-round semi-nested PCR was employed. The forward primers were identical to the ones used in the first-round RT-PCR, although the amount of each primer was doubled relative to the RT-PCR conditions described above. Semi-nested reverse primers specific for heavy chain sequecnes were used at 100 ng per reaction. The PCR conditions employed were as follows:
    Initial denaturing of 5 minutes at 95° C.;
    Cycling: 25 cycles of 95° C. for 25 seconds;
        57° C. for 30 seconds;
        68° C. for 30 seconds;
    Final extension: 10 minutes at 68° C.

After the PCR was completed, samples of the PCR products were separated on agarose gels and products were visualized. Several heavy chain and light chain PCR products were subcloned and the variable regions of the heavy and light chains were sequenced. The resulting nucleotide sequences, and the amino acid sequences encoded thereby, are shown in SEQ ID NOs: 4-7, and the amino acid sequences of the CDRs deduced therefrom are summarized in Table 4.

TABLE 4

Amino Acid Sequences of the CDRs of the Heavy and Light Chains of the TAB-004 Monoclonal Antibody

| IgG Chain | CDR1 Sequence | CDR2 Sequence | CDR3 Sequence |
|---|---|---|---|
| Heavy | GYTFTNYW (SEQ ID NO: 8) | INPSSGYT (SEQ ID NO: 9) | STYYGDYLFPY (SEQ ID NO: 10) |
| Light | QDIVYGNGNTY (SEQ ID NO: 11) | KVS (SEQ ID NO: 12) | FQGSHVPYT (SEQ ID NO: 13) |

Next, recombinant antibodies were produced by another round of RT-PCR amplification of the total RNA isolated from the hybridoma cell line ATCC No. PTA-11550 followed by second-round semi-nested PCR as set forth herein above. Amplified heavy chain sequences and light chain sequences were individually subcloned into plasmid antibody expression vectors.

Next, the plasmids from were transfected into CHO cells, and recombinant IgG having a human IgG1 backbone were produced. Supernatants from transfected CHO cells were tested for antigen binding in 96-well ELISA format. Several supernatant samples showed very strong binding, although the concentrations of the recombinant IgG in the supernatants were low (i.e., about 10 ng/ml). Given the relatively low concentration of antibody in the supernatant, the ELISA results indicated that the recombinant antibodies were very potent.

The sequences of the inserts of the recombinant antibody plasmids were determined by DNA sequencing. All corresponded to a single heavy chain sequence and a single light chain sequence. The nucleotide and amino acid sequences of the variable regions of the heavy and light chains were determined, and the CDR sequences deduced therefrom were as set forth in SEQ ID NOs: 8-13.

Example 6

Comparison of the Performance of the TAB-004 Antibody to Other Tumor Antigen-Based Detection Strategies in Breast and Pancreatic Cancers Clinical blood-based tests for tumor antigens currently available include CA 15-3 and CA 27-29 for breast cancer and CA 19-9 for pancreatic cancer. Non-cancerous conditions or benign disease can lead to elevated levels of these tumor antigens, thus negatively impacting the ability of these antibodies to be used for accurately detecting cancers. As a result of this low specificity, these tests have yet to be proven to be of significant diagnostic value.

To that end, the ability of TAB-004 to detect levels of shed MUC1 in the plasma of patients was compared to the performances of these antibodies in plasma samples. An enzyme immunoassay (EIA) has been optimized using the TAB-004 antibody to capture and detect levels of shed MUC1 present in circulation. Briefly, a 96-well ELISA plate was coated with 100 µl of TAB-004 antibody at 50 µg/mL in PBS and incubated overnight at 4° C. Following incubation, excess TAB-004 capture antibody was removed from the plate. The plate was blocked with 200 µl of 1% dry milk in PBS to avoid non-specific binding and incubated for 1 hour at 4° C. The plates were washed extensively (3 times) with 250 µl PBS containing 0.05% (v/v) TWEEN®-20 using an ELISA plate washer. A MUC1 standard using a 25-mer polypeptide preparation from MUC1 TR was prepared ranging from 0-2000 U/ml. The test plasma was diluted 1:2, and 1:10 in 0.1% milk in PBS, and 100 µl ws added to the appropriate wells in triplicate, and the plates were incubated for 2 hours at 37° C.

Plates were then washed and 100 µl of a polyclonal rabbit anti-MUC1 antibody (Genway) were added at 1:300,000 dilution in 0.1% milk in PBS to each well, and the plate was incubated for 1 hour at 37° C. The polyclonal antibody was washed from the wells and horse radish peroxidase-labeled goat anti-rabbit IgG was added at a 1:1,000 dilution in 0.1% milk in PBS and incubated at 37° C. for 1 hour. After washing the plates, 100 µL of a solution consisting of peroxidase substrate (TMB) was added to the wells, and the plates incubated at room temperature for 30 minutes in the dark. The reaction was stopped by the addition of 25 µl of 4.0 N sulfuric acid, and the optical density read at a wavelength of 450 nm using a SPECTRA-MAX 250 spectrophotometer. Standard curves were generated with regression analyses to determine concentrations of the unknown samples.

Arbitrary units (U)/ml wer chosen based on an initial reference standard of MUC1. A linear range was determined to be 50-800 units/ml of MUC1 antigen. Intra- and inter-assay variations were controlled by including normal and abnormal samples to ensure the equipment, the technologist, and the reagents used in the test were performing as expected.

The TAB-004 EIA assay was compared against CA15-3 (Abbott Laboratories, Abbott Park, Ill., United States of America) breast cancer samples. Comparison to CA27-29 (Bayer Diagnostics, Tarrytown, N.Y.) for breast cancer and to CA19-9 (Panomics Inc, Redwood City, Calif., United States of America) for pancreatic cancer samples using EIA assays are also performed. Statistical analyses were conducted to assess the sensitivity and specificity of TAB-004 EIA versus the commercially available EIAs.

The TAB-004 EIA was employed using plasma from 36 breast cancer patients, 24 prostate cancer patients, 4 pancreatic cancer patients, 13 esophageal cancer patients, 12 normal controls, 3 patients with pancreatitis, and 1 diabetic patient (pancreatitis and diabetes are two conditions known to detect as falsely positive using the assays that test for the presence of the CA 15-3, CA 27-29, and CA 19-9 antigens). Most cancer samples that were tested were from late stage cancers.

The cutoff value of <40 U/ml was reached from preliminary data for normal patients (n=12). Mean and standard deviation values of 17.42 and 7.07 units/ml of plasma respectively were found (see FIG. 10). Going into this study, we plan on using a value of less than 40 units/ml of plasma as normal. This would cover more than 99.8% of the population assuming a normal distribution. We plan on refining the cut-off value as part of this study given that we had only 12 samples in our preliminary data which has likely artificially inflated the standard deviation.

Figure 10:
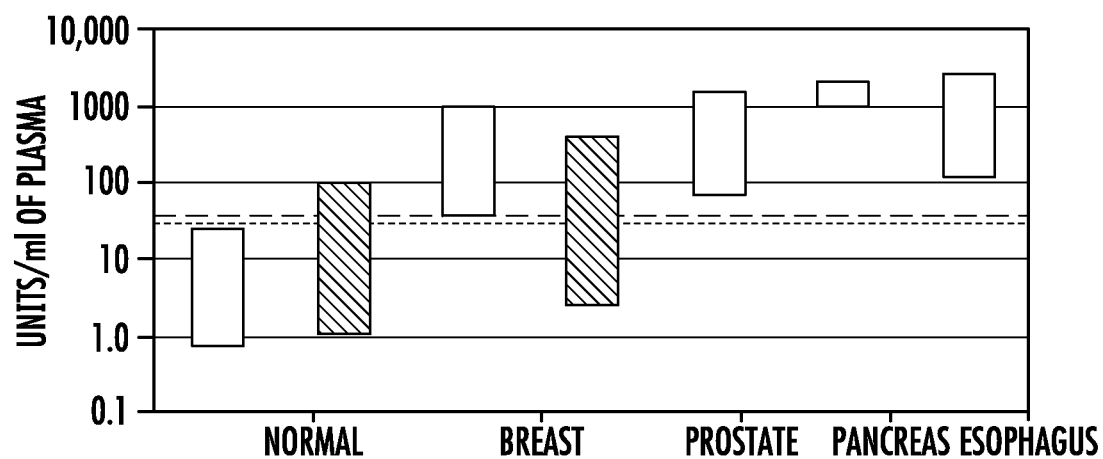
FIG. 10 is a bar graph of a comparison of performance of an antibody specific for the CA 15-3 antigen with TAB-004 in an enzyme immunoassay (EIA) for detecting cancer cells in plasma. White boxes: TAB-004 antibody. Black boxes: CA15-3. Dashed line: TAB-004 normal cutoff; dotted line: CA 15-3 normal cutoff.

At this cutoff value of <40 U/ml, none of the healthy or pancreatitis plasma were positive, while all plasma from cancer samples were >40 U/ml (see FIG. 10). The data demonstrated that compared to an assay that is designed to detect the CA 15-3 antigen, the TAB-004 EIA assay was superior in detecting more specifically and with higher sensitivity the tumor antigen in the plasma from breast cancer patients versus plasma from normal volunteers. While there were no false positives with TAB-004, 5 out of 12 normal patients produced false positive results with the CA15-3-based assay (p=0.031, using one-tailed test; <31 U/ml, is the published cutoff value for the CA15-3-based assay). All cancer patient plasma was positive for TAB-004 but 3 out of 36 plasma samples showed false negative with CA-15-3 (<31 U/ml). Overall, the difference between plasma from cancer versus normal was much larger with TAB-004 when compared with CA15-3 test in the breast cancer patients. There was also considerable overlap between normal and cancer plasma when CA 15-3 test was used whereas there was no overlap when TAB-004 test was used (see FIG. 10).

Figure 11:
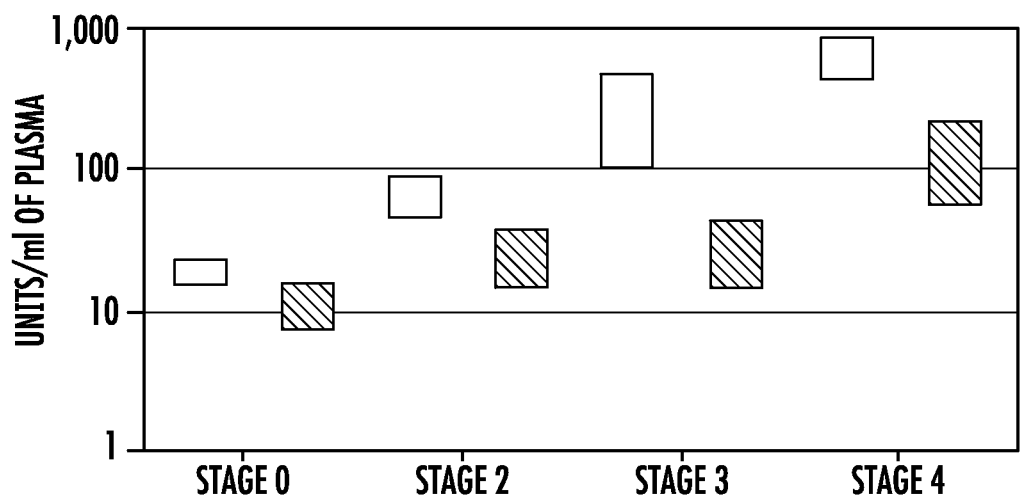
FIG. 11 is a bar graph of a comparison of performance of TAB-004 in an enzyme immunoassay (EIA) for detecting levels of shed MUC1 in plasma of pancreatic patients as a function of stage compared to a CA15-3-based EIA. White boxes: TAB-004 antibody. Black boxes: CA15-3.

To further evaluate the performance of the TAB-004 antibody to assess disease stage, the TAB-004 EIA was performed on plasma samples from n=5 stage 0, 2, 3, and 4 pancreatic cancer patients. FIG. 11 shows that the mean differences between the TAB-004 and CA 15-3 assays were statistically significant for all 4 cancer stages (stage 0 p=0.049; stage 2 p=0.008; stage 3 p=0.017; and stage 4 p=0.008). The TAB-004 assay provided values that were higher than CA 15-3 for all 20 samples. Further, the TAB-004 assay levels were dependent on tumor stage, as they increased with disease progression (p<0.0001) unlike the CA 15-3 assay, which was unable to predict differences between stages 0, 2, and 3. By comparing the stage data collected to the normal range found in FIG. 10 (<40 U/ml), it appears that TAB-004 was superior to CA 15-3 for diagnosing stage 2 and 3, as all stage 2 and stage 3 patients displayed TAB-004 assay values above the normal range while only 2 out of 10 were above normal for the CA 15-3 assay.

Example 7

Correlating Levels of Circulating MUC1 with Disease Progression and Recurrence

TAB-004 is employed to assess its potential in accurately predicting disease recurrence and progression. Plasma from n=100 patients at stages II and III/IV breast cancer are assessed pre-treatment and 6, 12, and 18-months post end of standard of care therapy. Recurrence in this group is assessed after 24 months. Plasma from n=50 pancreatic patients at stages 2, 3, and 4 is assessed pre-treatment, and 3, 6, 9, and 12 months post standard of care therapy.

Sample Collection.

Plasma is collected at routine follow-up visits. Disease stage is confirmed by pathological assessment and recurrence is confirmed by standard imaging techniques. Databases are maintained detailing any chemotherapies or adjunct therapies administered to the pancreatic cancer patients.

For breast cancer, the recurrence rate is generally much lower compared to pancreatic cancer, and therefore lower numbers of pancreas cancer patients (statistically justified below) are employed. The times for collecting plasma also differ between breast and pancreas cancer due to standard follow-up visit timing.

For pancreatic cancer patients, few stage 3 and 4 patients generally survive more than 6 months to a year, and thus it is not possible to wait for end of treatment to collect samples again due to the high mortality rate after diagnosis. The samples are collected while the patients are undergoing therapy. For patients that undergo surgery, samples are collected before surgery and 3, 6, 9, and 12 months post surgery regardless of their treatment regimen. For patients that have un-resectable cancer, samples are collected at diagnosis prior to start of therapy and then at 3, 6, 9, 12 months post diagnosis regardless of the treatment regimen. Since most patients would be expected to recur within a year, the trial is stopped at 12 months. For breast cancer patients, only stage III/IV are generally expected to recur within 2 years. However for comparison, stage II patients are included. Plasma is collected pre-treatment and then at 6, 12, and 18 months post end of treatment.

Analysis and Statistics: Analyses are performed to determine the ability of TAB-004 assays to predict recurrence and/or death of patients with breast cancer. Patients are divided into those that have a recurrence during the study period and those who do not. Receiver Operating Curves (ROCS) are constructed to determine if there is a natural cut-point for TAB-004 for predicting recurrence. For patients with a recurrence, the prior TAB-004 level are used in the analysis, while the final TAB-004 values are used for those without a recurrence. For instance, if the recurrence occurs at 15 months, then the TAB-004 level at 12 months is used. Cox proportional hazard models are performed with time to recurrence as the dependent (outcome) variable. The Cox model is a multivariate procedure that correctly accounts for lost to follow-up and censored data. Age, cancer stage, and cancer grade, and TAB-004 values are entered as independent predictors. If the ROC determines a natural cut-point for predicting recurrence, then another Cox model is run with this dichotomous (above or below the cutoff) variable replacing the actual value of TAB-004 in the model. A statistically significant p-value for the TAB-004 variable indicates that TAB-004 is an independent predictor of recurrence when adjusting for the patient's age, cancer stage, and grade of the tumor. The previous set of analyses is repeated with time to recurrence or death as the dependent variable. For patients with stage 0, I, and II cancer, this same approach is used to predict time to stage III/IV (metastatic) cancer.

This set of analyses is also performed using the data from the patients with pancreatic cancer. With the extremely high death rate for pancreatic cancer, getting stable estimates of the coefficients in the Cox model when predicting time to recurrence or time to stage 4 disease can be difficult. As such, few recurrences of cancer or few cases of patients progressing from stages 2 or 3 to stage 4 metastatic cancers might occur during the study period.

Example 8

Correlating Levels of TAB-004-positive CTCs with Disease Prognosis and TAB-004 Plasma Levels, and Comparing Numbers and Metastatic Potential of CTCs Isolated with TAB-004 Versus an EpCAM Antibody Circulating Tumor Cells (CTCs) are defined as tumor cells in the bloodstream. Currently, the Veridex CELLSEARCH® system is the only FDA approved method to measure CTCs in metastatic breast, colorectal and prostate cancer patients. Using this system, CTCs in pancreatic cancer patients have shown a correlation between CTCs <1 and survival. Interestingly, in this same study, the presence of CTCs was shown to correlate with increased sera levels of the tumor antigen CA 19-9, indicating that sera levels of tumor antigens can also be predictive of tumor cells in circulation. In metastatic breast cancer patients, it was found that 5 CTCs was an independent predictor of progression-free survival and overall survival. Further, CTC levels in metastatic breast cancer patients are an earlier, more reproducible indication of disease status than current imaging methods.

The approved method for CTC assessment entails isolating EpCAM-expressing cells from the blood and then validating these cells as CTCs with the presence of epithelial-specific cytokeratin staining, proper nucleus staining, and the absence of leukocyte-specific CD45. A caveat to this method is the restriction to EpCAM expressing cells. Studies have suggested that cells acquiring a migratory phenotype lose their epithelial characteristics and acquire mesenchymal features, which phenotypically have been shown to be the cells responsible for aggressive tumor progression. As such, it is apparent that EpCAM isolation of CTCs could "miss" the most potent CTCs—those possessing a mesenchymal phenotype.

Both breast and pancreatic primary and metastastatic tumors express high levels of tumor-associated MUC1 recognized by our TAB-004 antibody. Therefore, CTCs in these patients should be recognized by the TAB-004 antibody. In preliminary experiments, levels of MUC1 were assessed using the TAB-004 antibody. First, the ability to use the Veridex CELLSEARCH® system to measure MUC1-expressing CTCs using 7.5 ml blood samples (analogous to human samples) spiked with PANC1 cells, which are a human pancreatic cancer cell line was tested. Approximately 90% of the CTCs (EpCAM+ cells) expressed MUC1. Further, patient samples were collected, and it was found that TAB-004 recognizes CTCs at from about 33% to 100% efficiency. Therefore, using the TAB-004 antibody appears to accurately detect micrometastases in pancreatic and breast cancer patients.

REFERENCES

All references listed below, as well as all references cited in the instant disclosure, including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

Adams et al. (1993) *Cancer Res* 53:4026-4034.
Alexay et al. (1996) *The PCT International Society of Optical Engineering* 2705/63.
Al-Hajj et al. (2003) *Proc Natl Acad Sci USA* 100:3983-3988.
Alt et al. (1999) *FEBS Lett* 454:90-94.

Amemiya et al. (1988) *Topics Curr Chem* 147:121-144.
Barratt-Boyes (1996) *Cancer Immunol Immunother* 43:142-151.
Basu et al. (2006) *J Immunol* 177:2391-2402.
Bauminger & Wilchek (1980) *Meth Enzymol* 70:151-159.
Berkow et al. (1997) *The Merck Manual of Medical Information*, Home ed. Merck Research Laboratories, Whitehouse Station, N.J., United States of America.
Bieche & Lidereau (1997) *Cancer Genetics and Cytogenetics* 98:75-80.
Bird et al. (1988) *Science* 242:423-426.
Blaskovich et al. (2003) *Cancer Res* 63:1270-1279.
Bonnet & Dick (1997) *Nat Med* 3:730-737.
Brabletz et al. (2005) *Nat Rev Cancer* 5:744-749.
Cameron et al. (2009) *Bioorg Med Chem Lett* 19:2075-2078.
Chattopadhyay et al. (2001) *Nucl Med Biol* 28:741-744.
Cheng (1996) *Hum Gene Ther* 7:275-282.
Chothia & Lesk (1987) *J Mol Biol* 196:901-917.
Cristofanilli et al. (2005) *J Clin Oncol* 23:1420-1430.
Clackson et al. (1991) *Nature* 352:624-628.
Coatney (2001) *Ilar J* 42:233-247.
Coloma et al. (1997) *Nature Biotechnol* 15:159-163.
David et al. (1974) *Biochemistry* 13:1014.
DeCosta Byfield et al. (2004) *Mol Pharmacol* 65:744-752.
Dong et al. (1997) *J Pathology* 183:311-317.
Dontu et al. (2004) *Breast Cancer Res* 6:R605-615.
Donzella et al. (1998) *Nat Med* 4:72-77.
Duch et al. (1998) *Toxicol. Lett.* 100-101:255-263.
Ebadi (1998) *CRC Desk Reference of Clinical Pharmacology*. CRC Press, Boca Raton, Fla., United States of America.
Emanueli et al. (2004) *Arterioscler Thromb Vasc Biol* 24:2082-2087.
European Patent No 0 439 095.
Fong et al. (1999) *Cancer Res* 59:99-106.
Fraser (1996) *Meth Cell Biol* 51:147-160.
GENBANK® Accession Nos. AAA39755; AAA60019; AAO63589; J055821; NM_004985.3; NP_001181906; NP_004976; NP_036734; NP_038633; P_776540; Q02496.
Gennaro (1990) *Remington's Pharmaceutical Sciences, 18th ed.*, Mack Pub. Co., Easton, Pa., United States of America.
Gennaro (ed.) (2003) *Remington: The Science and Practice of Pharmacy, 20th edition* Lippincott, Williams & Wilkins, Philadelphia, Pa., United States of America.
Glockshuber et al. (1990) *Biochemistry* 29:1362-1367.
Gold et al. (2007) *Clin Cancer Res* 13:7380-7387.
Goldman et al. (1997) *Cancer Res* 57:1447-1451.
Goodman et al. (1996) *Goodman & Gilman's the Pharmacological Basis of Therapeutics*, 9th ed. McGraw-Hill Health Professions Division, New York, N.Y., United States of America.
Hallahan et al. (2001a) *Am J Clin Oncol* 24:473-480.
Hallahan et al. (2001b) *J Control Release* 74:183-191.
Hamers-Casterman et al. (1993) *Nature* 363:446-448.
Harlow & Lane (1988) *Antibodies: A Laboratory Manual*, Cold Spring Harbor Laboratory Press, Cold Spring Harbor, N.Y., United States of America).
Heijnen et al. (1997) *J Immunol* 159:5629-5639.
Henderson et al. (1998) *J Immunother* 21:247-256.
Heredia et al. (1991) *J Neurosci Meth* 36:17-25.
Hingorani et al. (2003) *Cancer Cell* 4:437-450.
Hnatowich et al. (1996) *J Pharmacol Exp Ther* 276:326-334.
Holliger et al. (1993) *Proc Natl Acad Sci USA* 90:6444-6448.
Holliger et al. (1999) *Cancer Res* 59:2909-2916.
Hu et al. (1996) *Cancer Res* 56:3055-3061.
Hunter et al. (1962) *Nature* 144:945.
Huston et al. (1988) *Proc Natl Acad Sci USA* 85:5879-5883.
Huston et al. (1993) *Int Rev Immunol* 10:195-217.
Jackson et al. (2001) *Genes Dev* 15:3243-3248.
Johnson & Wu (2000) *Nucleic Acids Res* 28:214-218.
Kabat et al. (1991) (1991) *Sequences of Proteins of Immunological Interest, Fifth Edition*. NIH Publication No. 91-3242.
Kahn et al. (1987) *Anticancer Res* 7:639-652.
Kahn et al. (1987) *Anticancer Res* 7(4A):639-652.
Katzung (2001) *Basic & Clinical Pharmacology, 8th ed.*, Lange Medical Books/McGraw-Hill Medical Pub. Division, New York, N.Y., United States of America.
Kawaguchi et al. (2002) *Nat Genet* 32:128-134.
Kipriyanov et al. (1995) *Cell Biophys* 26:187-204.
Kipriyanov et al. (1998), *Int J Cancer* 77:763-772.
Kipriyanov et al. (1999) *J Mol Biol* 293:41-56.
Kohler et al. (1975) *Nature* 256:495.
Kontermann et al. (1999) *J Immunol Meth* 226:179-188.
Kortt et al. (1997) *Protein Eng* 10:423-433.
Kostelny et al. (1992), *J Immunol* 148:1547-1553.
Kurihara et al. (2008) *J Hepatobiliary Pancreat Surg* 15:189-195.
Kurucz et al. (1995) *J Immunol* 154:4576-4582.
Le Gall et al. (1999) *FEBS Lett* 453:164-168.
Lees (2001) *Semin Ultrasound CT MR* 22:85-105.
Licha et al. (2000) *Photochem Photobiol* 72:392-398.
Littlefield et al. (2008) *Inorg Chem* 47:2798-2804.
Manome et al. (1994) *Cancer Res* 54:5408-5413.
Marks et al. (1991) *J Mol Biol* 222:581-597.
Martin (1996) *Proteins* 25:130-133.
McCartney et al. (1995) *Protein Eng* 8:301-314.
McGucken et al. (1995) *Human Pathology* 26: 432-439.
Mukherjee et al. (2000) *J Immunol* 165:3451-3460.
Mukherjee et al. (2007) *Vaccine* 25:1607-1618.
Mukherjee et al. (2009) *J Immunol* 182:216-224.
Muller & Scherle (2006) *Nature Rev Can* 6:613-625.
Muller et al. (1998) *FEBS Lett* 432:45-49.
Nabel (1997) Vectors for Gene Therapy In *Current Protocols in Human Genetics*, John Wiley & Sons, New York, N.Y., United States of America.
Neri et al. (1997) *Nat Biotechnol* 15:1271-1275.
Nygren (1982) *J Histochem Cytochem* 30:407.
Pack et al. (1992) *Biochemistry* 31:1579-1584.
Pain et al. (1981) *J Immunol Meth* 40:219).
Pardal et al. (2003) *Nat Rev Cancer* 3:895-902.
Park et al. (1997) *Adv Pharmacol* 40:399-435.
Pasqualini et al. (1997) *Nat Biotechnol* 15:542-546.
Paul (1993) *Fundamental Immunology*, Raven Press, New York, N.Y., United States of America.
PCT International Patent Application Publication Nos. WO 1992/22653; WO 1993/25521.
Pearson & Lipman (1988) *Proc Natl Acad Sci USA* 85:2444-2448.
Perkins et al. (2003) *Am Fam Physician* 68:1075-1082.
Peterson et al. (1991) in *Breast Epithelial Antigens*, (Ceriani, ed), Plenum Press, New York, N.Y., United States of America, pages 55-68.
Pomper & Port (2000) *Magn Reson Imaging Clin N Am* 8:691-713.
Price et al. (1998) *Tumor Biology* 19:1 20.
Quin et al. (2000) *Int J Cancer* 87:499-506.
Ragnarson et al. (1992) *Histochemistry* 97:329-333.
Reya et al. (2001) *Nature* 414:105-111.
Rothenfusser et al. (2002) *Human Immunology* 63:1111-1119.
Rovaris et al. (2001) *J Neurol Sci* 186 Suppl 1:S3-9.
Rowse et al. (1998) *Cancer Res* 58:315-321.

Rugo et al. (2005) *J Clin Oncol* 23:5474-5483.
Sagiuchi et al. (2001) *Ann Nucl Med* 15:267-270.
Saltzman & Fung (1997) *Adv Drug Deliv Rev* 26:209-230.
Sambrook & Russell (2001) *Molecular Cloning: a Laboratory Manual*, 3rd ed Cold Spring Harbor Laboratory Press, Cold Spring Harbor, N.Y., United States of America.
Sawyer et al. (2004) *Bioorg Med Chem Lett* 14:3581-3584.
Schwendener (1992) *Chimia* 46:69-77.
Shalaby et al. (1992) *J Exp Med* 175:217-225.
Sharkey et al. (2003) *Cancer Res* 63:354-363.
Sharkey et al. (2003) *Clin Cancer Res* 9:3897S-3913S.
Shen et al. (1993) *Magn Reson Med* 29:599-604.
Speight et al. (1997) *Avery's Drug Treatment: A Guide to the Properties, Choice, Therapeutic Use and Economic Value of Drugs in Disease Management*, 4th ed., Adis International, Auckland, New Zealand.
Singh et al. (2004) *Nature* 432:396-401.
Tavitian et al. (1998) *Nat Med* 4:467-471.
Tinder et al. (2008) *J Immunol* 181:3116-3125.
U.S. Pat. Nos. 4,551,482; 4,816,567; 5,088,499; 5,147,631; 5,234,933; 5,326,902; 5,490,840; 5,510,103; 5,574,172; 5,651,991; 5,688,931; 5,707,605; 5,714,166; 5,738,837; 5,786,387; 5,855,900; 5,858,410; 5,865,754; 5,922,356; 5,922,545; 5,928,627; 5,994,392; 6,024,938; 6,071,890; 6,080,384; 6,083,486; 6,106,866; 6,127,339; 6,172,197; 6,221,018; 6,231,834; 6,245,318; 6,246,901; 6,248,516; 6,254,852; 6,291,158; 6,548,643; 7,183,388.
Vinogradov et al. (1996) *Biophys J* 70:1609-1617.
Weissleder et al. (1992) *Magn Reson Q* 8:55-63.
Weissleder et al. (1999) *Nat Biotechnol* 17:375-378.
Whitlow et al. (1991) *Methods companion Methods Enzymol* 2:97-105.
Yoo et al. (1997) *J Nucl Med* 38:294-300.
Zhu et al. (1997) *Protein Sci* 6:781-788.
Zola (1987) *Monoclonal Antibodies: A Manual of Techniques*, CRC Press, Inc, Boca Raton, Fla., United States of America, pp 147-158.

SEQUENCES

SEQ ID NO: 1: MTPGTQSPFFLLLLLTVLTVVTGSGHASSTPGGEKE
TSATQRSSVPSSTEKNAVSMTSSVLSSHSPGSGSSTTQGQDVTLAPATEP
ASGSAATWGQDVTSVPVTRPALGSTTPPAHDVTSAPDNKPAPGSTAPPAH
GVTSAPDTRPAPGSTAPPAHGVTSAPDTRPAPGSTAPPAHGVTSAPDTRP
APGSTAPPAHGVTSAPDTRPAPGSTAPPAHGVTSAPDTRPAPGSTAPPAH
GVTSAPDTRPAPGSTAPPAHGVTSAPDTRPAPGSTAPPAHGVTSAPDTRP
APGSTAPPAHGVTSAPDTRPAPGSTAPPAHGVTSAPDTRPAPGSTAPPAH
GVTSAPDTRPAPGSTAPPAHGVTSAPDTRPAPGSTAPPAHGVTSAPDTRP
APGSTAPPAHGVTSAPDTRPAPGSTAPPAHGVTSAPDTRPAPGSTAPPAH
GVTSAPDTRPAPGSTAPPAHGVTSAPDTRPAPGSTAPPAHGVTSAPDTRP
APGSTAPPAHGVTSAPDTRPAPGSTAPPAHGVTSAPDTRPAPGSTAPPAH
GVTSAPDTRPAPGSTAPPAHGVTSAPDTRPAPGSTAPPAHGVTSAPDTRP
APGSTAPPAHGVTSAPDTRPAPGSTAPPAHGVTSAPDTRPAPGSTAPPAH
GVTSAPDTRPAPGSTAPPAHGVTSAPDTRPAPGSTAPPAHGVTSAPDTRP

-continued

SEQUENCES

APGSTAPPAHGVTSAPDTRPAPGSTAPPAHGVTSAPDTRPAPGSTAPPAH
GVTSAPDTRPAPGSTAPPAHGVTSAPDTRPAPGSTAPPAHGVTSAPDTRP
APGSTAPPAHGVTSAPDTRPAPGSTAPPAHGVTSAPDTRPAPGSTAPPAH
GVTSAPDNRPALGSTAPPVHNVTSASGSASGSASTLVHNGTSARATTTPA
SKSTPFSIPSHHSDTPTTLASHSTKTDASSTHHSSVPPLTSSNHSTSPQL
STGVSFFFLSFHISNLQFNSSLEDPSTDYYQELQRDISEMFLQTYKQGGF
LGLSNIKFRPGSVVVQLTLAFREGTINVHDVETQFNQYKTEAASRYNLTI
SDVSVSDVPFPFSAQSGAGVPGWGIALLVLVCVLALAIVYLIALAVCQC
RRKNYGQLDIFPARDTYHPMSEYPTYHTHGRYVPPSSTDRSPYEKVSAGN
GGSSLSYTNPAVAAASANL

SEQ ID NO: 2: MTEYKLVVVGAGGVGKSALTIQLIQNHFVDEYDPTI
EDSYRKQVVIDGETCLLDILDTAGQEEYSAMRDQYMRTGEGFLCVFAINN
TKSFEDIHHYREQIKRVKDSEDVPMVLVGNKCDLPSRTVDTKQAQDLARS
YGIPFIETSAKTRQGVDDAFYTLVREIRKHKEKMSKDGKKKKKKSKTKCV
IM

SEQ ID NO: 3: STAPPVHNVTSAPDTRPAPGSTAPP

SEQ ID NO: 4: gaggtccagctgcagcagtctgggggtgaacgggca
acacctggggcctcagtgaagatgtcctgcaagacttctggctacacctt
tactaactactggatgcactgggtaaaacagaggcctggacagggtctgg
aatggattggatacattaatcctagcagtggttatactcagtacaatcag
aagttcaaggacaaggccacattgactgcagacaaatcctccagcacagc
ctacatacaactaagcagcctgacatctgaagactctgcagtctattact
gttcaacctactatggtgactacttgtttccttactggggccaagggact
ctggtcactgtctctgca SEQ ID NO: 5: EVQLQQSGGERATPGASVKMSCKTSGYTFTNYWMHW
VKQRPGQGLEWIGYINPSSGYTQYNQKFKDKATLTADKSSSTAYIQLSSL
TSEDSAVYYCSTYYGDYLFPYWGQGTLVTVSA SEQ ID NO: 6: gatgttttgatgacccaaactccactctccctgcct
gtcagtcttggagatcaagcctccatctcttgcagatctagtcaggacat
tgtatatggtaatggaaacacctatttagaatggtacctgcagaaaccag
gccagtctccaaagctcctgatctacaaagtttccaaccggttttctggg
gtcccagacaggttcagtggcagtggatcagggacagatttcacactcaa
gatcagcagagtggaggctgaggatctgggagtttattactgctttcaag
gttcacatgttccgtacacgttcggaggggggaccaagctggaaataaaa
cgg SEQ ID NO: 7: DVLMTQTPLSLPVSLGDQASISCRSSQDIVYGNGNT
YLEWYLQKPGQSPKLLIYKVSNRFSGVPDRFSGSGSGTDFTLKISRVEAE
DLGVYYCFQGSHVPYTFGGGTKLEIKR

SEQ ID NO: 8: GYTFTNYW

SEQ ID NO: 9: INPSSGYT

SEQ ID NO: 10: STYYGDYLFPY

SEQ ID NO: 11: QDIVYGNGNTY

SEQ ID NO: 12: KVS

SEQ ID NO: 13: FQGSHVPYT

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. An isolated antibody, or a fragment or derivative thereof, comprising the complementarity determining regions (CDRs) of monoclonal antibody TAB-004 produced by hybridoma cell line TAB-004 deposited with the American Type Culture Collection (ATCC) as Accession No. PTA-11550 on Dec. 16, 2010, wherein:
   (i) the CDRs of monoclonal antibody TAB-004 comprise a heavy chain CDR1 comprising SEQ ID NO: 8; a heavy chain CDR2 comprising SEQ ID NO: 9; a heavy chain CDR3 comprising SEQ ID NO: 10; a light chain CDR1 comprising SEQ ID NO: 11; a light chain CDR2 comprising SEQ ID NO: 12; and a light chain CDR3 comprising SEQ ID NO: 13; and
   (ii) the isolated antibody, or the fragment or derivative thereof comprises a heavy chain variable region at least 95% identical to SEQ ID NO: 5 and a light chain variable region at least 95% identical to SEQ ID NO: 7.

2. The isolated antibody, or the fragment or derivative thereof, of claim 1, wherein said isolated antibody, or fragment or derivative thereof is polyclonal.

3. The isolated antibody, or the fragment or derivative thereof, of claim 1, wherein said isolated antibody, or fragment or derivative thereof is monoclonal.

4. The isolated antibody, or the fragment or derivative thereof, of claim 1, wherein said isolated antibody, or fragment or derivative thereof is human or humanized.

5. The isolated antibody, or the fragment or derivative thereof, of claim 1, which is selected from the group consisting of a monoclonal antibody produced by hybridoma cell line TAB-004 deposited with the American Type Culture Collection (ATCC) as Accession No. PTA-11550 on Dec. 16, 2010; a chimeric antibody, or a fragment or derivative thereof; a humanized antibody, or a fragment or derivative thereof; a human antibody, or a fragment or derivative thereof; a single chain antibody, or a fragment or derivative thereof; and a Fab fragment, wherein the chimeric antibody, the humanized antibody, the human antibody, the single chain antibody, or the Fab fragment comprises the CDRs of monoclonal antibody TAB-004.

6. The isolated antibody, or the fragment or derivative thereof, of claim 1, wherein the antibody, or the fragment or derivative thereof comprises a heavy chain variable region that is encoded by a nucleic acid molecule comprising SEQ ID NO: 4 and/or a light chain variable region that is encoded by a nucleic acid molecule comprising SEQ ID NO: 6.

7. A composition comprising the antibody, or the fragment or derivative thereof, of claim 1 and a pharmaceutically acceptable carrier, optionally wherein the pharmaceutically acceptable carrier is acceptable for use in a human.

8. A composition comprising the antibody, or the fragment or derivative thereof, of claim 1 conjugated to an active agent.

9. The composition of claim 8, wherein the active agent is selected from the group consisting of a radioactive molecule, a radionuclide, a sensitizer molecule, an imaging reagent, a radioisotope, a toxin, a cytotoxin, an anti-angiogenic agent, an anti-tumor agent, a chemotherapeutic agent, an immunomodulator, a cytokine, a reporter group, and combinations thereof.

10. The composition of claim 9, wherein the radioisotope is selected from the group consisting of $^{10}$B, $^{211}$At, $^{212}$Pb, $^{212}$Bi, $^{125}$I, $^{131}$I, $^{35}$S, and $^{3}$H.

11. The composition of claim 9, wherein the immunomodulator is selected from the group consisting of an indoleamine 2,3-dioxygenase (IDO) inhibitor; an EP2/EP4 receptor antagonist; a cyclooxygenase inhibitor; and a dendritic cell activator.

12. An isolated cell that produces the antibody, or the fragment or derivative thereof, of claim 1.

13. A method for detecting a tumor and/or a cancer cell in a subject, comprising:
   (a) contacting a biological sample in the subject or isolated from the subject with composition comprising the antibody, or the fragment or derivative thereof of claim 1 under conditions sufficient for the antibody, or the fragment or derivative thereof of claim 1 to bind to an epitope present on a tumor and/or a cancer cell, if present, in the biological sample; and
   (b) detecting binding of the antibody, or the fragment or derivative thereof, of claim 1 the epitope,
wherein the detecting is indicative of a tumor and/or a cancer cell being present in the subject.

14. The method of claim 13, wherein the tumor and/or the cancer cell is a tumor of the pancreas, breast, ovary, colon, or rectum, and/or a metastatic cell derived therefrom, which expresses MUC1, a mutant K-ras, or both.

15. The method of claim 13, wherein the antibody, or the fragment or derivative thereof is conjugated to detectable label comprising an imaging agent selected from the group consisting of paramagnetic, radioactive, and fluorogenic ions.

16. The method of claim 15, wherein the radioactive imaging agent is selected from the group consisting of gamma-emitters, positron-emitters and x-ray-emitters.

17. The method of claim 16, wherein the radioactive imaging agent is selected from the group consisting of $^{43}$K, $^{52}$Fe, $^{57}$Co, $^{67}$Cu, $^{67}$Ga, $^{68}$Ga, $^{77}$Br, $^{81}$Rb/$^{81}$MKr, $^{87M}$Sr, $^{99M}$Tc, $^{111}$In, $^{113}$In, $^{123}$I, $^{125}$I, $^{127}$Cs, $^{129}$Cs, $^{131}$I, $^{132}$I, $^{197}$Hg, $^{203}$Pb, and $^{206}$Bi.

18. The method of claim 13, wherein the biological sample is a blood sample, or a fraction derived therefrom.

19. A method for suppressing tumor growth in a subject, the method comprising administering to a subject bearing a tumor an effective amount of the isolated antibody, or a fragment or derivative thereof of claim 1.

20. The method of claim 19, wherein the tumor is a tumor of the pancreas, breast, ovary, colon, or rectum, and/or a metastatic cell derived therefrom, which expresses MUC1, a mutant K-ras, or both.

21. The method of claim 19, further comprising administering to the subject one or more additional anti-tumor treatments.

22. The method of claim 21, wherein the one or more additional anti-tumor treatments are selected from the group consisting of radiotherapy, chemotherapy, an additional immunotherapy, an anti-inflammatory therapy, and combinations thereof.

23. The method of claim 22, wherein the anti-inflammatory therapy comprises administering to the subject a cyclooxygenase-2-specific inhibitor.

24. The method of claim 22, wherein the one or more additional anti-tumor therapies comprise administering gemcitabine (4-amino-1-(2-deoxy-2,2-difluoro-β-D-erythro-pentofuranosyl)pyrimidin-2(1H)-on-2',2'-difluoro-2'-deoxycytidine) and celecoxib (4-[5-(4-methylphenyl)-3-(trifluoromethyl)pyrazol-1-yl]benzenesulfonamide), or pharmaceutically acceptable salts of either or both thereof, to the subject.

25. The method of claim 19, wherein the antibody, or the fragment or derivative thereof of claim 1, is encoded by a nucleic acid molecule comprising SEQ ID NO: 4 and/or a light chain variable region is encoded by a nucleic acid molecule comprising SEQ ID NO: 6.

26. The composition of claim 11, wherein the immunomodulator is selected from the group consisting of 1-methyl-DL-tryptophan (1MT), indomethacin, and CpG oligodeoxynucleotides (CpG ODN).

* * * * *

SEQUENCE LISTING

<160> NUMBER OF SEQ ID NOS: 13

<210> SEQ ID NO 1
<211> LENGTH: 1255
<212> TYPE: PRT
<213> ORGANISM: Homo sapiens

<400> SEQUENCE: 1

```
Met Thr Pro Gly Thr Gln Ser Pro Phe Phe Leu Leu Leu Leu Thr
 1               5                  10                  15

Val Leu Thr Val Val Thr Gly Ser Gly His Ala Ser Ser Thr Pro Gly
             20                  25                  30

Gly Glu Lys Glu Thr Ser Ala Thr Gln Arg Ser Ser Val Pro Ser Ser
         35                  40                  45

Thr Glu Lys Asn Ala Val Ser Met Thr Ser Ser Val Leu Ser Ser His
     50                  55                  60

Ser Pro Gly Ser Gly Ser Ser Thr Thr Gln Gly Gln Asp Val Thr Leu
 65                  70                  75                  80

Ala Pro Ala Thr Glu Pro Ala Ser Gly Ser Ala Ala Thr Trp Gly Gln
                 85                  90                  95

Asp Val Thr Ser Val Pro Val Thr Arg Pro Ala Leu Gly Ser Thr Thr
             100                 105                 110

Pro Pro Ala His Asp Val Thr Ser Ala Pro Asp Asn Lys Pro Ala Pro
         115                 120                 125

Gly Ser Thr Ala Pro Pro Ala His Gly Val Thr Ser Ala Pro Asp Thr
     130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
    370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415
```

```
Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
            435                 440                 445

Gly Ser Thr Ala Pro Pro Ala His Gly Val Thr Ser Ala Pro Asp Thr
450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
            485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
            515                 520                 525

Gly Ser Thr Ala Pro Pro Ala His Gly Val Thr Ser Ala Pro Asp Thr
530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
            565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
            595                 600                 605

Gly Ser Thr Ala Pro Pro Ala His Gly Val Thr Ser Ala Pro Asp Thr
610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
            645                 650                 655

Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
            675                 680                 685

Gly Ser Thr Ala Pro Pro Ala His Gly Val Thr Ser Ala Pro Asp Thr
690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
            725                 730                 735

Gly Val Thr Ser Ala Pro Asp Thr Arg Pro Ala Pro Gly Ser Thr Ala
            740                 745                 750

Pro Pro Ala His Gly Val Thr Ser Ala Pro Asp Thr Arg Pro Ala Pro
            755                 760                 765

Gly Ser Thr Ala Pro Pro Ala His Gly Val Thr Ser Ala Pro Asp Thr
770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
            805                 810                 815

Gly Val Thr Ser Ala Pro Asp Thr Arg Pro Ala Pro Gly Ser Thr Ala
            820                 825                 830
```

```
Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
            885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
            915                 920                 925

Gly Ser Thr Ala Pro Pro Ala His Gly Val Thr Ser Ala Pro Asp Asn
930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
            995                 1000                1005

Ser Thr Lys Thr Asp Ala Ser Thr His His Ser Ser Val Pro
        1010                1015                1020

Pro Leu Thr Ser Ser Asn His Ser Thr Ser Pro Gln Leu Ser Thr
        1025                1030                1035

Gly Val Ser Phe Phe Phe Leu Ser Phe His Ile Ser Asn Leu Gln
        1040                1045                1050

Phe Asn Ser Ser Leu Glu Asp Pro Ser Thr Asp Tyr Tyr Gln Glu
        1055                1060                1065

Leu Gln Arg Asp Ile Ser Glu Met Phe Leu Gln Ile Tyr Lys Gln
        1070                1075                1080

Gly Gly Phe Leu Gly Leu Ser Asn Ile Lys Phe Arg Pro Gly Ser
        1085                1090                1095

Val Val Val Gln Leu Thr Leu Ala Phe Arg Glu Gly Thr Ile Asn
        1100                1105                1110

Val His Asp Val Glu Thr Gln Phe Asn Gln Tyr Lys Thr Glu Ala
        1115                1120                1125

Ala Ser Arg Tyr Asn Leu Thr Ile Ser Asp Val Ser Val Ser Asp
        1130                1135                1140

Val Pro Phe Pro Phe Ser Ala Gln Ser Gly Ala Gly Val Pro Gly
        1145                1150                1155

Trp Gly Ile Ala Leu Leu Val Leu Val Cys Val Leu Val Ala Leu
        1160                1165                1170

Ala Ile Val Tyr Leu Ile Ala Leu Ala Val Cys Gln Cys Arg Arg
        1175                1180                1185

Lys Asn Tyr Gly Gln Leu Asp Ile Phe Pro Ala Arg Asp Thr Tyr
        1190                1195                1200

His Pro Met Ser Glu Tyr Pro Thr Tyr His Thr His Gly Arg Tyr
        1205                1210                1215

Val Pro Pro Ser Ser Thr Asp Arg Ser Pro Tyr Glu Lys Val Ser
        1220                1225                1230
```

```
Ala Gly Asn Gly Gly Ser Ser Leu Ser Tyr Thr Asn Pro Ala Val
    1235                1240                1245

Ala Ala Ala Ser Ala Asn Leu
    1250                1255

<210> SEQ ID NO 2
<211> LENGTH: 188
<212> TYPE: PRT
<213> ORGANISM: Homo sapiens

<400> SEQUENCE: 2

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 3
<211> LENGTH: 25
<212> TYPE: PRT
<213> ORGANISM: Artificial Sequence
<220> FEATURE:
<223> OTHER INFORMATION: Artificially synthesized peptide

<400> SEQUENCE: 3

Ser Thr Ala Pro Pro Val His Asn Val Thr Ser Ala Pro Asp Thr Arg
1               5                   10                  15

Pro Ala Pro Gly Ser Thr Ala Pro Pro
            20                  25

<210> SEQ ID NO 4
<211> LENGTH: 354
<212> TYPE: DNA
<213> ORGANISM: Artificial Sequence
<220> FEATURE:
<223> OTHER INFORMATION: Recombinantly generated IgG with TAB-004 CDRs-
      heavy chain sequence
<220> FEATURE:
<221> NAME/KEY: CDS
<222> LOCATION: (1)..(354)
```

<400> SEQUENCE: 4

```
gag gtc cag ctg cag cag tct ggg ggt gaa cgg gca aca cct ggg gcc      48
Glu Val Gln Leu Gln Gln Ser Gly Gly Glu Arg Ala Thr Pro Gly Ala
1               5                   10                  15 tca gtg aag atg tcc tgc aag act tct ggc tac acc ttt act aac tac      96
Ser Val Lys Met Ser Cys Lys Thr Ser Gly Tyr Thr Phe Thr Asn Tyr
            20                  25                  30 tgg atg cac tgg gta aaa cag agg cct gga cag ggt ctg gaa tgg att     144
Trp Met His Trp Val Lys Gln Arg Pro Gly Gln Gly Leu Glu Trp Ile
        35                  40                  45 gga tac att aat cct agc agt ggt tat act cag tac aat cag aag ttc     192
Gly Tyr Ile Asn Pro Ser Ser Gly Tyr Thr Gln Tyr Asn Gln Lys Phe
50                  55                  60 aag gac aag gcc aca ttg act gca gac aaa tcc tcc agc aca gcc tac     240
Lys Asp Lys Ala Thr Leu Thr Ala Asp Lys Ser Ser Ser Thr Ala Tyr
65                  70                  75                  80 ata caa cta agc agc ctg aca tct gaa gac tct gca gtc tat tac tgt     288
Ile Gln Leu Ser Ser Leu Thr Ser Glu Asp Ser Ala Val Tyr Tyr Cys
                85                  90                  95 tca acc tac tat ggt gac tac ttg ttt cct tac tgg ggc caa ggg act     336
Ser Thr Tyr Tyr Gly Asp Tyr Leu Phe Pro Tyr Trp Gly Gln Gly Thr
            100                 105                 110 ctg gtc act gtc tct gca                                              354
Leu Val Thr Val Ser Ala
        115
```

<210> SEQ ID NO 5
<211> LENGTH: 118
<212> TYPE: PRT
<213> ORGANISM: Artificial Sequence
<220> FEATURE:
<223> OTHER INFORMATION: Synthetic Construct

<400> SEQUENCE: 5

```
Glu Val Gln Leu Gln Gln Ser Gly Gly Glu Arg Ala Thr Pro Gly Ala
1               5                   10                  15

Ser Val Lys Met Ser Cys Lys Thr Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Tyr Ile Asn Pro Ser Ser Gly Tyr Thr Gln Tyr Asn Gln Lys Phe
50                  55                  60

Lys Asp Lys Ala Thr Leu Thr Ala Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ser Thr Tyr Tyr Gly Asp Tyr Leu Phe Pro Tyr Trp Gly Gln Gly Thr
            100                 105                 110

Leu Val Thr Val Ser Ala
        115
```

<210> SEQ ID NO 6
<211> LENGTH: 339
<212> TYPE: DNA
<213> ORGANISM: Artificial Sequence
<220> FEATURE:
<223> OTHER INFORMATION: Recombinantly generated IgG with TAB-004 CDRs-
      light chain sequence
<220> FEATURE:
<221> NAME/KEY: CDS
<222> LOCATION: (1)..(339)

-continued

<400> SEQUENCE: 6

```
gat gtt ttg atg acc caa act cca ctc tcc ctg cct gtc agt ctt gga      48
Asp Val Leu Met Thr Gln Thr Pro Leu Ser Leu Pro Val Ser Leu Gly
1               5                   10                  15 gat caa gcc tcc atc tct tgc aga tct agt cag gac att gta tat ggt      96
Asp Gln Ala Ser Ile Ser Cys Arg Ser Ser Gln Asp Ile Val Tyr Gly
            20                  25                  30 aat gga aac acc tat tta gaa tgg tac ctg cag aaa cca ggc cag tct     144
Asn Gly Asn Thr Tyr Leu Glu Trp Tyr Leu Gln Lys Pro Gly Gln Ser
        35                  40                  45 cca aag ctc ctg atc tac aaa gtt tcc aac cgg ttt tct ggg gtc cca     192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc     240
Asp Arg Phe Ser Gly Ser Gly Ser Gly Thr Asp Phe Thr Leu Lys Ile
65                  70                  75                  80 agc aga gtg gag gct gag gat ctg gga gtt tat tac tgc ttt caa ggt     288
Ser Arg Val Glu Ala Glu Asp Leu Gly Val Tyr Tyr Cys Phe Gln Gly
                85                  90                  95 tca cat gtt ccg tac acg ttc gga ggg ggg acc aag ctg gaa ata aaa     336
Ser His Val Pro Tyr Thr Phe Gly Gly Gly Thr Lys Leu Glu Ile Lys
            100                 105                 110 cgg                                                                  339
Arg
```

<210> SEQ ID NO 7
<211> LENGTH: 113
<212> TYPE: PRT
<213> ORGANISM: Artificial Sequence
<220> FEATURE:
<223> OTHER INFORMATION: Synthetic Construct

<400> SEQUENCE: 7

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asp Ile Val Tyr Gly
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg
```

<210> SEQ ID NO 8
<211> LENGTH: 8
<212> TYPE: PRT
<213> ORGANISM: Artificial Sequence
<220> FEATURE:
<223> OTHER INFORMATION: CDR1 sequence from heavy chain of TAB-004
    antibody

<400> SEQUENCE: 8

```
Gly Tyr Thr Phe Thr Asn Tyr Trp
1               5
```

```
<210> SEQ ID NO 9
<211> LENGTH: 8
<212> TYPE: PRT
<213> ORGANISM: Artificial Sequence
<220> FEATURE:
<223> OTHER INFORMATION: CDR2 sequence from heavy chain of TAB-004
      antibody

<400> SEQUENCE: 9

Ile Asn Pro Ser Ser Gly Tyr Thr
1               5

<210> SEQ ID NO 10
<211> LENGTH: 11
<212> TYPE: PRT
<213> ORGANISM: Artificial Sequence
<220> FEATURE:
<223> OTHER INFORMATION: CDR3 sequence from heavy chain of TAB-004
      antibody

<400> SEQUENCE: 10

Ser Thr Tyr Tyr Gly Asp Tyr Leu Phe Pro Tyr
1               5                   10

<210> SEQ ID NO 11
<211> LENGTH: 11
<212> TYPE: PRT
<213> ORGANISM: Artificial Sequence
<220> FEATURE:
<223> OTHER INFORMATION: CDR1 sequence from light chain of TAB-004
      antibody

<400> SEQUENCE: 11

Gln Asp Ile Val Tyr Gly Asn Gly Asn Thr Tyr
1               5                   10

<210> SEQ ID NO 12
<211> LENGTH: 3
<212> TYPE: PRT
<213> ORGANISM: Artificial Sequence
<220> FEATURE:
<223> OTHER INFORMATION: CDR2 sequence from light chain of TAB-004
      antibody

<400> SEQUENCE: 12

Lys Val Ser
1

<210> SEQ ID NO 13
<211> LENGTH: 9
<212> TYPE: PRT
<213> ORGANISM: Artificial Sequence
<220> FEATURE:
<223> OTHER INFORMATION: CDR3 sequence from light chain of TAB-004
      antibody

<400> SEQUENCE: 13

Phe Gln Gly Ser His Val Pro Tyr Thr
1               5
```